US011596631B2

(12) United States Patent
Hayes et al.

(10) Patent No.: US 11,596,631 B2
(45) Date of Patent: Mar. 7, 2023

(54) CDK12 INHIBITORS AND THEIR USES

(71) Applicant: The University of Nottingham, Nottingham (GB)

(72) Inventors: Christopher James Hayes, Nottingham (GB); John David Brook, Nottingham (GB); Ami Ketley, Nottingham (GB)

(73) Assignee: THE UNIVERSITY OF NOTTINGHAM, Nottingham (GB)

( * ) Notice: Subject to any disclaimer, the term of this patent is extended or adjusted under 35 U.S.C. 154(b) by 394 days.

(21) Appl. No.: 16/087,484

(22) PCT Filed: Mar. 23, 2017

(86) PCT No.: PCT/GB2017/050824
§ 371 (c)(1),
(2) Date: Sep. 21, 2018

(87) PCT Pub. No.: WO2017/163076
PCT Pub. Date: Sep. 28, 2017

(65) Prior Publication Data
US 2019/0038625 A1 Feb. 7, 2019

(30) Foreign Application Priority Data
Mar. 24, 2016 (GB) ...................... 1605126

(51) Int. Cl.
*A61K 31/506* (2006.01)
*A61K 45/06* (2006.01)
*A61K 31/454* (2006.01)
*A61K 31/519* (2006.01)
*A61K 31/7088* (2006.01)
*A61K 31/426* (2006.01)
*A61K 31/635* (2006.01)
*A61P 21/00* (2006.01)

(52) U.S. Cl.
CPC .......... *A61K 31/506* (2013.01); *A61K 31/426* (2013.01); *A61K 31/454* (2013.01); *A61K 31/519* (2013.01); *A61K 31/635* (2013.01); *A61K 31/7088* (2013.01); *A61K 45/06* (2013.01); *A61P 21/00* (2018.01); *G01N 2333/9121* (2013.01); *G01N 2500/04* (2013.01); *G01N 2800/2814* (2013.01); *G01N 2800/2835* (2013.01); *G01N 2800/2892* (2013.01)

(58) Field of Classification Search
CPC .. A61K 31/426; A61K 31/454; A61K 31/506; A61K 31/519; A61K 31/635; A61K 31/7088; A61P 21/00; G01N 2333/9121; G01N 2800/2814; G01N 2800/2835; G01N 2800/2892
See application file for complete search history.

(56) References Cited

U.S. PATENT DOCUMENTS

2002/0119963 A1    8/2002    Sanner

FOREIGN PATENT DOCUMENTS

| JP | 2004505111 | | 2/2004 |
| JP | 2005-524609 | | 8/2005 |
| JP | 2014047191 | | 3/2014 |
| JP | 2014047191 A | * | 3/2014 |
| WO | 2003/051886 A1 | | 6/2003 |
| WO | 2015/095840 | | 6/2015 |

OTHER PUBLICATIONS

Bosken et al (Nat Commun 5: 1-14, 2014).*
Lin et al (Mol Med Rep 6: 1293-1300, 2012).*
Katsuno et. al., JP-2014047191-A, publ. Mar. 17, 2014, English language translation (Year: 2014).*
Tan et. al., Experimental Neurology, vol. 235, pp. 469-475, publ. 2012 (Year: 2012).*
Udd et. al., Lancet Neurol., vol. 11, pp. 891-905, publ. 2012 (Year: 2012).*
Labbadia et. al., Trends in Biochemical Sci., vol. 38(8), pp. 378-385, publ. 2013 (Year: 2013).*
Zarei et. al., Surgical Neurol. Int., vol. 6, pp. 1-16, publ. 2015 (Year: 2015).*
Ketley et al., "CDK12 inhibition reduces abnormalities in cells from patients with myotonic dystrophy and in a mouse model" Science Translational Medicine, 12 eaaz2415 (2020).
Bergamini, Giovanna, et al. "A selective inhibitor reveals PI3K? dependence of TH 17 cell differentiation." Nature chemical biology 8.6 (2012): 576-582.
Christian A Bösken et al.: "The structure and substrate specificity of human Cdk12/Cyclin K", Nature Communications, vol. 5, Mar. 24, 2014 XP055377119, DOI: 10.1038/ncomms4505.
P. Paoletti et al: "Dopaminergic and Glutamatergic Signaling Crosstalk in Huntington's Disease Neurodegeneration: The Role of p25/Cyclin-Dependent Kinase 5", Journal of Neuroscience, vol. 28, No. 40, Oct. 1, 2008 (Oct. 1, 2008), pp. 10090-10101, XP055377409, US ISSN: 0270-6474, DOI: 10.1523/JNEUROSCI.3237-08.2008.
International Search Report for PCT/GB2017/050824 dated Apr. 8, 2017.
Written Opinion of the International Searching Authority for PCT/GB2017/050824, dated 2017.
International Preliminary Report on Patentability for International Application No. PCT/GB2017/050824,dated Sep. 25, 2018.
Bantscheff, Marcus, et al. "Chemoproteomics profiling of HDAC inhibitors reveals selective targeting of HDAC complexes." Nature biotechnology 29.3 (2011): 255.

(Continued)

*Primary Examiner* — Sarah Pihonak
(74) *Attorney, Agent, or Firm* — Baker Donelson

(57) ABSTRACT

The invention relates to inhibitors of CDK12 (cyclin-dependent kinase 12), and there use in the treatment or prevention of a disorder in a subject caused by the generation of repeat expansion transcripts.

Figure 1:
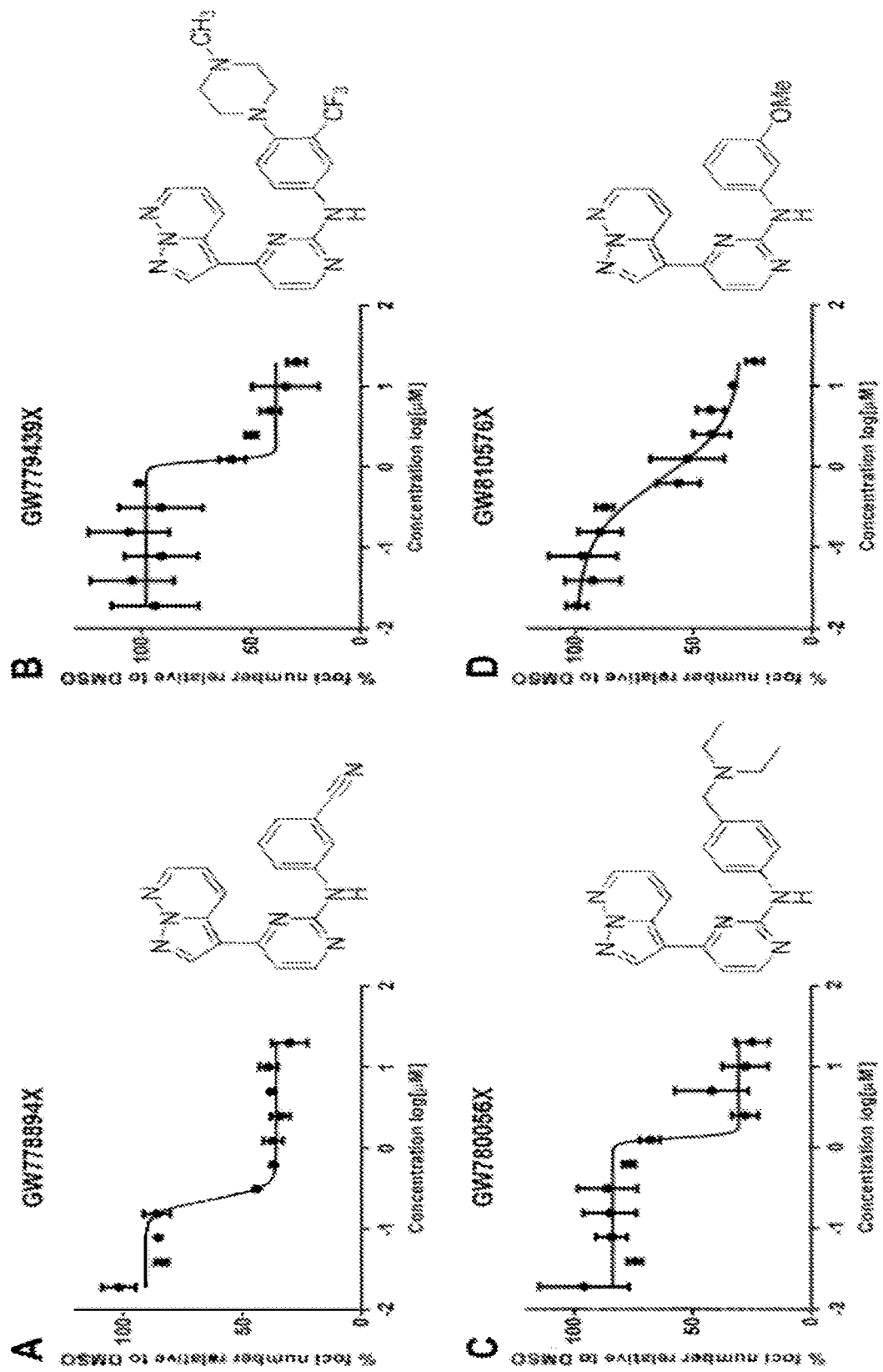

29 Claims, 32 Drawing Sheets
Specification includes a Sequence Listing.

(56) References Cited

OTHER PUBLICATIONS

Bantscheff, Marcus, et al. "Quantitative chemical proteomics reveals mechanisms of action of clinical ABL kinase inhibitors." Nature biotechnology 25.9 (2007): 1035-1044.
H Drewry, David, Timothy M Willson, and William J Zuercher. "Seeding collaborations to advance kinase science with the GSK Published Kinase Inhibitor Set (PKIS)." Current topics in medicinal chemistry 14.3 (2014): 340-342.
Hamshere, Marion G., et al. "Transcriptional abnormality in myotonic dystrophy affects DMPK but not neighboring genes." Proceedings of the National Academy of Sciences 94.14 (1997): 7394-7399.
Ketley, Ami, et al. "High-content screening identifies small molecules that remove nuclear foci, affect MBNL distribution and CELF1 protein levels via a PKC-independent pathway in myotonic dystrophy cell lines." Human molecular genetics 23.6 (2014): 1551-1562.
Ko, Tun K., Emma Kelly, and Jonathon Pines. "CrkRS: a novel conserved Cdc2-related protein kinase that colocalises with SC35 speckles." Journal of cell science 114.14 (2001): 2591-2603.
Kruse, U., et al. "Chemoproteomics-based kinome profiling and target deconvolution of clinical multi-kinase inhibitors in primary chronic lymphocytic leukemia cells." Leukemia 25.1 (2011): 89-100.
Langlois, Marc-André, et al. "Hammerhead ribozyme-mediated destruction of nuclear foci in myotonic dystrophy myoblasts." Molecular Therapy 7.5 (2003): 670-680.
Liang, Kaiwei, et al. "Characterization of human cyclin-dependent kinase 12 (CDK12) and CDK13 complexes in C-terminal domain phosphorylation, gene transcription, and RNA processing." Molecular and cellular biology 35.6 (2015): 928-938.
Mulders, Susan AM, et al. "Triplet-repeat oligonucleotide-mediated reversal of RNA toxicity in myotonic dystrophy." Proceedings of the National Academy of Sciences 106 33 (2009): 13915-13920.
Savitski, Mikhail M., et al. "Delayed fragmentation and optimized isolation width settings for improvement of protein identification and accuracy of isobaric mass tag quantification on Orbitrap-type mass spectrometers." Analytical chemistry 83.23 (2011): 8959-8967.
Savitski, Mikhail M., et al. "Measuring and managing ratio compression for accurate iTRAQ/TMT quantification." Journal of proteome research 12.8 (2013): 3586-3598.
Savitski, Mikhail M., et al. "Targeted data acquisition for improved reproducibility and robustness of proteomic mass spectrometry assays." Journal of the American Society for Mass Spectrometry 21.10 (2010): 1668-1679.
Stevens, Kirk L., et al. "Synthesis and evaluation of pyrazolo [1,5-b] pyridazines as selective cyclin dependent kinase inhibitors." Bioorganic & medicinal chemistry letters 18.21 (2008): 5758-5762.
Werner, Thilo, et al. "High-resolution enabled TMT 8-plexing." Analytical chemistry 84.16 (2012): 7188-7194.
Wheeler, Thurman M., et al. "Reversal of RNA dominance by displacement of protein sequestered on triplet repeat RNA." Science 325 5938 (2009): 336-339.
Wheeler, Thurman M., et al. "Targeting nuclear RNA for in vivo correction of myotonic dystrophy." Nature 488.7409 (2012): 111-115.
Johnson, S., et al.,CDK12 Inhibition Reverses De Novo and Acquired PARP Inhibitor Resistance in BRCA Wild-Type and Mutated Models of Triple-Negative Breast Cancer Cell Reports, vol. 17, Issue 9, 2016, pp. 2367-2381.

* cited by examiner

Figure 1 continued
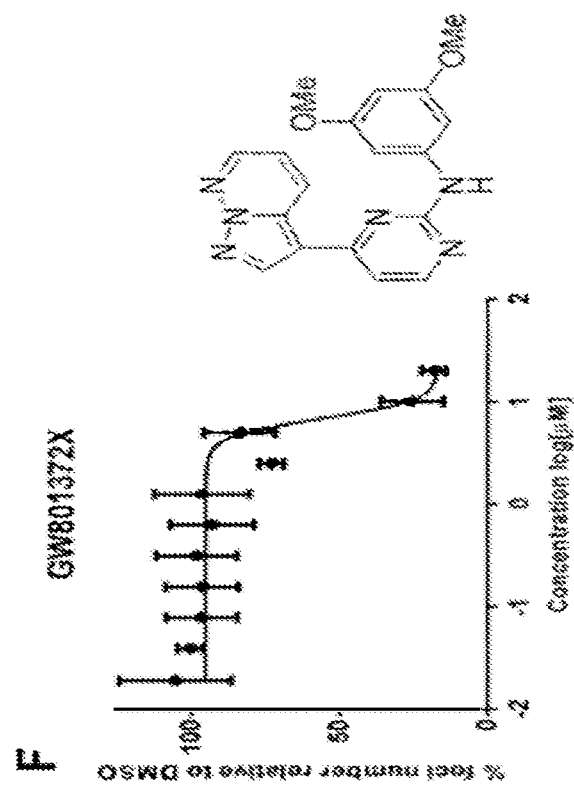
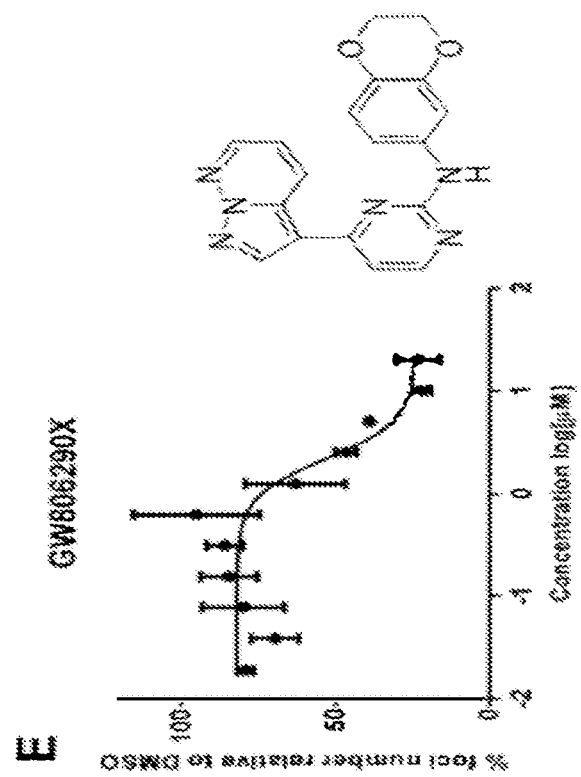

Figure 3:
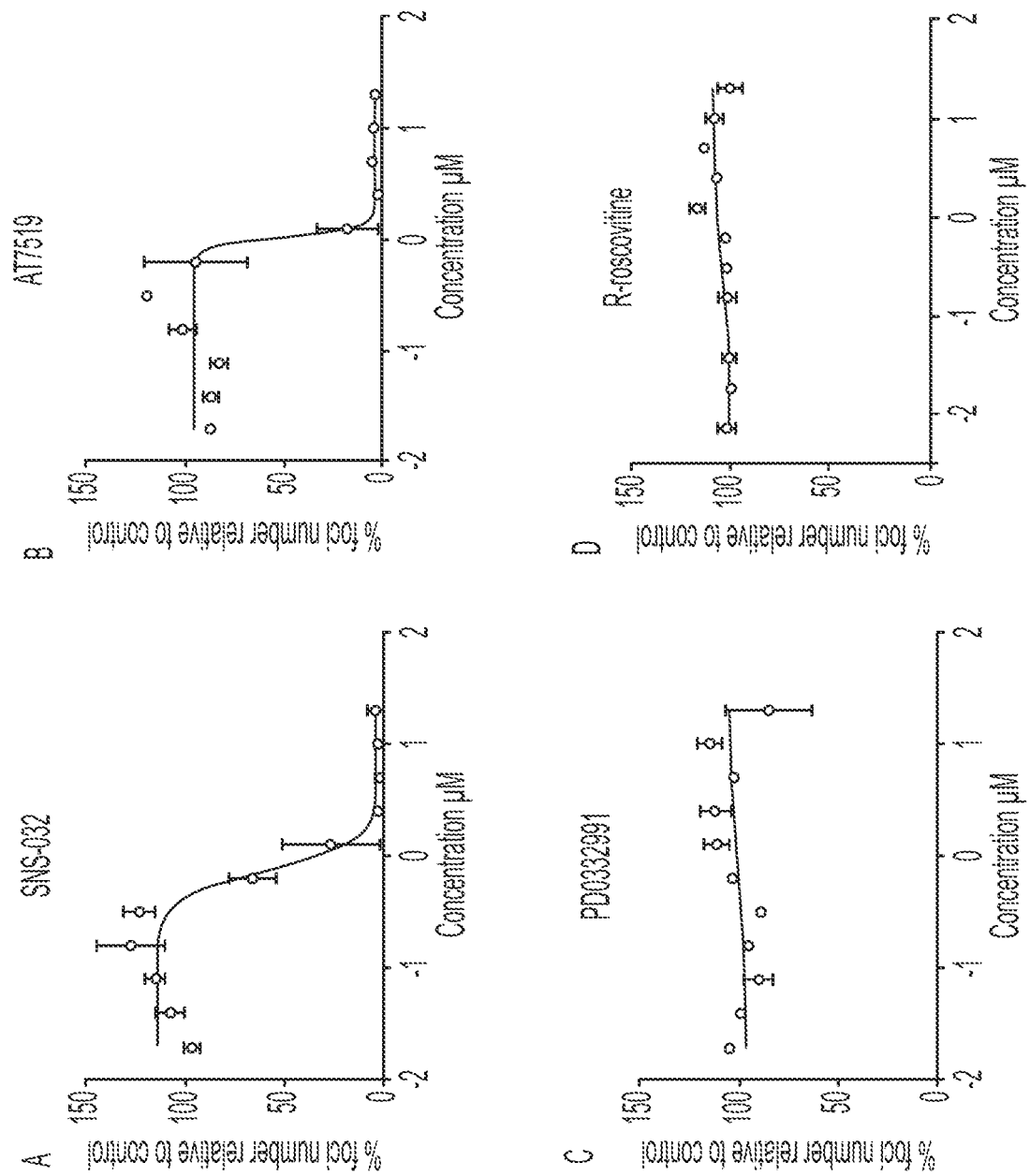

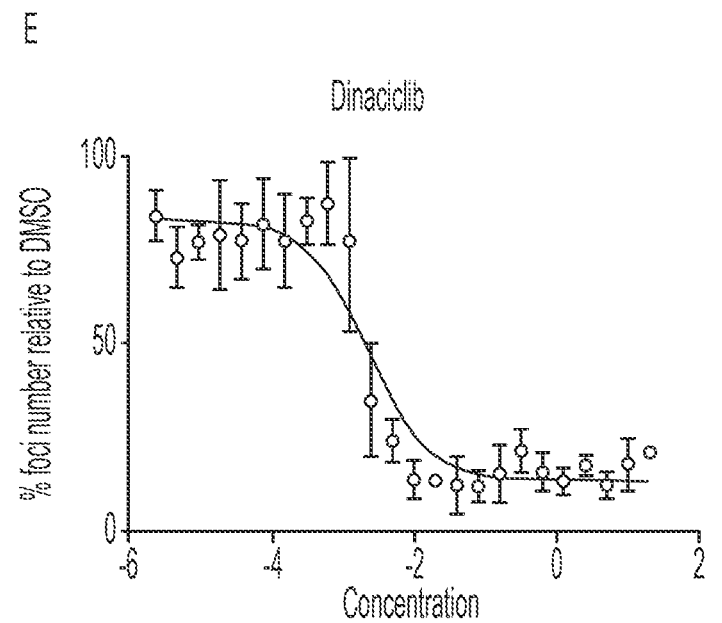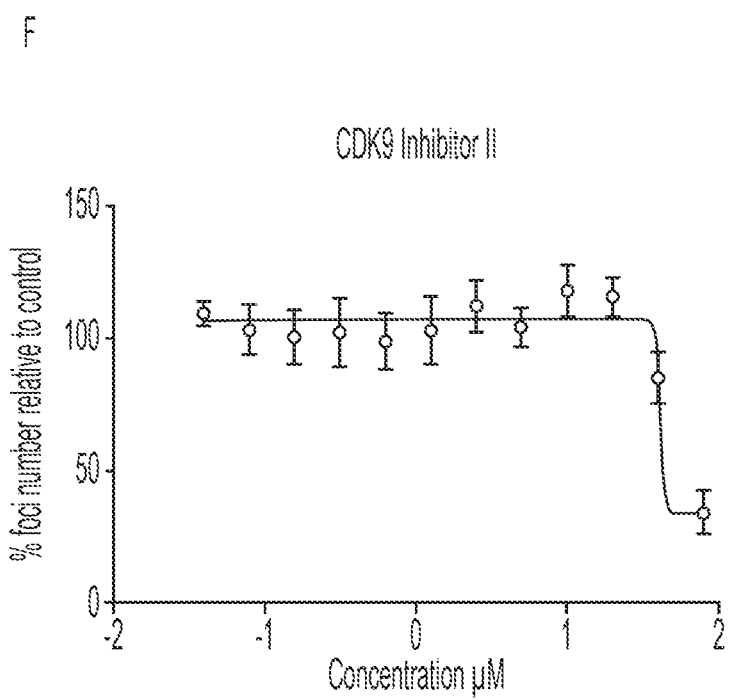
Figure 3 (cont.)

| Name | GSK3145107, Dinaciclib | GW780058 | GSK2136720, SNS-032 | GSK2136711, AT7519 | GW767488 | GW671732 | GW816745 | GSK2993735, PD0332991 | GW696155 | GW805758 | GW781673 |
|---|---|---|---|---|---|---|---|---|---|---|---|
| pIC50 foci assay | 8.7 | 6.3 | 6.1 | 6 | 5.3 | 5 | 4.5 | <4 | <4 | <4 | <4 |
| AAK1 | 1.05 | 0.17 | 0.95 | 0.98 | 0.09 | 0.45 | 0.97 | 0.76 | 0.1 | 0.84 | 0.89 |
| ACVR1 | 0.99 | 0.37 | 0.97 | 0.87 | 0.32 | 0.84 | 0.98 | 1.05 | 0.72 | 0.94 | 1.03 |
| AURKA | 1.03 | 0.8 | 0.88 | 0.97 | 0.92 | 0.91 | 0.97 | 0.99 | 0.5 | 0.86 | 0.98 |
| AURKB | 0.99 | 0.27 | 0.88 | 0.88 | 0.82 | 0.75 | 0.94 | 0.82 | 0.79 | 1.02 | 0.98 |
| BMP2K | 1.05 | 0.28 | 0.96 | 0.98 | 0.14 | 0.81 | 1.01 | 0.79 | 0.16 | 0.92 | 0.92 |
| CAMKK2 | 0.82 | 0.6 | 0.78 | 0.75 | 0.73 | 0.43 | 0.97 | 0.87 | 0.96 | 0.92 | 0.9 |
| CDC2 | 0.54 | 0.51 | 0.39 | 0.39 | 0.78 | 0.61 | 0.9 | 0.92 | 0.89 | 0.83 | 0.87 |
| CDK2 | 0.17 | 0.42 | 0.1 | 0.11 | 0.57 | 0.45 | 1.01 | 0.85 | 0.92 | 1.01 | 0.9 |
| CDK5 | 0.19 | 0.7 | 0.6 | 0.37 | 0.87 | 0.58 | 1 | 0.88 | 0.94 | 0.92 | 0.84 |
| CDK7 | 0.22 | 0.21 | 0.29 | 0.59 | 0.35 | 0.75 | 0.98 | 0.89 | 0.68 | 0.9 | 0.9 |
| CDK9 | 0.11 | 0.14 | 0.16 | 0.16 | 0.3 | 0.2 | 0.84 | 0.64 | 0.88 | 0.51 | 0.41 |
| CSNK1A1 | 0.96 | 0.2 | 0.81 | 0.99 | 0.67 | 0.52 | 0.95 | 1.02 | 0.99 | 0.9 | 0.73 |
| CSNK1D | 0.95 | 0.16 | 0.73 | 0.82 | 0.61 | 0.23 | 0.92 | 0.93 | 0.92 | 0.72 | 0.33 |
| CSNK1E | 0.9 | 0.33 | 0.89 | 1.07 | 0.71 | 0.44 | 1.07 | 0.99 | 0.92 | 0.82 | 0.67 |
| CSNK2A1 | 0.99 | 0.46 | 0.96 | 0.96 | 0.31 | 0.81 | 0.9 | 0.58 | 0.46 | 0.68 | 0.95 |
| CSNK2A2 | 1.02 | 0.24 | 0.9 | 0.93 | 0.09 | 0.54 | 1.02 | 0.24 | 0.11 | 0.87 | 0.98 |
| GAK | 1.01 | 0.59 | 0.92 | 0.98 | 0.19 | 0.87 | 1.05 | 0.98 | 0.31 | 1.04 | 1.01 |
| GSK3A | 0.95 | 0.6 | 0.34 | 0.09 | 0.99 | 1.01 | 1.03 | 1.14 | 1.07 | 0.86 | 1.1 |
| GSK3B | 0.96 | 0.66 | 0.55 | 0.21 | 1.07 | 1.03 | 0.93 | 1.09 | 1.12 | 0.88 | 1.06 |
| IKBKE | 1.07 | 0.99 | 1.02 | 1.06 | 0.83 | 0.95 | 1.03 | 1.01 | 0.5 | 0.81 | 0.99 |

Figure 9A

| Name | GSK3145107, Dinaciclib | GW780058 | GSK2136720, SNS-032 | GSK2136711, AT7519 | GW767488 | GW671732 | GW816745 | GSK2993735, PD0332991 | GW696155 | GW805758 | GW781673 |
|---|---|---|---|---|---|---|---|---|---|---|---|
| JAK1 | 0.95 | 0.59 | 0.99 | 0.95 | 0.44 | 0.93 | 0.98 | 1.02 | 0.77 | 0.84 | 0.98 |
| KIT | 0.97 | 0.16 | 0.1 | 0.91 | 0.75 | 0.85 | 1.1 | 0.94 | 0.92 | 0.54 | 0.96 |
| LIMK2 | 1.01 | 0.7 | 0.81 | 0.85 | 0.53 | 0.89 | 0.88 | 0.83 | 0.37 | 1.04 | 0.69 |
| MAPK8 | 0.99 | 0.34 | 1.02 | 0.97 | 0.38 | 0.56 | 0.97 | 0.92 | 0.31 | 0.92 | 0.99 |
| MAPK9 | 0.98 | 0.65 | 1.07 | 0.97 | 0.49 | 0.68 | 0.95 | 0.83 | 0.53 | 1.06 | 0.95 |
| MELK | 1.02 | 0.57 | 0.75 | 0.99 | 0.39 | 0.71 | 1 | 0.85 | 0.84 | 0.97 | 0.9 |
| NEK9 | 1.02 | 0.42 | 1 | 1.01 | 0.28 | 0.79 | 1 | 1.08 | 0.06 | 0.88 | 1.02 |
| PIK3C3 | 1.06 | 0.43 | 1 | 1.02 | 0.43 | 0.78 | 1.05 | 0.74 | 0.69 | 0.69 | 1.1 |
| PIK3R4 | 0.96 | 0.5 | 1.01 | 1.05 | 0.5 | 0.84 | 0.83 | 0.65 | 0.72 | 0.89 | 0.97 |
| PIP4K2A | 0.65 | 0.62 | 0.95 | 0.93 | 0.63 | 0.82 | 0.9 | 0.45 | 0.95 | 0.73 | 0.73 |
| PIP4K2C | 0.96 | 0.22 | 0.96 | 0.98 | 0.36 | 0.75 | 1.04 | 0.21 | 0.83 | 0.64 | 0.9 |
| PIP5K3 | 1 | 0.48 | 1.01 | 0.99 | 0.58 | 1 | 0.92 | 1.03 | 0.73 | 0.89 | 0.96 |
| PTK2 | 1.02 | 0.33 | 0.95 | 0.98 | 0.7 | 0.96 | 0.96 | 0.98 | 0.92 | 0.92 | 0.95 |
| RIOK2 | 0.98 | 0.49 | 0.91 | 1.01 | 0.43 | 0.53 | 1.03 | 1.07 | 0.94 | 0.77 | 0.77 |
| STK16 | 0.9 | 0.33 | 1.14 | 1.15 | 0.35 | 0.98 | 1.08 | 0.48 | 0.41 | 0.92 | 1.14 |
| TAOK2 | 0.9 | 0.88 | 0.84 | 0.32 | 0.75 | 0.68 | 0.9 | 0.82 | 0.7 | 1.03 | 0.94 |
| TAOK3 | 0.69 | 0.77 | 0.96 | 0.45 | 0.82 | 0.78 | 0.85 | 0.8 | 0.67 | 0.93 | 1.05 |
| TBK1 | 1.11 | 1.05 | 1.04 | 0.98 | 0.79 | 1.05 | 0.98 | 1.08 | 0.31 | 0.97 | 1 |
| TYK2 | 0.95 | 0.4 | 0.93 | 0.91 | 0.46 | 0.93 | 0.91 | 0.95 | 0.84 | 0.92 | 0.9 |
| ULK3 | 0.99 | 0.9 | 1.07 | 0.99 | 0.8 | 0.97 | 0.99 | 0.98 | 0.27 | 1.08 | 0.95 |

Figure 9A (cont.)

A

F

G.

Figure 12:
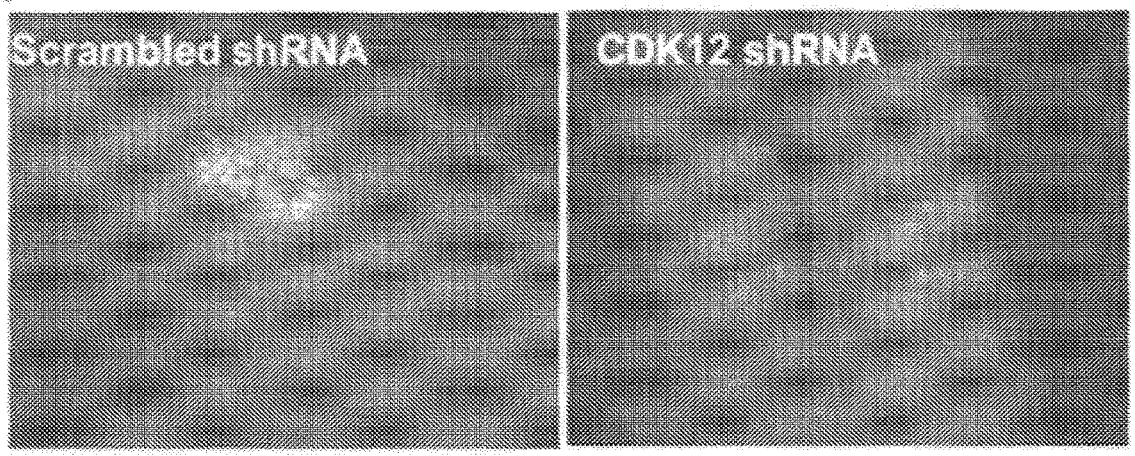
Figure 12:
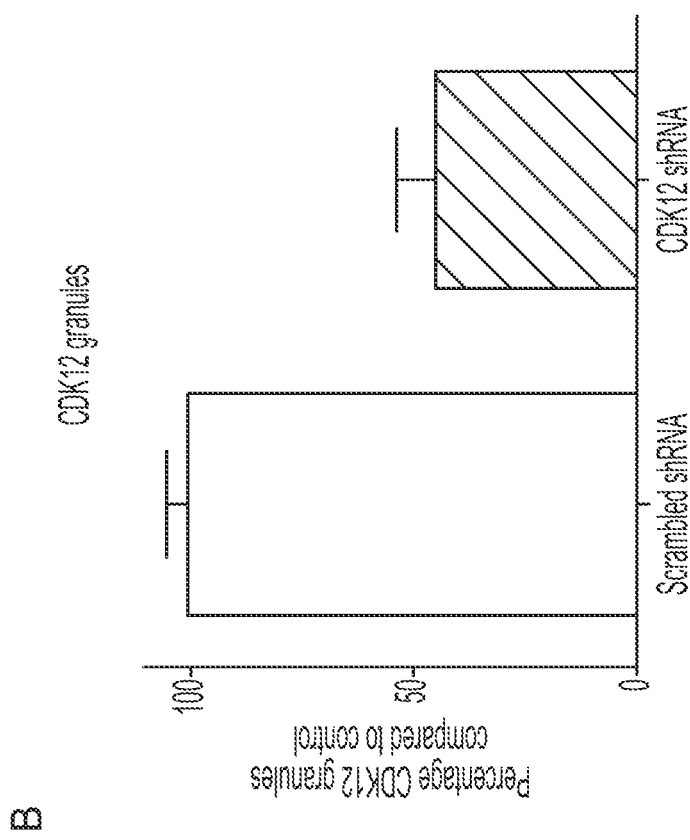
Figure 12:
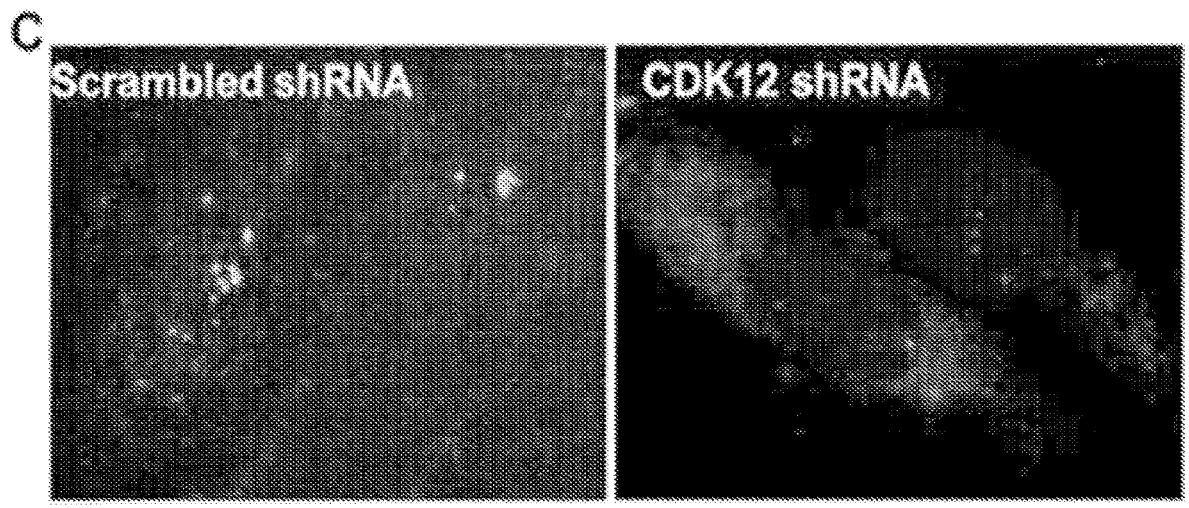
Figure 12:
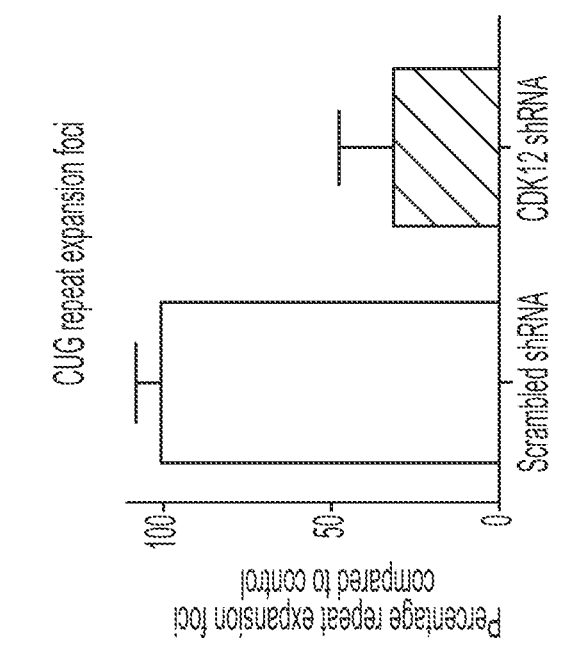
Figure 12:
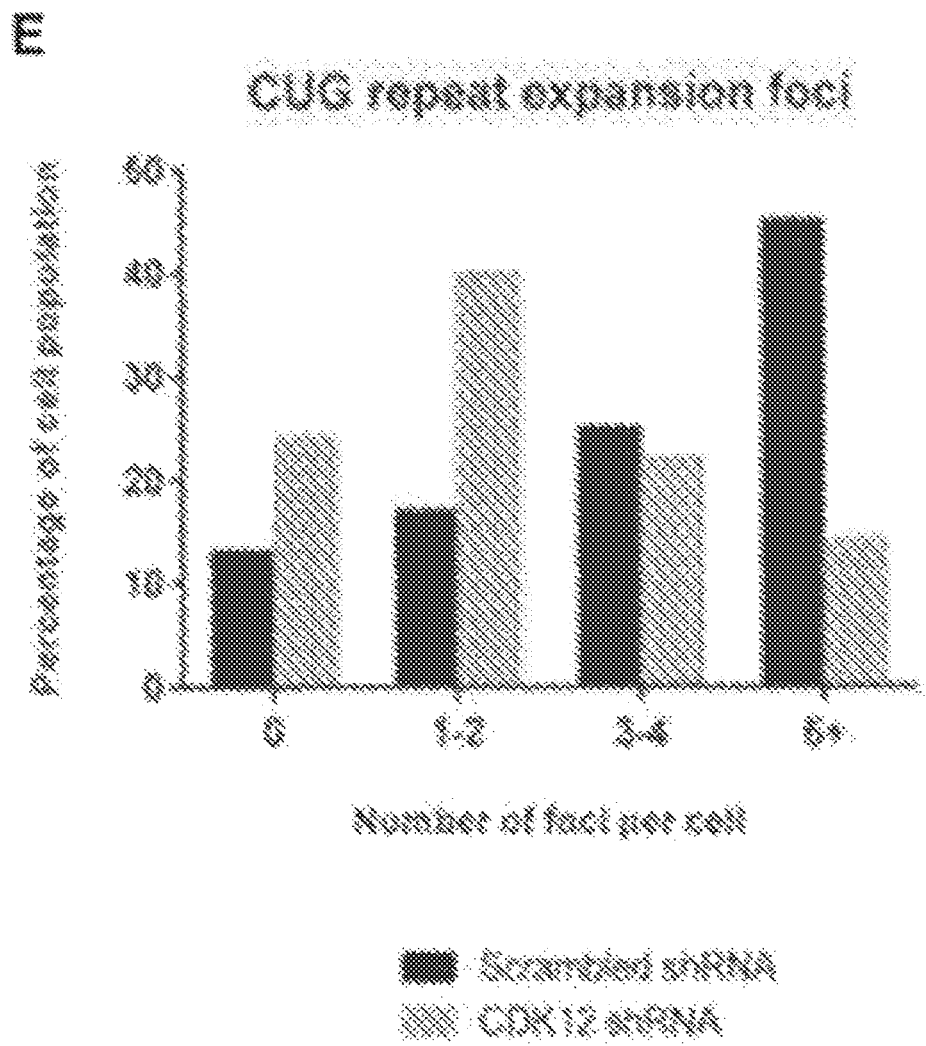
Figure 12:
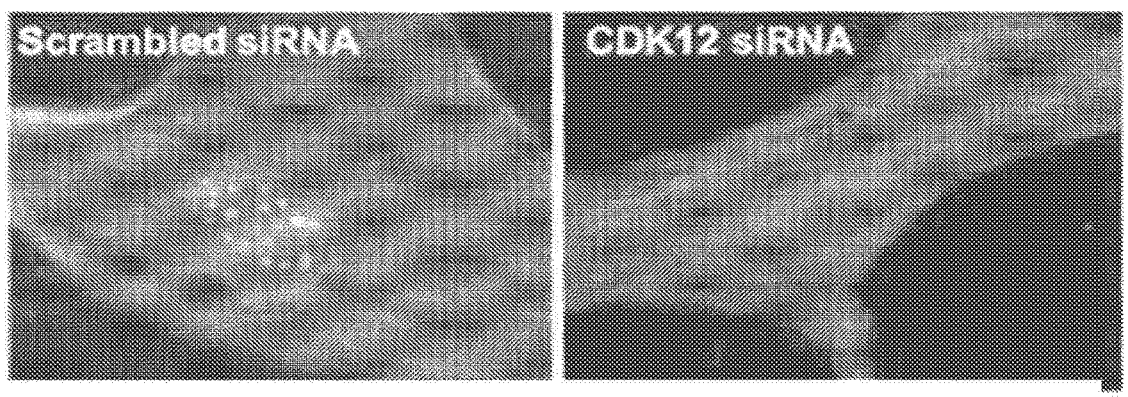
Figure 12:
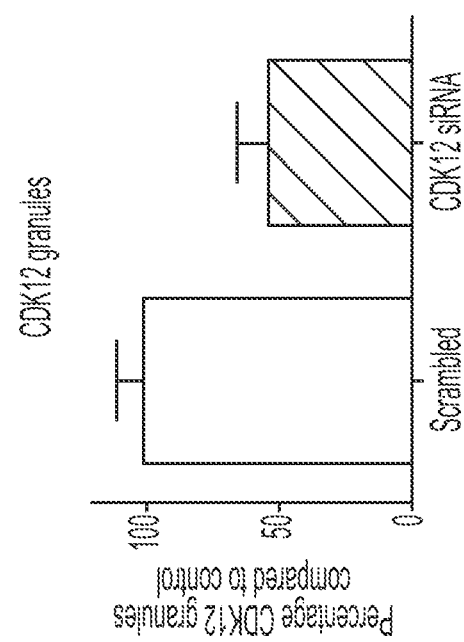
Figure 12:
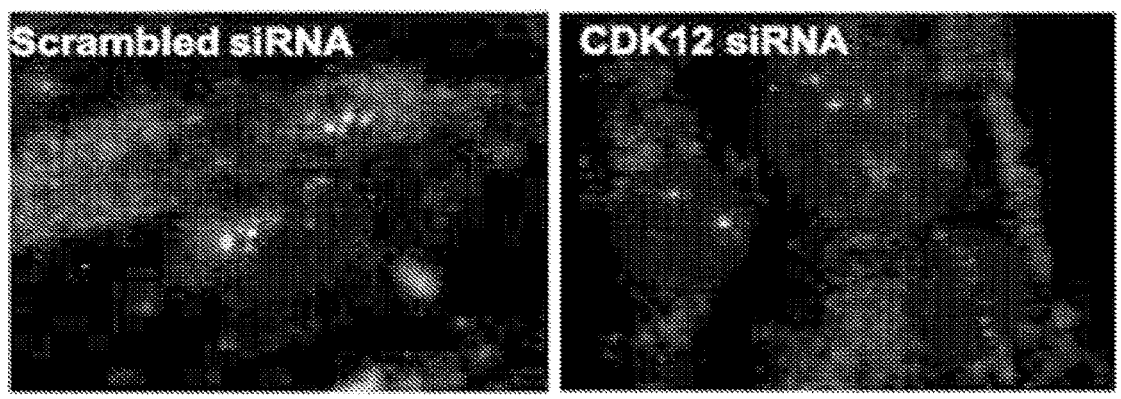
Figure 12:
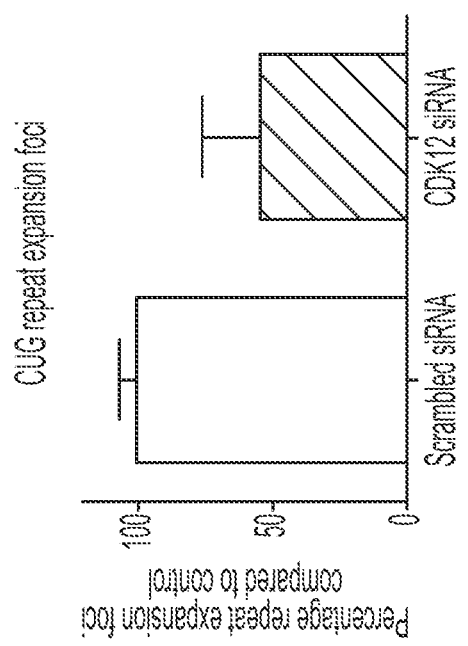
Figure 12:
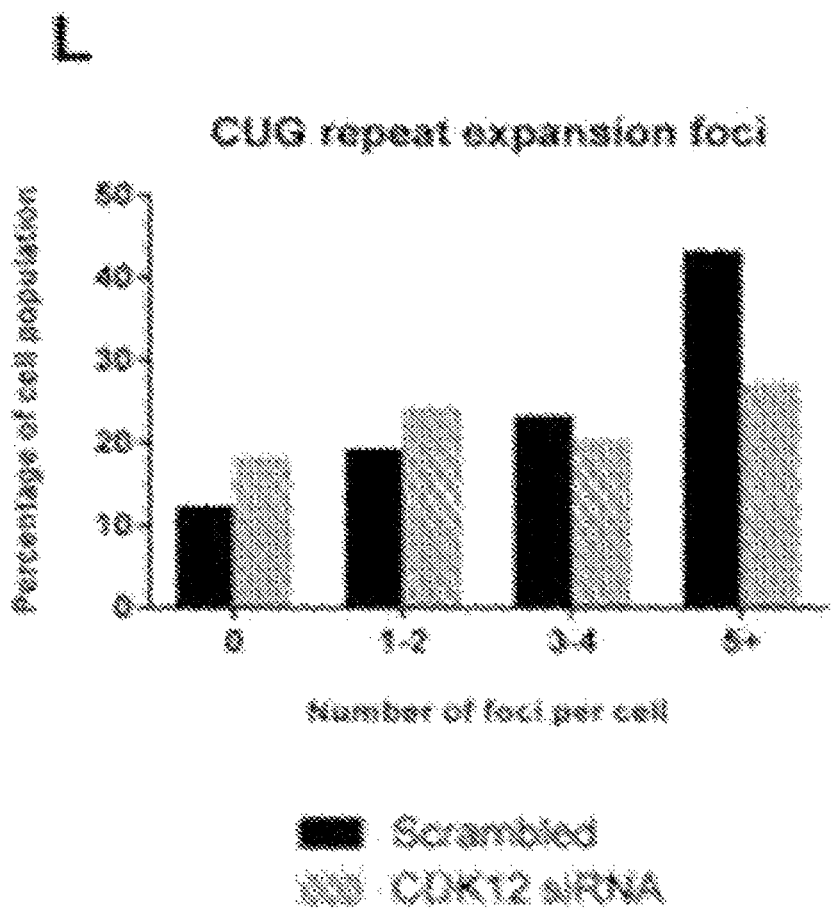

Figure 12 continued
H
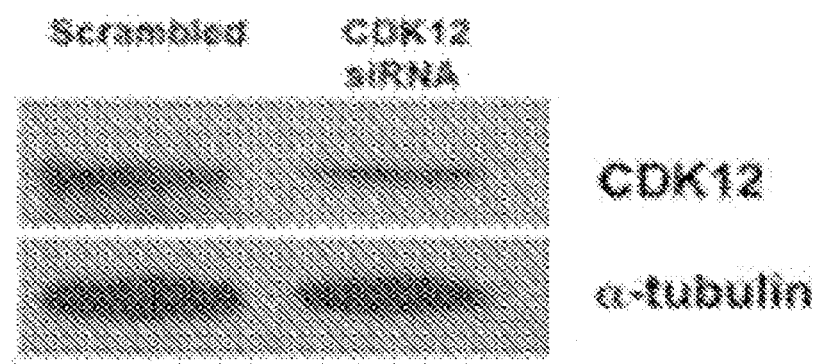
I
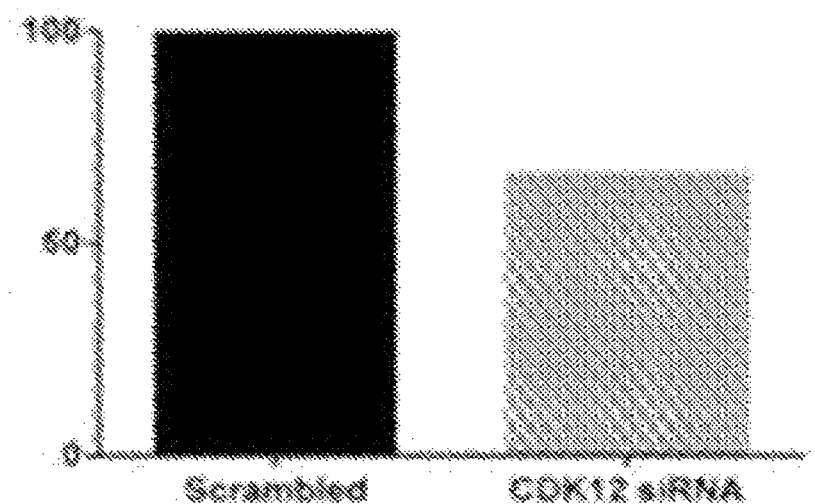

J

Figure 13

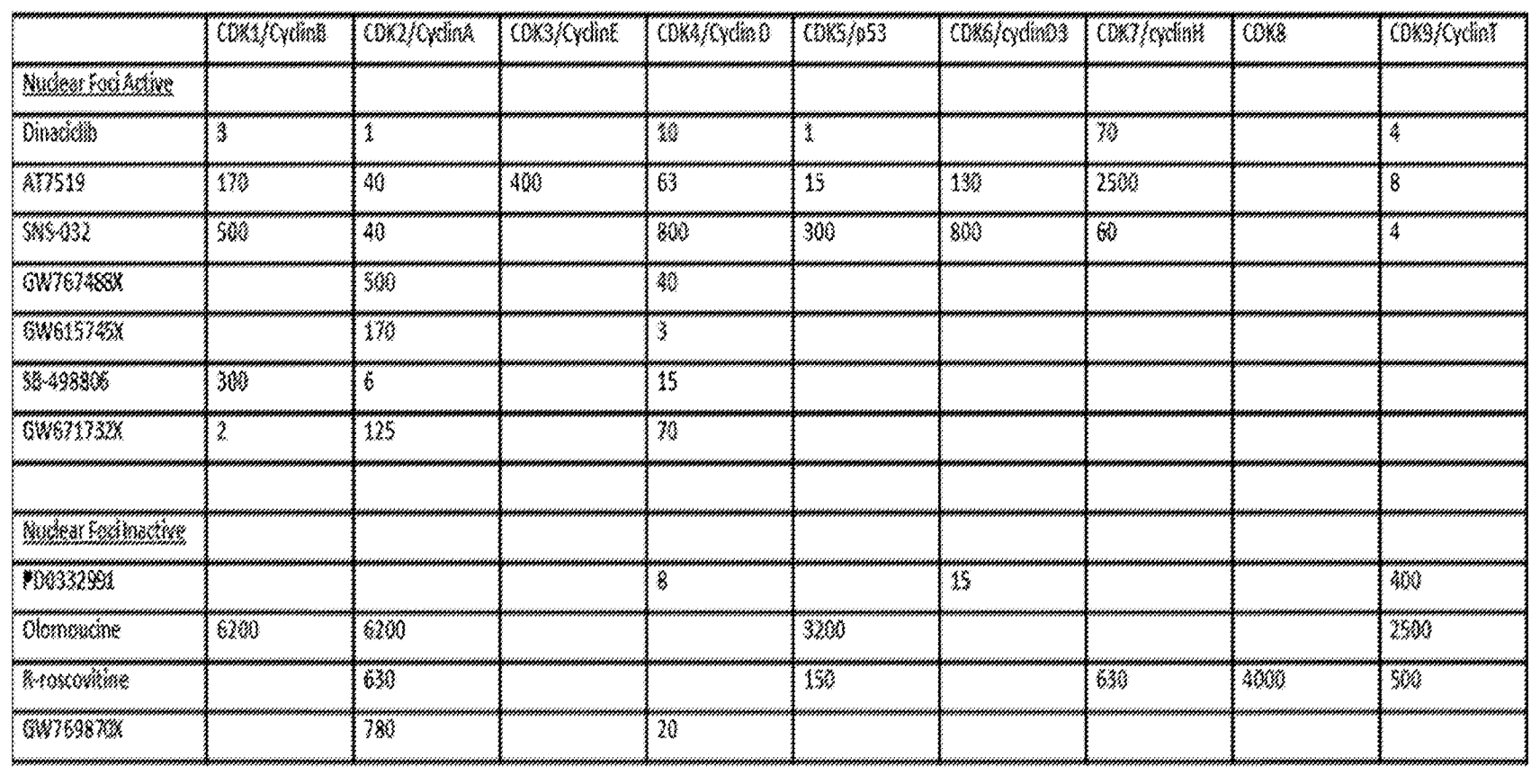

| | CDK1/CyclinB | CDK2/CyclinA | CDK3/CyclinE | CDK4/CyclinD | CDK5/p53 | CDK6/cyclinD3 | CDK7/cyclinH | CDK8 | CDK9/CyclinT |
|---|---|---|---|---|---|---|---|---|---|
| Nuclear Foci Active | | | | | | | | | |
| Dinaciclib | 3 | 1 | | 10 | 1 | | | | 4 |
| AT7519 | 170 | 40 | 400 | 63 | 15 | 130 | 70 | | 8 |
| SNS-032 | 500 | 40 | | 800 | 300 | 800 | 2500 | | 4 |
| GW782486X | | 500 | | 40 | | | 60 | | |
| GW615745X | | 170 | | 3 | | | | | |
| SB-498806 | 300 | 6 | | 15 | | | | | |
| GW621736X | 2 | 125 | | 70 | | | | | |
| Nuclear Foci Inactive | | | | | | | | | |
| PHA793991 | | | | 8 | 3200 | 15 | | | 400 |
| Olomoucine | 6200 | 6200 | | | | | | | 2500 |
| R-roscovitine | | 630 | | | 150 | | 630 | 4000 | 500 |
| GW769870X | | 780 | | 20 | | | | | |

Figure 14

| experiment identifier | cell line | compound | alias | pIC50 loci assay | CDK1 | CDK2 | CDK4 | CDK5 | CDK6 | CDK7 | CDK9 | CDK10 | CDK12 | CDK13 | PCTK1 | PCTK2 |
|---|---|---|---|---|---|---|---|---|---|---|---|---|---|---|---|---|
| X015283 | K562 | GSK3145107 | dinaciclib | 8.7 | 8.99 | 8.54 | 6.2 | 7.17 | 7.84 | 6.7 | 7.8 | 7.59 | 7.88 | | 8.39 | 8 |
| X015898 | K562 | GW780056 | | 6.3 | <5 | 6.06 | 5.21 | 6.15 | 6.72 | 6.4 | 7.62 | 6.6 | 6.92 | 5.77 | 6.62 | 6.54 |
| X015795 | A204 | GW780056 | | 6.3 | <5 | 5.73 | 5.72 | 6.05 | | 5.82 | 7.8 | 6.3 | 6.24 | | 7.30 | 6.81 |
| X015510 | K562 | GSN213873730 | SNS-032 | 8.1 | 8.78 | 5.97 | 6.5 | 6.6 | 6.35 | 6.48 | 6.6 | 6.09 | 6.4 | 6.36 | 7 | 6.96 |
| X015851 | K562 | GW787488 | | 6.3 | <5 | 5.44 | 6.85 | 5.04 | 5.88 | 6.31 | 6.12 | 6.42 | 5.28 | 5.02 | 6.89 | 6.42 |
| X015862 | K562 | GW787488 | | 6.3 | <5 | 6.2 | 6.27 | <5 | 5.88 | 6.02 | 6.83 | 6.22 | <5 | <5 | 6.49 | 6.34 |
| X015708 | K562 | GW771732 | | 5 | <5 | <5 | 5.06 | 5.90 | 6.08 | <5 | 5.77 | 5.03 | <5 | <5 | 6.25 | 5.07 |
| X015818 | A204 | GW671732 | | 5 | <5 | 5.50 | <5 | 6.03 | 5.64 | 5.73 | 6.03 | 6.92 | <5 | <5 | 5.43 | 5.53 |
| X015867 | K562 | GW615745 | | 4.5 | <5 | <5 | 6.25 | <5 | 7.17 | <5 | 5.82 | <5 | <5 | <5 | 6.02 | 5.19 |
| X015736 | K562 | GSK2109872A | PD0332991 | <4 | <5 | <5 | <5 | <5 | | <5 | <5 | <5 | <5 | <5 | 5.82 | 5.82 |
| X015013 | K562 | GW695555 | | <4 | <5 | <5 | <5 | <5 | <5 | 5.21 | <5 | <5 | <5 | <5 | 5.02 | 5.48 | pIC50 values from SNS5752 Kinobeads profiling in K562 and A204 extract

CDK12 INHIBITORS AND THEIR USES

SEQUENCE LISTING

The instant application contains a Sequence Listing which has been submitted electronically in ASCII format and is hereby incorporated by reference in its entirety. Said ASCII copy, created on Jan. 6, 2020, is named 76890US-seq-listing-06012020.TXT and is 25,124 bytes in size.

The present invention relates to inhibitors of cyclin-dependent kinase 12 (CDK12) and in particular, inhibitors of CDK12 for use in the treatment of disorders caused by the generation of RNA repeat expansion transcripts. The RNA repeat expansion transcript may be from a CTG DNA repeat expansion such as seen in Myotonic Dystrophy.

Myotonic Dystrophy, also referred to herein as DM, is the most common form of adult muscular dystrophy. DM type 1 (DM1) affects 1 in 8,000 people and is caused by a CTG repeat sequence in the 3' untranslated region of the DMPK (dystrophia myotonica protein kinase) gene, which is greatly expanded in patients who may have anything from 50 repeats to several thousand on affected chromosomes compared to between 5 and 37 repeats on wild-type chromosomes. The expanded DNA repeat is transcribed, and despite being correctly spliced the RNA repeat expansion transcripts remain sequestered in the nucleus forming distinct foci. These foci interact with cellular proteins, such as MBNL1 (muscleblind-like splicing regulator 1), a key splicing regulator, which in turn leads to downstream splicing abnormalities. In addition to the sequestration of proteins the mutant RNA causes activation of CELF1 (CUGBP, Elav-like family member 1), which is also implicated in splicing. Additional molecular pathways are thought to be affected by the toxic RNA, including inhibition of translation.

DM is an inherited and progressive autosomal dominant multisystem disorder and symptoms can be highly variable. Typical features include myotonia, muscle weakness, cardiac arrhythmias, cognitive dysfunction, diabetes and cataracts. There is currently no treatment for DM and clinical management relies on a fragmented approach utilising already marketed drugs to treat specific symptoms of the disorder, such as mexiletine to treat myotonia and modafinal to address daytime sleepiness. However, due to the complex and variable nature of the disorder, treatment of individual symptoms is not an efficient way to manage the condition.

Key components of the DM molecular pathway have been identified but how these factors interact is still unclear. Recently there has been considerable effort towards therapeutic treatments for this condition including targeting different points of the molecular pathway with varying levels of success. The most obvious approach is to directly target the repeat expansion transcript to neutralize the harmful repeats or promote transcript degradation and subsequent clearance from the cell. To date this has been attempted using either ribozymes or antisense oligonucleotides (Langlois, M. A. et al. (2003). *Molecular therapy: the journal of the American Society of Gene Therapy*, 7: 670-680; Wheeler, T. M. et al. Nature, 488: 111-115; and Mulders, S. A. et al. (2009). *Proc Natl Acad Sci USA*, 106: 13915-13920). Other methods to target the repeat sequence directly have involved the introduction of a blocking molecule, such as morpholino oligonucleotides or small molecules that physically prevent binding of MBNL protein by sitting in the groove of the RNA and preventing protein association and binding (Wheeler, T. M. et al. (2009). *Science*, 325: 336-339). A series of compounds have been shown to successfully disrupt the CUG repeat:MBNL protein interaction including pentamidine, a bisamidinium inhibitor, a series of peptide ligands and two natural products, lomofugin and dilomofungin. Treatment of DM1-model-CUG-repeat cells with these compounds led to a loss of nuclear foci and a reversal of DM associated splicing events, consistent with release of MBNL protein from this complex. These compounds show that disruption of the RNA:protein interaction may be an option for therapeutic development. However these compounds do not represent suitable starting points for drug development due to high levels of toxicity, poor oral availability and, in the case of peptide ligands, instability in serum. To date there is no suitable treatment for DM.

An object of the present invention is to provide an alternative, preferably an improved, treatment and compound useful for treating disorder caused by the generation of repeat expansion transcripts, such as CTG repeat expansion transcripts as seen in DM-1, with an aim to address at least one of the aforementioned disadvantages.

According to a first aspect of the invention, there is provided an inhibitor for use in the treatment or prevention of a disorder in a subject caused by the generation of repeat expansion transcripts, wherein the inhibitor is an inhibitor of CDK12 (cyclin-dependent kinase 12).

The repeat expansion transcript may result in the transcript being retained in the nucleus. In one embodiment, the term "retained in the nucleus" may refer to no detectable repeat expansion transcript leaving the nucleus. In another embodiment, the term may refer to a delay in the transcript leaving the nucleus (i.e. a transient retention in the nucleus).

The disorder may comprise any disorder associated with RNA repeat expansion transcripts, such as transcripts from CTG DNA repeat expansions, where the mutant transcripts do not get exported from the nucleus. The disorder may be any disorder selected from the group comprising Myotonic Dystrophy type 1 ($CTG_n$), Myotonic Dystrophy type 2 ($CCTG_n$), Fragile X associated tremor/ataxia syndrome ($CGG_n$), and amylotrophic lateral sclerosis (ALS) and frontotemporal dementia (C9ORF72) ($GGGGCC_n$) each of which shows or may show nuclear retention of transcripts from repeat DNA expansions. The disorder may be any disorder selected from the group comprising Spinocerebellar Ataxia Type 8 ($CTG_n$), Spinocerebellar Ataxia Type 10 ($ATTCT_n$) and Spinocerebellar Ataxia Type 31 ($TGGAA_n$) which may show nuclear retention. The disorder may be any disorder selected from the group comprising Huntington's Disease like 2 ($CTG_n$), and Huntington's Disease, Spinocerebellar Ataxia Types 1, 2, 3, 6, 7, 17, Dentatorubral-pallidoluysian atrophy and Spinal and Bulbar Muscular Atrophy (which are associated with ($CAG_n$) repeat expansions, but which may show nuclear retention of transcripts with repeat expansions at the longest end of the disease range. The disorder may comprise any one or more disorders provided in Table 1.

TABLE 1

| DISEASE | ASSOCIATED GENE/ORF | GENBANK ACCESSION NUMBER |
| --- | --- | --- |
| Myotonic Dystrophy type 1 ($CTG_n$), | DMPK | NM_001081563 VERSION NM_001081563.2 GI: 571026697 |
| Myotonic Dystrophy type 2 ($CCTG_n$), | ZNF9 | AY329622 AF389886 AF389887 AH010982 VERSION AY329622.1 GI: 40738012 |

TABLE 1-continued

| DISEASE | ASSOCIATED GENE/ORF | GENBANK ACCESSION NUMBER |
|---|---|---|
| Fragile X associated tremor/ataxia syndrome (CGG$_n$), | FMR1 | L19493 VERSION L19493.1 GI: 388753 |
| Amylotrophic lateral sclerosis (ALS) and frontotemporal dementia (C9ORF72) (GGGGCC$_n$) | C9ORF72 | JN681271 VERSION JN681271.1 GI: 356892155 |
| Spinocerebellar Ataxia Type 8 (CTG$_n$) | SCA8 | AF126749 VERSION AF126749.1 GI: 4589125 |
| Spinocerebellar Ataxia Type 10 (ATTCT$_n$) | SCA10 | NM_013236 VERSION NM_013236.3 GI: 266453258 |
| Huntington's Disease like 2 (CTG$_n$) | Junctophilin3 | NM_001271604 VERSION NM_001271604.2 GI: 413082123 |
| Huntington's Disease | Huntingtin | NM_002111 VERSION NM_002111.7 GI: 588282786 |
| Spinocerebellar Ataxia Type 1 | Ataxin1 | NM_000332 VERSION NM_000332.3 GI: 189491746 |
| Spinocerebellar Ataxia Type 2 | Ataxin2 | NM_002973 VERSION NM_002973.3 GI: 171543894 |
| Spinocerebellar Ataxia Type 3 | Ataxin3 | NM_004993 VERSION NM_004993.5 GI: 189163490 |
| Spinocerebellar Ataxia Type 6 | CACNA1$_A$ | NM_000068 VERSION NM_000068.3 GI: 148536843 |
| Spinocerebellar Ataxia Type 7 | Ataxin 7 | NM_000333 VERSION NM_000333.3 GI: 189491740 |
| Spinocerebellar Ataxia Type 17 | Tata box binding protein | CR456776 VERSION CR456776.1 GI: 48145668 |
| Dentatorubral-pallidoluysian atrophy | Atrophin | D31840 VERSION D31840.1 GI: 862329 |
| Spinal and Bulbar Muscular Atrophy | Androgen receptor | M34233 VERSION M34233.1 GI: 179033 |
| Spinocerebellar Ataxia Type 31 | BEAN1 | NM_001178020 |

In one embodiment, the repeat expansion transcript may comprise RNA from a CTG repeat (i.e. the RNA may comprise a CUG repeat sequence). In another embodiment, the repeat expansion transcript may comprise RNA from a CCTG repeat (i.e. the RNA may comprise a CCUG repeat sequence). In another embodiment, the repeat expansion transcript may comprise RNA from a CGG repeat. In another embodiment, the repeat expansion transcript may comprise RNA from a GGGGCC repeat. In another embodiment, the repeat expansion transcript may comprise RNA from a ATTCT repeat (i.e. the RNA may comprise a AUUCU repeat sequence). In another embodiment, the repeat expansion transcript may comprise RNA from a CAG repeat. In another embodiment, the repeat expansion transcript may comprise RNA from TGGAA repeat (i.e. the RNA may comprise a UGGAA repeat sequence).

CDK12 is a transcription elongation associated C-terminal repeat domain kinase, which has shown to associate with elongating transcripts, rather than being involved in the initiation of transcription. The invention herein has found that inhibition of CDK12 results in the removal of nuclear foci from DM cells. Further advantageously, as CDK12 is not required at the start of transcription and its inhibition does not result in global transcriptional arrest, it is suitable as a target for long term DM treatment, and other disorders caused by the generation of repeat expansion transcripts, such as transcripts from CTG repeat expansions.

The term "inhibit" or "inhibition" used in the context of CDK12 herein is understood to mean a reduction or complete elimination of CDK12 activity. The reduction in activity of CDK12 may be 100%. Alternatively, the reduction in activity of CDK12 may be at least 90%. The reduction in activity of CDK12 may be at least 80%. The reduction in activity of CDK12 may be at least 70%. The reduction in activity of CDK12 may be at least 60%. In some embodiments, the CDK12 inhibition may be measured by an assay measuring any inhibition of CDK12 consumption of ATP during the phosphorylation of a substrate peptide in the presence of the molecule to be screened.

The CDK12 inhibition may involve blocking the CDK12 active site directly or indirectly; changing the conformation of CDK12; blocking CDK12 interactions; preventing cyclin k binding; preventing phosphorylation of Ser2 on the C-terminal domain of RNA polymerase II; reducing the presence of CDK12; or sequestering the CDK12, for example through aggregation.

The inhibition of CDK12 activity may be by reduction in the presence of CDK12 (i.e. the activity of CDK12 itself may not be inhibited, but the amount of active CDK12 available in the cells and tissue may be reduced). Therefore, in some embodiments, the inhibition of CDK12 may be provided by reducing the expression of CDK12. Alternatively, CDK12 may be mutated to an inactive form. Alternatively, CDK12 may be targeted for degradation or sequestration to reduce the amount of active CDK12 available in the cells or tissue. The reduction in amount of CDK12 may be 100%. Alternatively, the reduction in amount of CDK12 may be at least 90%. The reduction in amount of CDK12 may be at least 80%. The reduction in amount of CDK12 may be at least 70%. The reduction in amount of CDK12 may be at least 60%. The inhibition of CDK12 activity by reduction in the presence of CDK12 may be measured by RT-PCR of CDK12 transcripts in a sample, or by western blot. The skilled person would understand that there are several methods that may be used to determine the presence and level of any particular protein, or transcripts thereof, in a sample.

The term "inhibitor" used herein is understood to include an agent, such as a molecule, that it capable of causing the inhibition of CDK12 activity. Additionally, or alternatively, the term "inhibitor" used herein is understood to include an agent, such as a molecule, that it capable of causing the inhibition of CDK12 availability.

The inhibitor may be specific for CDK12. For example, the inhibitor may not inhibit, or not substantially inhibit other cyclin-dependent kinases. Alternatively, the activity of one or more other cyclin-dependent kinases may be inhibited by the inhibitor, but similar to or less than the activity of CDK12. Alternatively, the activity of one or more other cyclin-dependent kinases may be inhibited by the inhibitor, but significantly less than the activity of CDK12. In one embodiment, the inhibitor is not an inhibitor of CDK9 activity or availability. The other CDKs that may not be inhibited, or not significantly inhibited, may be selected from the group consisting of CDK1, CDK2, CDK3, CDK4, CDK5, CDK6, CDK7, CDK8, CDK9, CDK10, CDK11, and CDK13; or combinations thereof. The other CDKs that may not be inhibited, or not significantly inhibited, may be selected from the group comprising CDK1, CDK2, CDK5, and CDK9; or combinations thereof. Preferably CDK9 is not inhibited, or is not significantly inhibited by an inhibitor of the invention.

The inhibitor may comprise an inhibitor of CDK12 expression. The inhibitor may comprise an oligonucleotide, such as siRNA, capable of inhibiting CDK12 expression. The oligonucleotide may comprise a sequence capable of binding to nucleic acid of the CDK12 gene, or regulatory elements thereof, or a mRNA transcript thereof. The oligonucleotide may comprise a sequence substantially complementary to the CDK12 gene, or regulatory elements thereof. The oligonucleotide may comprise a sequence substantially complementary to CDK12 mRNA transcript. The sequence may be substantially complementary over a region of at least 5 nucleotides. The sequence may be substantially complementary over a region of at least 8 nucleotides. The sequence may be substantially complementary over a region of at least 10, 13, 15, or 18 nucleotides. The oligonucleotide may comprise a sequence capable of binding to SEQ ID NO: 1, and reducing translation thereof, e.g. siRNA gene silencing.

The inhibitor may comprise a molecule capable of binding to CDK12. The inhibitor molecule may be capable of blocking binding of CDK12 to its target molecule. The inhibitor may comprise a molecule capable of preventing CDK12 binding to cyclin K. The inhibitor may comprise a molecule capable of preventing CDK12 phosphorylating Ser2 on the c-terminal domain of RNA polymerase II. The binding of the inhibitor to CDK12 may be at, or adjacent to, the CDK12 active site, such that the active site is blocked. The binding of the inhibitor to CDK12 may be at amino acid position, 727-1020 (underlined in the sequence below). The binding of the inhibitor to CDK12 may be at a C terminal domain extension that extends around the N and C terminal lobes and contacts bound ATP (C terminal domain extension comprises residues 1011-1039 of CDK12). Such a domain is unique to CDK12 and is not present in CDK9. The binding of the inhibitor to CDK12 may be at any one or more of the ATP contact residues selected from Thr737, Lys756, Glu814, Met816 and Asp819 (in bold-type on the sequence below).

CDK12 binds to cyclin K and phosphorylates Ser2 on the C-terminal domain of RNA polymerase II. Advantageously, the inhibitor treatment will result in a shift in the relative proportions of wild type and mutant DMPK transcripts (CDK12 inhibition leads to a preferential loss of the expanded repeat transcript).

The inhibitor may comprise a therapeutically active agent. The inhibitor may comprise a small molecule. The term "small molecule" means any compound that has a molecular weight of less than 1 kDa. The inhibitor may be an organic compound with a molecular weight of less than 1 KDa. Molecular weight is understood to be the sum of the atomic weights of all the atoms in a molecule.

The inhibitor may comprise nucleic acid such as an oligonucleotide. The oligonucleotide may comprise DNA, RNA, or synthetic nucleic analogues such as PMO, LNA or PNA. The oligonucleotide may comprise siRNA or microRNA. The oligonucleotide may comprise the sequence of CGAAAUAAUGAUGUUGGCACCAGUU (SEQ ID NO: 6), or a variant thereof, for siRNA silencing of CDK12.

The inhibitor may comprise a peptide or protein capable of binding to CDK12. The inhibitor may comprise an antibody, or an antibody fragment, or antibody mimetic.

The inhibitor may be cell membrane permeable.

The inhibitor may comprise a pyrazolo[1,5b]pyridazine core structure, and be capable of inhibiting CDK12 activity.

In one embodiment, the inhibitor comprises a compound of Formula (I) or a pharmaceutically acceptable salt or solvate thereof:

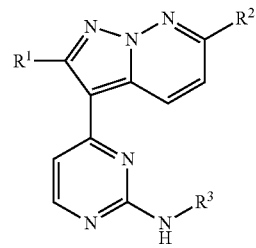

Formula I wherein:
R$^1$ is H, —OH, —O—, C$_{1-6}$alkyl, C$_{2-6}$alkenyl, C$_{2-6}$alkynl, C$_{1-6}$haloalkyl, halogen, —CN, —OC$_{1-6}$alkyl;

R$^2$ is H, —OH, —O—, C$_{1-6}$alkyl, C$_{2-6}$alkenyl, C$_{2-6}$alkynl, C$_{1-6}$haloalkyl, halogen, —CN, —OC$_{1-6}$alkyl or a five or 6 membered cycloaryl, cycloalkyl or heterocycl having one, two or three heteroatoms selected from O, S and N, for example benzene, morpholinyl, piperidine, piperazine;

R$^3$ is C$_{3-6}$cycloalkyl, for example cyclopropyl,

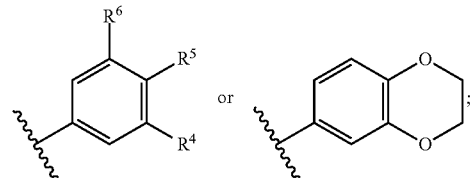

wherein:
R$^4$ is H, —OH, —O—, C$_{2-6}$alkenyl, C$_{2-6}$alkynl, C$_{1-6}$haloalkyl, halogen, —CN, —OC$_{1-6}$alkyl;

R$^5$ is H; —OH; —O—; C$_{1-6}$alkyl; C$_{2-6}$alkenyl; C$_{2-6}$alkynl; C$_{1-6}$haloalkyl; halogen; —CN; —OC$_{1-6}$alkyl; C$_{1-6}$alkyl-N—(X)(Y); a five or six membered cycloaryl, cycloalkyl or heterocycl having one, two or three heteroatoms selected from O, S and N and said cycloaryl, cycloalkyl or heterocycle being optionally substituted with a C$_{1-3}$alkyl, for example N-methylpiperazinyl; or —OC$_{1-6}$alkyl-N(X)(Y);

wherein X is H or C$_{1-6}$alkyl, and Y is H or C$_{1-6}$alkyl;

and wherein the alkyl groups are optionally substituted by one or more —OH groups; and R$^6$ is H, —OH, —O—, C$_{1-6}$ alkyl, C$_{2-6}$alkenyl, C$_{2-6}$alkynl, C$_{1-6}$haloalkyl, halogen, —CN, Preferably:
R$^1$ is H;
R$^2$ is H;
R$^3$ is C$_{3-6}$cycloalkyl, for example cyclopropyl,

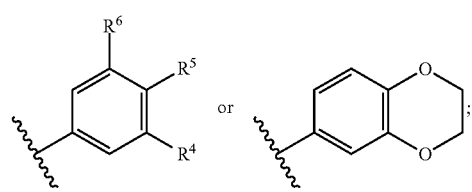

wherein:
R⁴ is H, —CN, —OC$_{1-6}$alkyl, C$_{1-6}$haloalkyl;
R⁵ is H, C$_{1-6}$alkyl-N—(X)(Y); a five or six membered cycloaryl, cycloalkyl or heterocycl having one, two or three heteroatoms selected from O, S and N and said cycloaryl, cycloalkyl or heterocycle being optionally substituted with a C$_{1-3}$alkyl, for example N-methylpiperazinyl, —OC$_{1-6}$alkyl-N(X)(Y);
wherein X is H or C$_{1-6}$alkyl, and Y is H or C$_{1-6}$alkyl; and wherein the alkyl groups are optionally substituted by one or more —OH groups; and
R⁶ is H or —OC$_{1-6}$alkyl.
Preferably:
R¹ is H;
R² is H;
R³ is cyclopropyl,

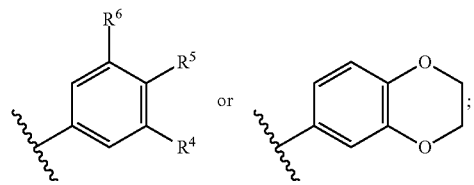

wherein:
R⁴ is H, —CN, —OCH$_3$, CF$_3$;
R⁵ is H, —CH$_2$N(CH$_3$)$_2$, N-methylpiperazinyl, —OCH$_2$CH(OH)CH$_2$N(CH$_3$)$_2$; and
R⁶ is H or —OCH$_3$.
In one embodiment R¹ is H, R² is H, R³ is cyclopropyl,

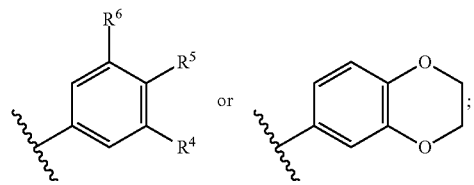

wherein:
R4 is H; R5 is —CH$_2$NEt$_2$, or —OCH$_2$CH(OH)CH$_2$N(CH$_3$)$_2$; and R6 is H; or
R4 is —CN, —OCH$_3$; R5 is H; and R6 is H; or
R4 is —CF$_3$; R5 is N-methylpiperazinyl; and R6 is H; or
R4 is —OCH$_3$; R5 is H; and R6 is —OCH$_3$.
In one embodiment, the inhibitor of Formula (I) is of the following formula:

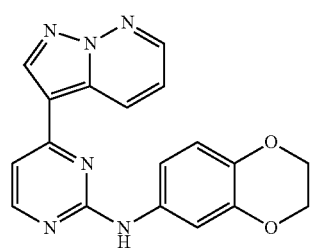

(II)

In another embodiment, the inhibitor of Formula (I) is of the following formula:

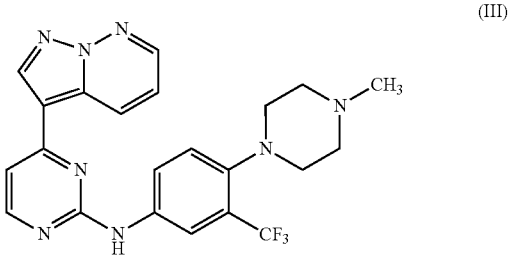 [SMILES: CN1CCN(c2ccc(Nc3nccc(-c4cnn5ncccc45)n3)cc2C(F)(F)F)CC1]

(III)

In another embodiment, the inhibitor of Formula (I) is of the following formula:

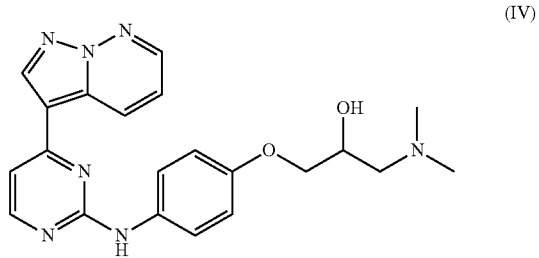 [SMILES: CN(C)CC(O)COc1ccc(Nc2nccc(-c3cnn4ncccc34)n2)cc1]

(IV)

In another embodiment, the inhibitor of Formula (I) is of the following formula:

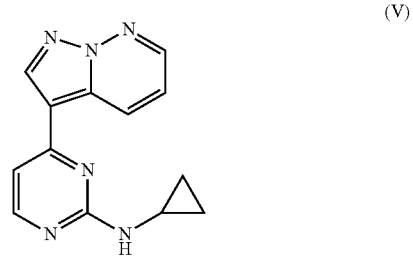 [SMILES: c1cnn2ncc(-c3ccnc(NC4CC4)n3)c2c1]

(V)

In one embodiment the inhibitor of Formula (I) is of the following formula:

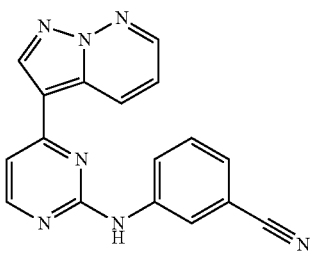

(VI)

In one embodiment the inhibitor of Formula (I) is of the following formula:

(VII)

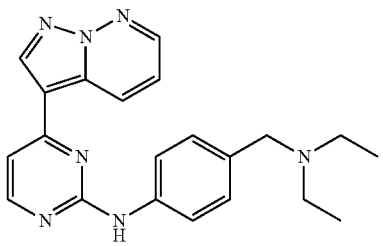

In one embodiment the inhibitor of Formula (I) is of the following formula:

(VIII)

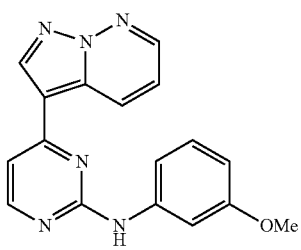

In one embodiment the inhibitor of Formula (I) is of the following formula:

(IX)

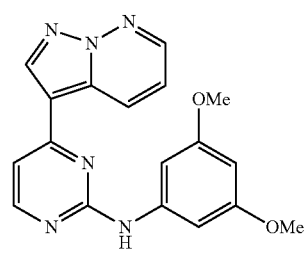

The inhibitor may comprise dinaciclib, or a derivative thereof. For example, in one embodiment the inhibitor comprises a compound of Formula (X) or a pharmaceutically acceptable salt or solvate thereof:

(X)

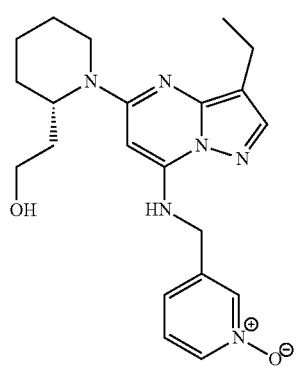

SCH 727965
(dinaciclib)

In one embodiment, the inhibitor comprises a compound of Formula (XI) or a pharmaceutically acceptable salt or solvate thereof:

(XI)

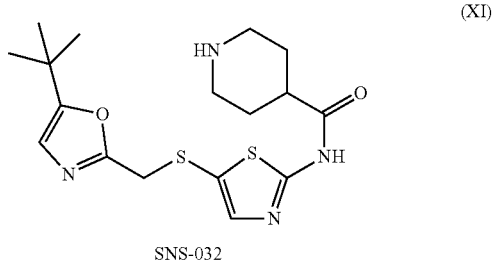 [SMILES: CC(C)(C)c1cnc(CSc2cnc(NC(=O)C3CCNCC3)s2)o1]

SNS-032

In one embodiment, the inhibitor comprises a compound of Formula (XII) or a pharmaceutically acceptable salt or solvate thereof:

(XII)

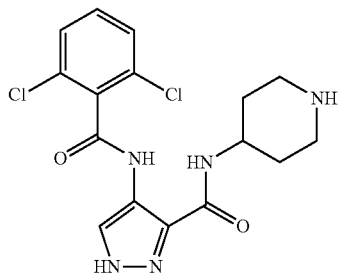

AT7519

In one embodiment, the inhibitor comprises a compound of Formula (XIII) or a pharmaceutically acceptable salt or solvate thereof:

(XIII)

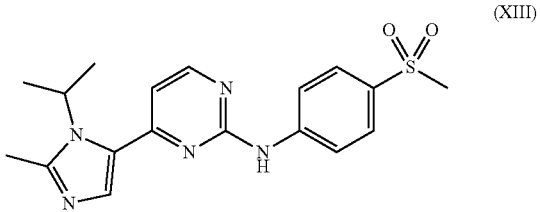

AZD 5438

In one embodiment, the inhibitor comprises a compound of Formula (XIV) or a pharmaceutically acceptable salt or solvate thereof:

(XIV)

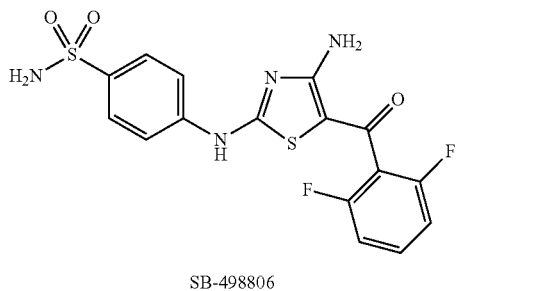

SB-498806

As used herein, the term "C1-C3 alkyl" refers to a straight-chain or branched-chain alkyl group containing from 1 to 3 carbon atoms. Examples of alkyl groups include, but are not limited to methyl, ethyl, propyl or isopropyl.

As used herein, the term "6 member heterocyclyl" refers to a saturated monocyclic heterocyclic group having 6 ring members and containing at least one heteroatom as a ring member, wherein each of said at least one heteroatoms may be independently selected from the group consisting of nitrogen, oxygen, and sulfur. One group of heterocyclyls has 1 heteroatom as ring member. Another group of heterocyclyls has 2 heteroatoms as ring members. Examples of heterocyclyl groups include, but are not limited to piperazinyl, morpholinyl, piperidinyl, oxanyl, thianyl or dioxanyl.

As used herein, the term "haloalkyl" refers to an alkyl group having the meaning as defined above wherein one or more hydrogens are replaced with a halogen. A halo C1-3 alkyl group refers to a haloalkyl group wherein the alkyl moiety has from 1 to 3 C atoms. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

Additionally, the compounds of Formulas I-XVI can contain asymmetric carbon atoms (chiral atoms) and can therefore exist in racemic and optically active forms. Thus, optical isomers or enantiomers, racemates, tautomers, and diastereomers are also encompassed in the compounds of Formulas I-XVI.

In one embodiment, the inhibitor is administered, or arranged to be administered, in combination with at least one other therapeutic agent. The one other therapeutic agent may comprise an oligonucleotide, such as siRNA or miRNA or equivalents thereof. The oligonucleotide may be capable of targeting expanded repeat transcript for degradation, for example through the RNA interference pathway. The oligonucleotide may comprise the sequence of (CAG)7. In another embodiment, the oligonucleotide may comprise the sequence of AGC AGC AGC AGC AG (SEQ ID NO: 7). In another embodiment, the oligonucleotide may comprise the sequence of CAG CAG CAG CAG CAG C (SEQ ID NO: 8). In another embodiment, the oligonucleotide may comprise the sequence of CGGAGCGGTTGTGAACTGGC (SEQ ID NO: 9).

The oligonucleotide may target the repeat sequence such as CUGn, CCUGn, CGGn, GGGGCCn, CAGn, or AUUCUn. Alternatively the siRNA oligonucleotide may bind anywhere in a target RNA which includes an expanded repeat transcript such as CUGn, CCUGn, CGGn, GGGGCCn, CAGn, AUUCUn. The skilled person will understand that U (uridine) residues will substitute T (thymine) residues in RNA relative to DNA. The siRNA oligonucleotide may bind anywhere in a target RNA which includes an expanded repeat transcript such as transcripts from any one of the transcripts from GenBank accession numbers: NM_001081563, AY329622, AF389886, AF389887, AH010982, L19493, JN681271, AF126749, NM_013236, NM_001271604, NM_002111, NM_000332, NM_002973, NM_004993, NM_000068, NM_000333, CR456776, D31840, or M34233.

The oligonucleotide may be at least 10, 11, 12, 13, 14, or 15 nucleotides long. In one embodiment, the oligonucleotide is at least 15 nucleotides long.

Advantageously, continuous exposure to inhibitor may be unnecessary to produce a beneficial effect in disorders caused by the generation of repeat expansion transcripts, such as DM-1. A pulsatile treatment may be sufficient. The inhibitor would remove nuclear foci from afflicted cells after a short exposure, and this short exposure leads to a prolonged effect, wherein the inhibitor treatment results in a shift in the relative proportions of wild type and mutant DMPK transcripts (CDK12 inhibition leads to a preferential loss of the expanded repeat transcript). This may result from CDK12 removal from the repeat expansion transcript with subsequent dissociation of the nuclear foci and degradation of the mutant transcript. The nuclear foci protect repeat expansion transcripts from degradation and once released, they may be vulnerable to cellular or targeted degradation. Thus, a "two-hit" therapy regime may be provided in which a short treatment with a CDK12 inhibitor is used to disperse foci and expose repeat expansion transcripts to degradation via endogenous processes, or by, for example, antisense oligonucleotides.

The at least one other therapeutic agent may comprise a small molecule, drug, pro-drug, peptide, protein, antibody, nucleotide or vaccine. The at least one other therapeutic agent may comprise a sodium channel blocker, such as mexiletine, phenytoin or procainamide. The at least one other therapeutic agent may comprise a CNS stimulant drug, such as modafinil, for example for treating excessive daytime sleepiness. The at least one other therapeutic agent may comprise dehydroepiandrosterone (DHEA), creatine supplementation or mecasermin rinfabate (IPLEX, combination of recombinant insulin-like growth factor 1 and its binding protein, BP-3), which may be provided, for example, for improving muscle weakness. The at least one other therapeutic agent may comprise any one or more of pentamidine, a bisamidinium inhibitor, lomofugin or dilomofungin.

In an embodiment a CDK inhibitor may be used in combination with an oligonucleotide that targets the DMPK gene. The DMPK gene may be in the expanded repeat in the 3' untranslated region or it may be targeted anywhere in the gene.

The use in combination with at least one other therapeutic agent may comprise a combined dose formulation or a separate dose formulation. The use may be concurrent or sequential.

The inhibitor may be administered, or arranged to be administered, intermittently. For example, the inhibitor may be administered, or arranged to be administered, once in a three-day treatment cycle. Alternatively, the inhibitor may be administered, or arranged to be administered, once in a 2-day treatment cycle. Alternatively, the inhibitor may be administered, or arranged to be administered, once in a 4-day treatment cycle. Alternatively, the inhibitor may be administered, or arranged to be administered, once in a treatment cycle of at least 3 days. Alternatively, the inhibitor may be administered, or arranged to be administered, once in a treatment cycle of at least 5 days. The inhibitor may be administered, or arranged to be administered, on day one of a three-day treatment cycle and wherein the dose is released within a 2-hour period immediately following administration.

The inhibitor may be provided and/or administered in a therapeutically effective dose. The dose may be sufficient to cause an alleviation or prevention of one or more symptoms of the disorder caused by the generation of repeat expansion transcripts, such as DM-1. The dose may be sufficient to cause an alleviation or prevention of all symptoms of the disorder caused by the generation of repeat expansion transcripts, such as DM-1. The dose may be sufficient to reduce the activity or presence of CDK12 by at least 50%. The dose may be sufficient to reduce the nuclear retention of repeat expansion transcripts by at least 50%. The dose may be sufficient to improve myotonia and muscle strength as judged by a six-minute walk test and hand grip test.

In one embodiment, the dose may comprise between about 2 and about 100 mg/kg. In one embodiment, the dose may comprise between about 5 and about 80 mg/kg. In one embodiment, the dose may comprise between about 2 and about 60 mg/kg. In one embodiment, the dose may comprise between about 5 and about 60 mg/kg. In one embodiment, the dose may comprise between about 5 and about 30 mg/kg. In one embodiment, the dose may comprise between about 5 and about 20 mg/kg. In one embodiment, the dose may comprise between about 5 and about 10 mg/kg. The dose may comprise no more than 60 mg/kg in a period of 24 hours. The dose may comprise no more than 30 mg/kg in a period of 24 hours. The dose may comprise no more than 10 mg/kg in a period of 24 hours. The dose may comprise no more than 5 mg/kg in a period of 24 hours. The dose may comprise no more than 100 mg/kg in a period of 3 days. The dose may comprise no more than 60 mg/kg in a period of 3 days. The dose may comprise no more than 30 mg/kg in a period of 3 days. The dose may comprise no more than 10 mg/kg in a period of 3 days. The dose may comprise no more than 5 mg/kg in a period of 3 days. The dose may comprise no more than 100 mg/kg in a period of 1 week. The dose may comprise no more than 60 mg/kg in a period of 1 week. The dose may comprise no more than 30 mg/kg in a period of 1 week. The dose may comprise no more than 20 mg/kg in a period of 1 week. The dose may comprise no more than 10 mg/kg in a period of 1 week. The dose may comprise no more than 100 mg/kg in a period of 2 or 4 weeks. The dose may comprise no more than 60 mg/kg in a period of 2 or 4 weeks. The dose may comprise no more than 30 mg/kg in a period of 2 or 4 weeks. The dose may comprise no more than 10 mg/kg in a period of 2 or 4 weeks. No more than 4 doses may be administered, or arranged to be administered, in a period of 24 hours. No more than 3 doses may be administered, or arranged to be administered, in a period of 24 hours. No more than 2 doses may be administered, or arranged to be administered, in a period of 24 hours. No more than 1 dose may be administered, or arranged to be administered, in a period of 24 hours. No more than 4 doses may be administered, or arranged to be administered, in a period of 3 days. No more than 3 doses may be administered, or arranged to be administered, in a period of 3 days. No more than 2 doses may be administered, or arranged to be administered, in a period of 3 days. No more than 1 dose may be administered, or arranged to be administered, in a period of 3 days. No more than 4 doses may be administered, or arranged to be administered, in a period of 1 week. No more than 3 doses may be administered, or arranged to be administered, in a period of 1 week. No more than 2 doses may be administered, or arranged to be administered, in a period of 1 week. No more than 1 dose may be administered, or arranged to be administered, in a period of 1 week. No more than 20 doses may be administered, or arranged to be administered, in a period of 2 or 4 weeks. No more than 15 doses may be administered, or arranged to be administered, in a period of 2 or 4 weeks. No more than 10 doses may be administered, or arranged to be administered, in a period of 2 or 4 weeks. No more than 8 doses may be administered, or arranged to be administered, in a period of 2 or 4 weeks. No more than 5 doses may be administered, or arranged to be administered, in a period of 2 or 4 weeks. No more than 4 doses may be administered, or arranged to be administered, in a period of 2 or 4 weeks. No more than 3 doses may be administered, or arranged to be administered, in a period of 2 or 4 weeks. No more than 2 doses may be administered, or arranged to be administered, in a period of 2 or 4 weeks. No more than 1 dose may be administered, or arranged to be administered, in a period of 2 or 4 weeks.

Advantageously, continuous exposure to the inhibitor may not be necessary to produce a beneficial effect in the treated subject and that a pulsatile treatment may be sufficient.

This method of administration may have the advantage of reducing side effects as it would allow a lower duration/frequency of inhibitor application.

The inhibitor may be administered orally or parenterally, for example, by intravenous, intramuscular or subcutaneous injection. In one embodiment, the inhibitor is suitable for oral administration.

The subject may be a mammal. In one embodiment the subject is human.

According to another aspect of the invention, there is provided the use of a CDK12 inhibitor in the preparation of a medicament for the treatment or prevention of a disorder caused by the generation of repeat expansion transcripts in a subject, for example RNA transcripts from a CTG repeat expansion.

According to another aspect of the invention, there is provided a method of treatment or prevention of a disorder caused by the generation of repeat expansion transcripts in a subject, comprising administering an inhibitor of CDK12 to the subject. The RNA repeat expansion transcripts may be from CTG repeat expansions.

The method may further comprise a subsequent administration of at least one other therapeutic agent. The at least one other therapeutic agent may comprise an oligonucleotide. The at least one other therapeutic agent may be suitable for enhancing degradation of nucleic acid repeat transcripts of DMPK.

According to another aspect of the invention, there is provided a method of screening for a therapeutic agent for a disorder caused by the generation of repeat expansion transcripts, such as RNA repeat expansion transcripts as in DM, comprising:
    providing a molecule for screening;
    detecting if the molecule inhibits the activity of CDK12, wherein detection of inhibition of CDK12 selects the molecule as a potential candidate therapeutic agent.

Detecting if the molecule inhibits the activity of CDK12 may comprise the use of an assay measuring any inhibition of CDK12 consumption of ATP during the phosphorylation of a substrate peptide in the presence of the molecule to be screened.

The inhibition of CDK12 may be selective inhibition. The method of screening may further comprise the step of detecting if the molecule does not significantly inhibit other cyclin dependent kinases, such as CDK9.

According to another aspect of the invention, there is provided a composition comprising a CDK12 inhibitor and a pharmaceutically acceptable carrier.

The composition may further comprise at least one other therapeutic agent. The least one other therapeutic agent may be capable of enhancing repeat expansion transcript degradation through cellular or targeted degradation. The at least one other therapeutic agent may comprise any one or more therapeutic agent described herein.

According to another aspect of the invention, there is provided a CDK12 inhibitor as described herein.

The skilled person will understand that optional features of one embodiment or aspect of the invention may be applicable, where appropriate, to other embodiments or aspects of the invention.

There now follows by way of example only a detailed description of the present invention with reference to the following drawings.

FIG. 1: Screening the PKIS compound collection identified 6 inhibitors that reduce nuclear foci. (A-F) Six inhibitors cause reduced nuclear foci across an 11 point dilution. Graphs show percentage of nuclear foci relative to DMSO treated cells. All six compounds share a pyrazolo[1,5b] pyridazine core structure.

Figure 2:
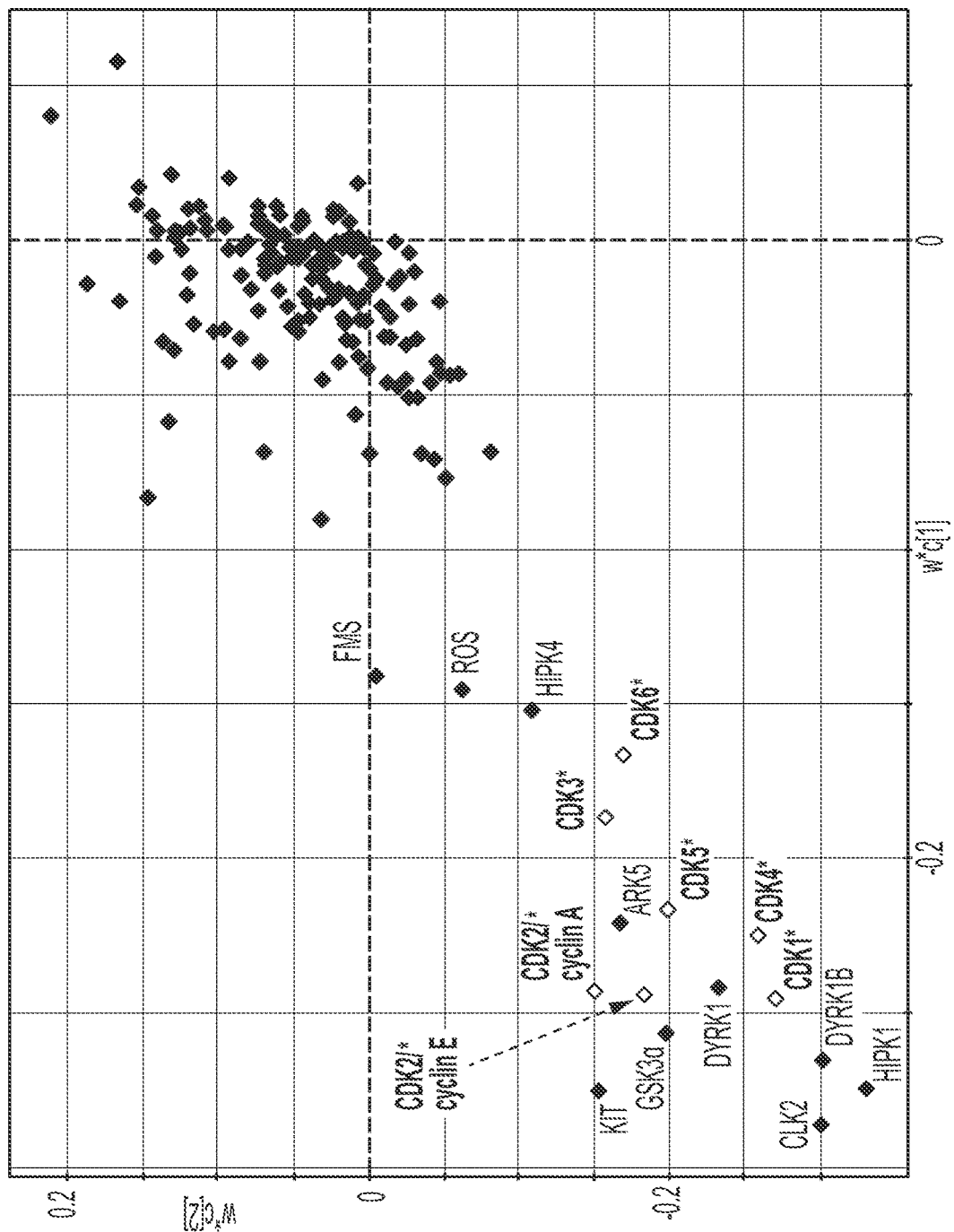
Figure 2:
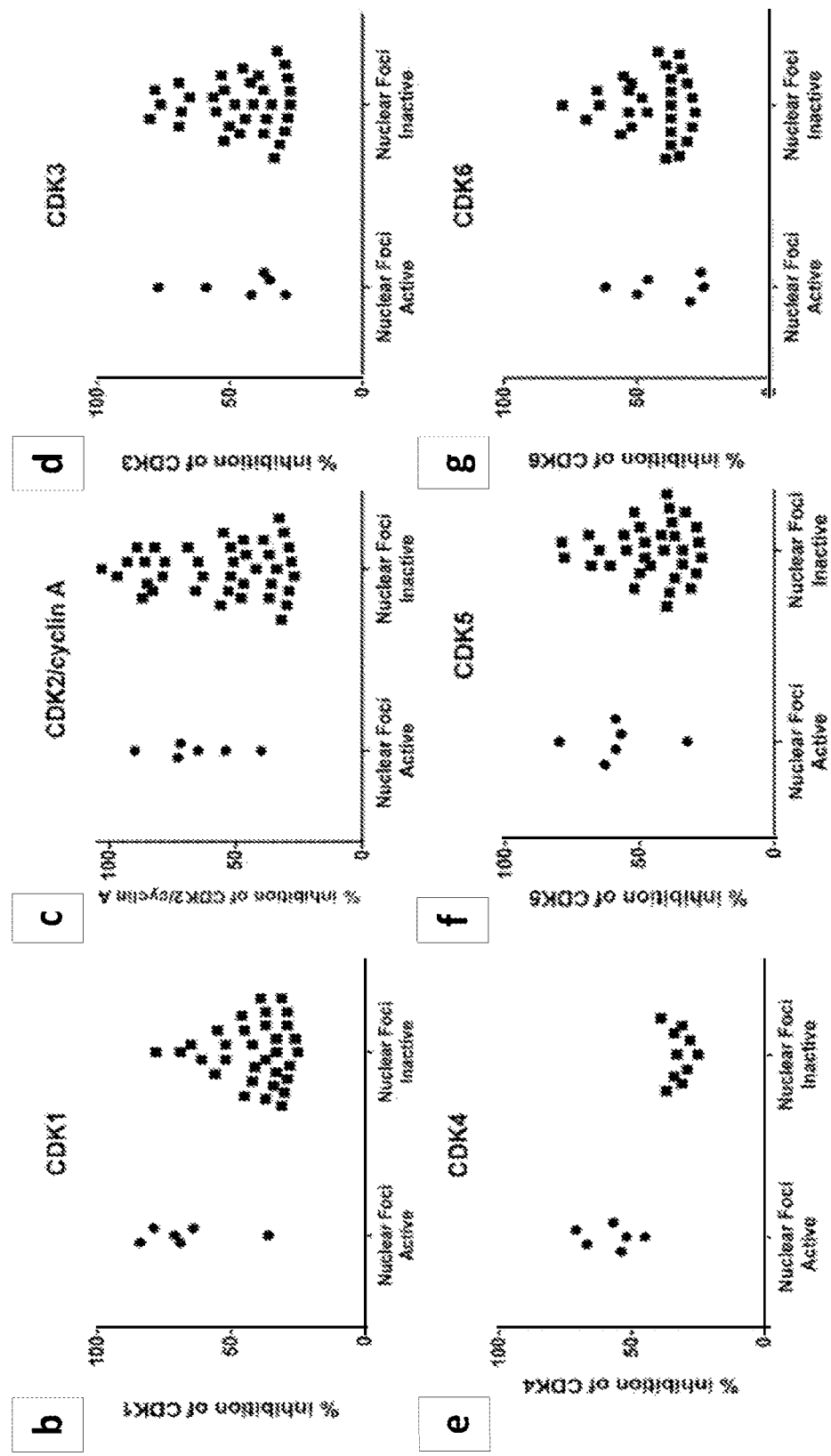

FIG. 2: Analysis of the PKIS inhibition profiles to identify common kinase targets. (A) Loading plot of 2-compound partial least squares model. Kinase activities correlating with the nuclear foci assay are labelled, with cyclin-dependent kinases highlighted with *. (B-G) Plots show the percentage inhibition of the kinase target at 0.1 µM concentration of compounds, grouped according to activity in the nuclear foci assay, including the six active compounds. Compounds with less than 25% inhibitory active activity on the kinase are not included on the graphs.

FIG. 3: Focused screening of CDK family inhibitors. 12 point dilution graphs plotting percentage of nuclear foci relative to DMSO treated cells for (A) SNS-032 (B) AT7519 (C) PD0332991 (D) R-roscovitine (E) dinaciclib (F) CDK9 inhibitor II.

Figure 4:
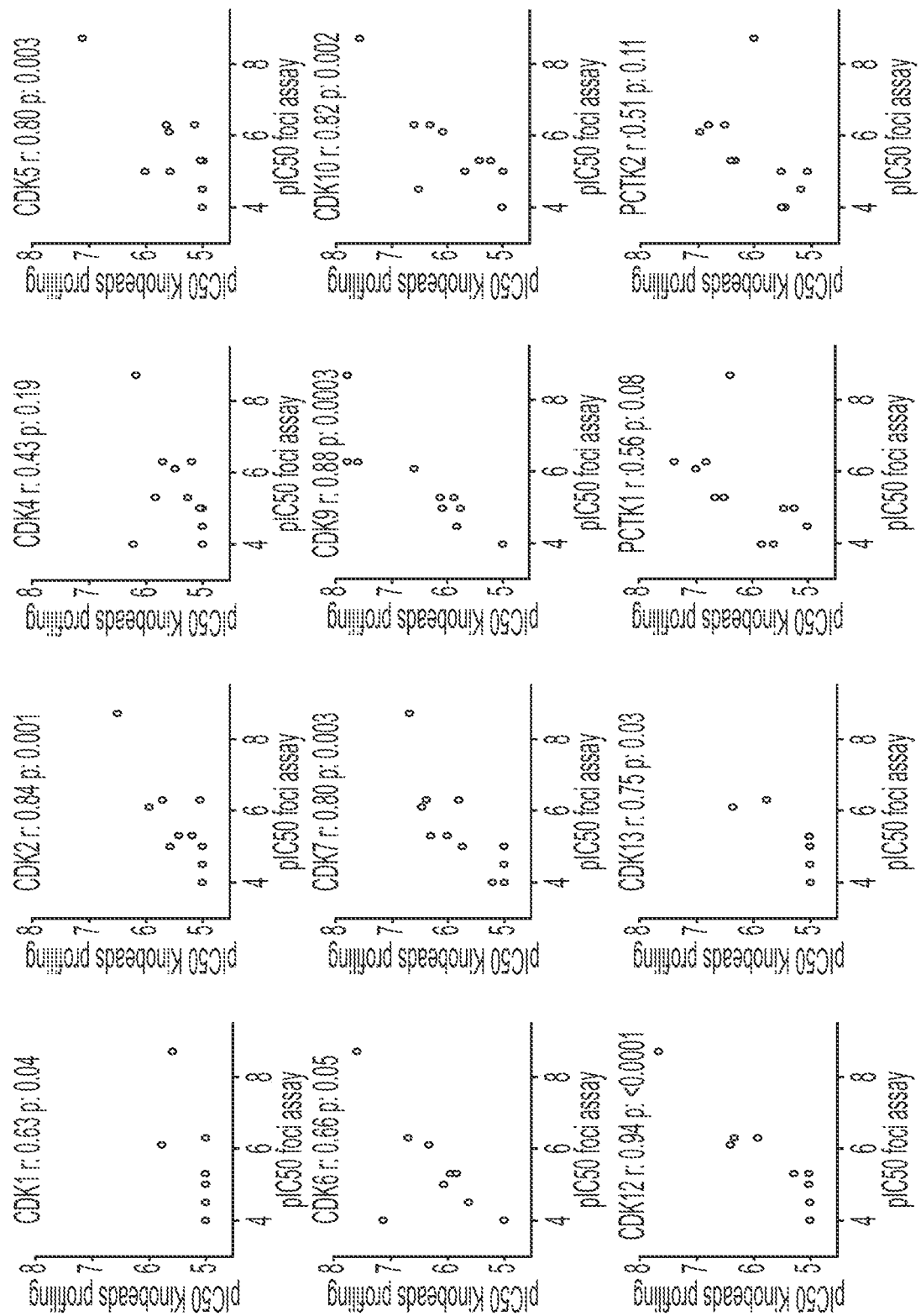

FIG. 4: Chemoproteomics target deconvolution. IC50 values were generated by affinity capturing of kinases from K562 or A204 cell extract using beads derivatized with SNS-032, in the presence of different concentrations of free competing compound or vehicle (DMSO). pIC50 values are plotted against the pIC50 in the foci inhibition assay for each compound. A good correlation of kinase binding affinity with the inhibitory activity on foci is observed for CDKS, CDK7, CDK9, and CDK12. r: Pearson correlation coefficient; p: p-value (calculated probability).

Figure 5:
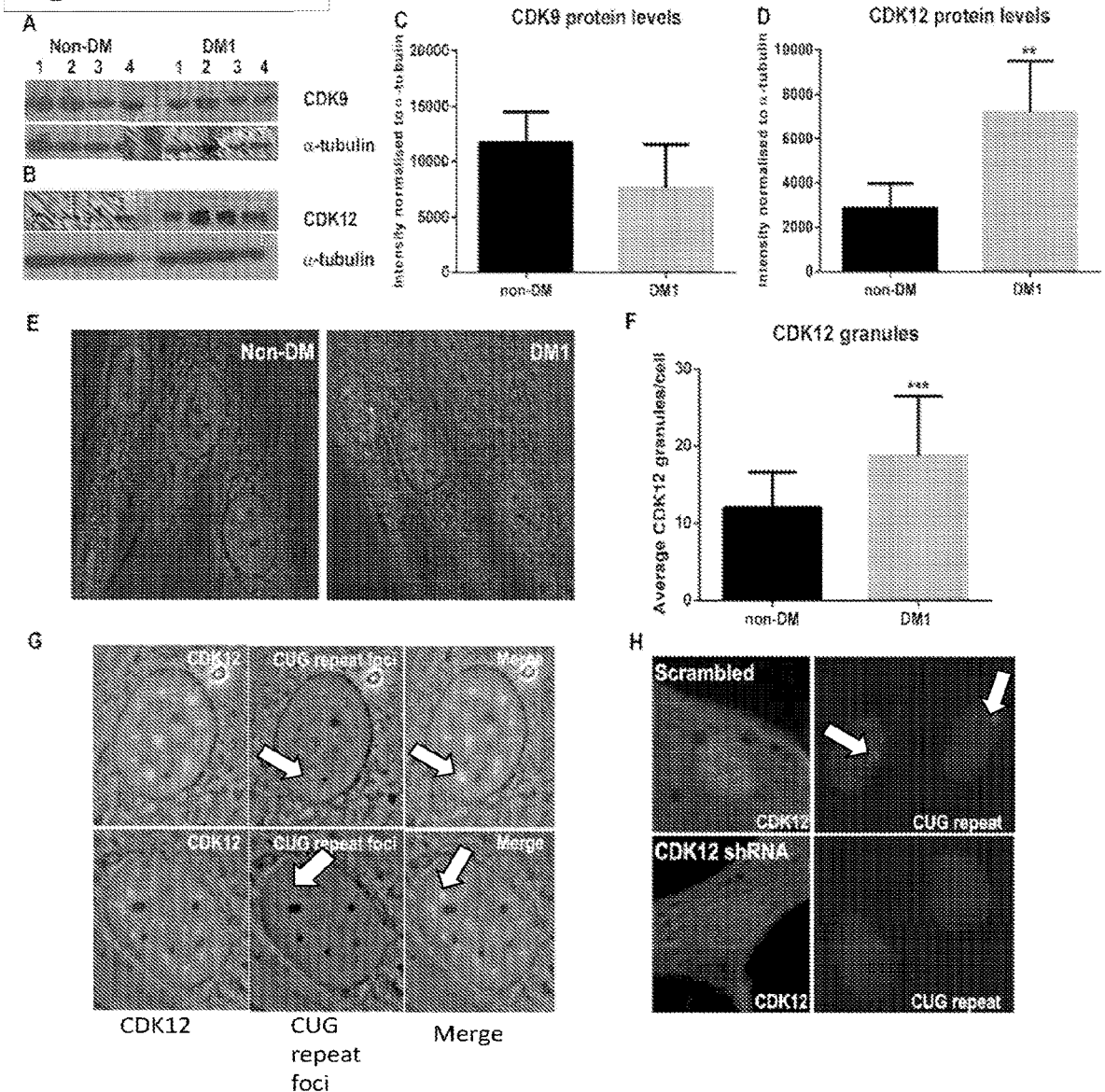

FIG. 5: CDK9 and CDK12 protein expression in DM. Western blot of vastus lateralis muscle biopsy samples in non-DM and DM1 patients for (A) CDK9 and (B) CDK12. Both blots are normalised to a-tubulin. (C) Histogram to quantify levels of CDK9 protein normalised to a-tubulin. (D) Histogram to quantify levels of CDK12 protein normalised to a-tubulin. (E) Immunohistochemistry of CDK12 in non-DM and DM1 fibroblast cells. (F) Quantification of the number of CDK12 nuclear granules. (G) Immunohistochemistry and in situ hybridisation shows co-localisation of repeat expansion foci with CDK12 nuclear granules (CDK12 in green/bright spots, repeat expansion RNA (Arrow)) (H) CDK12 protein knockdown by shRNA results in reduced CDK12 protein granules (green) and a subsequent reduction in CUG repeat expansion RNA foci (red/Arrow).

Figure 6:
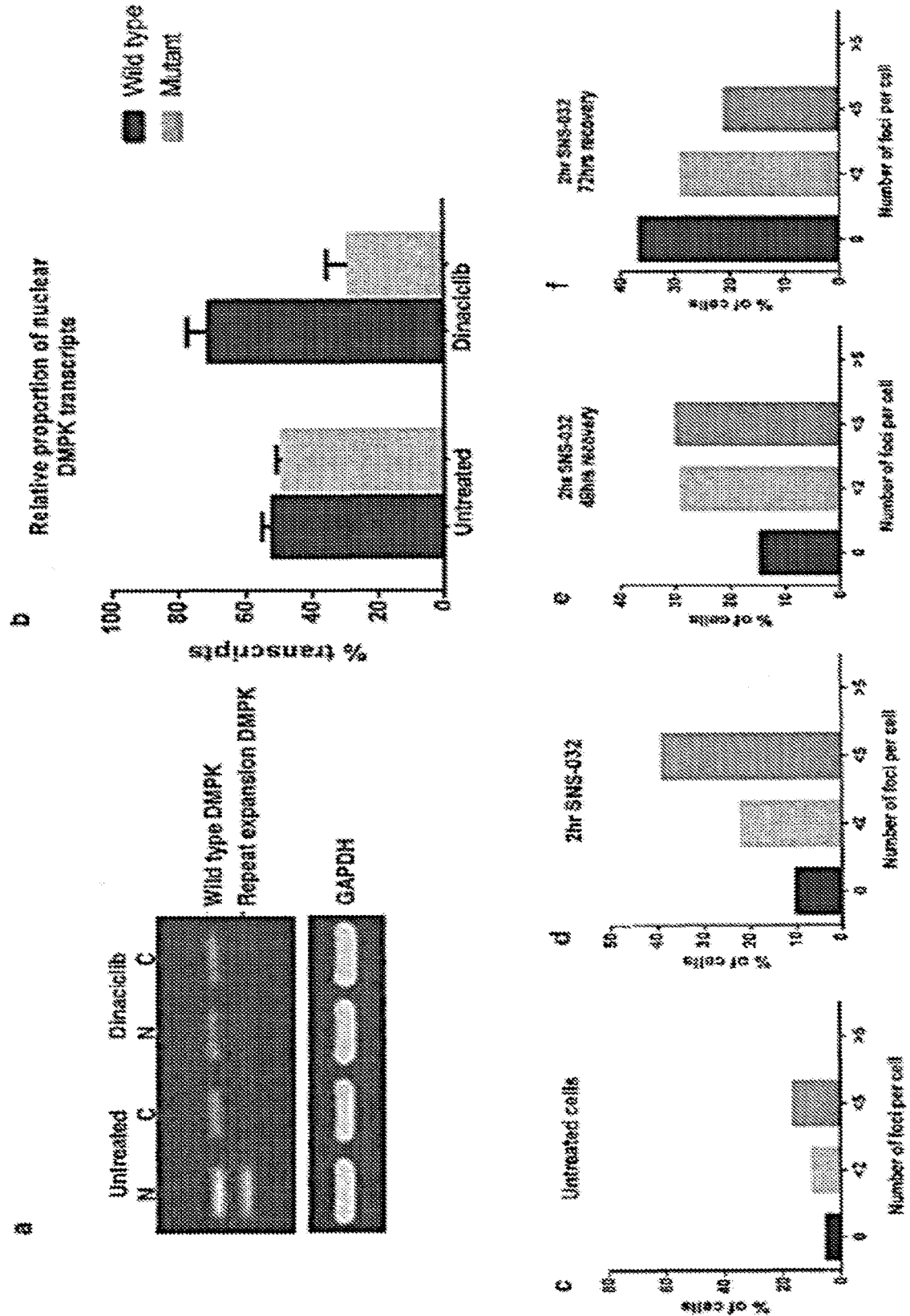

FIG. 6: Inhibitor treatment as a therapeutic for DM. (A) Ethidium bromide stained gel showing RT-PCR products from nuclear (N) and cytoplasmic (C) RNA fractions following amplification and BpmI digest of a fragment of DMPK. GAPDH is used as a loading control. (B) Histograms showing the relative proportions of nuclear mutant DMPK transcripts compared to wild type DMPK transcripts. The relative proportions of the mutant and wild type DMPK transcripts in DM1 fibroblast cells were assessed following treatment with dinaciclib (1 µM) for 24 hours. (C-F) Histograms show percentage of cells in the population with 0, <2, <5 and 5+ foci per nucleus (C) Untreated DM1 cells. (D) DM1 cells treated with SNS-032 for 2 hours. (E) DM1 cells treated with SNS-032 for 2 hours with 48 hours recovery in growth media (F) DM1 cells treated with SNS-032 for 2 hours with 72 hours recovery in growth media.

Figure 7:
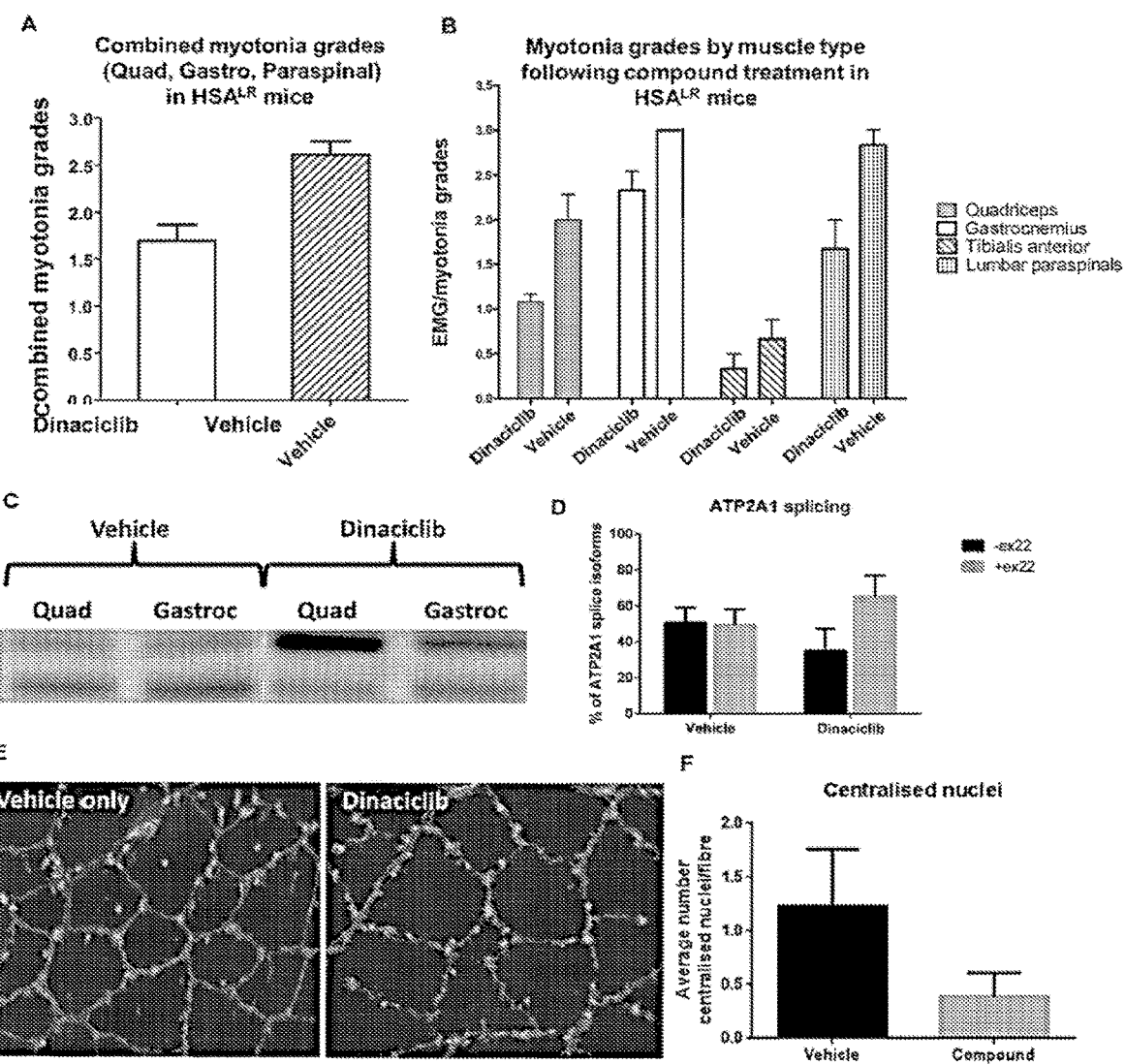

FIG. 7: Inhibitor treatment in a DM1 mouse model (A) Combined myotonia grade scores in quadriceps, gastrocnemius and paraspinal muscles from HSALR mice following vehicle and dinaciclib compound treatment (n=6 per treatment group) (B) Myotonia grades by muscle type in dinaciclib and vehicle treated HSALR mice. (C) Ethidium bromide stained gel to assess ATP2A1 splice isoforms in quadriceps and gastrocnemius muscle samples from vehicle and dinaciclib treated mice (D) Histogram showing the relative proportion of exon 22 exclusion and inclusion in vehicle and dinaciclib treated HSALR mice (E-F) Laminin stain demonstrates a reduction in centralised nuclei in muscle fibres of dinaciclib treated mice compared to vehicle control animals.

Figure 8:
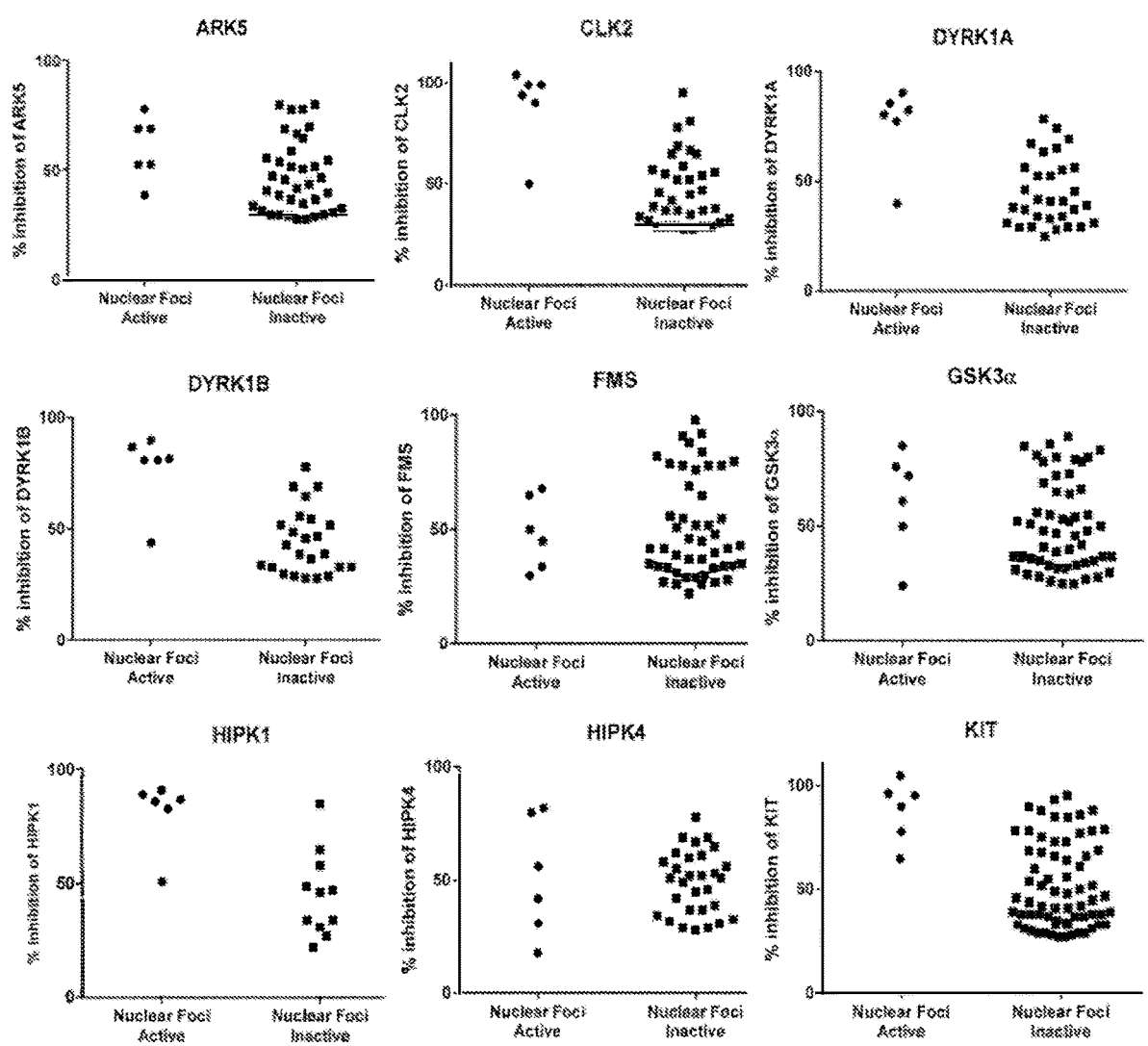

FIG. 8: Screening the PKIS collection identifies the CMGC kinase family. Plots to analyse the PKIS inhibition profiles of kinases identified from the partial least squares model as possible cellular targets comparing active versus inactive compounds. Compounds with less than 25% inhibition are not included on the graphs.

Figure 9B:
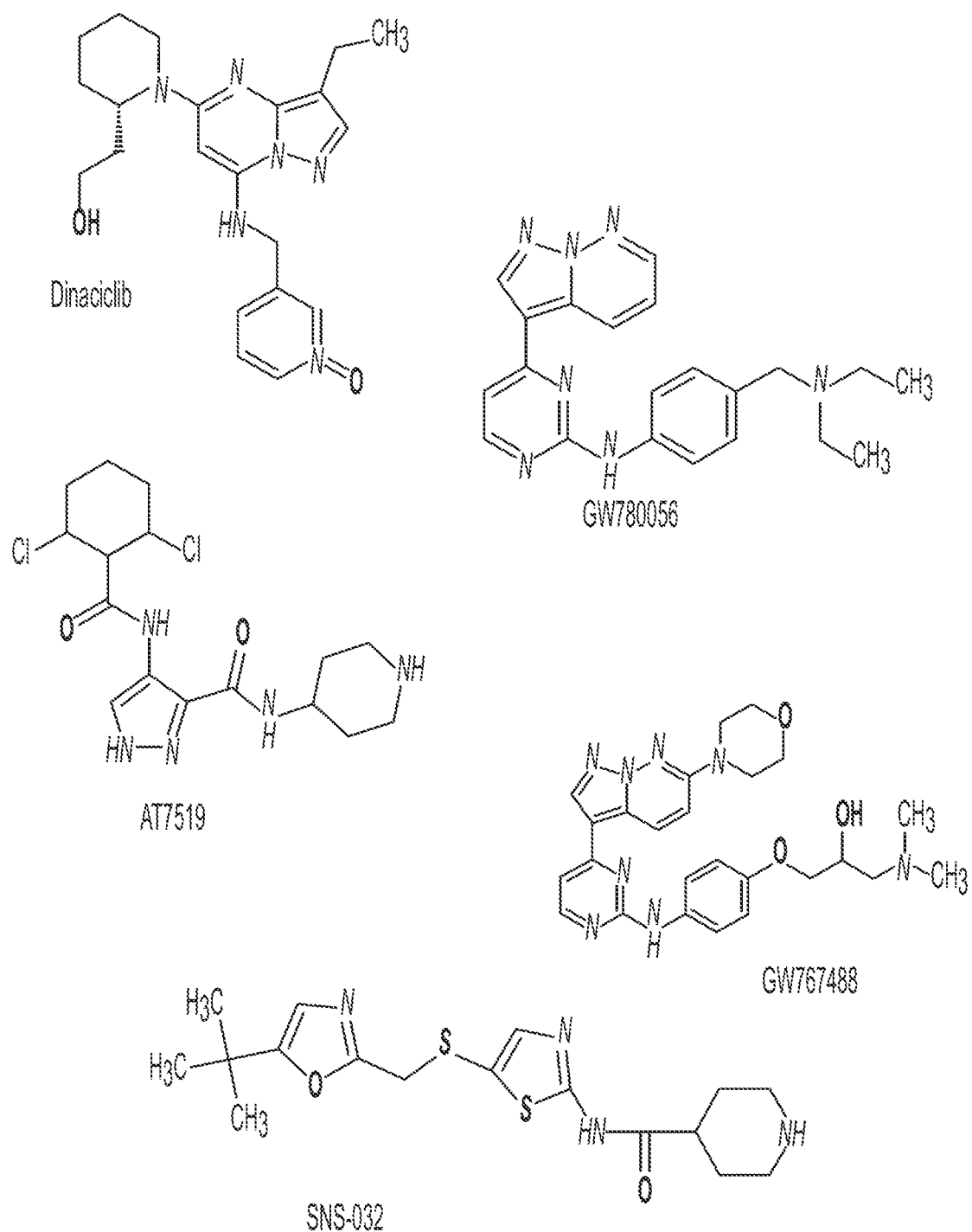
Figure 9B:
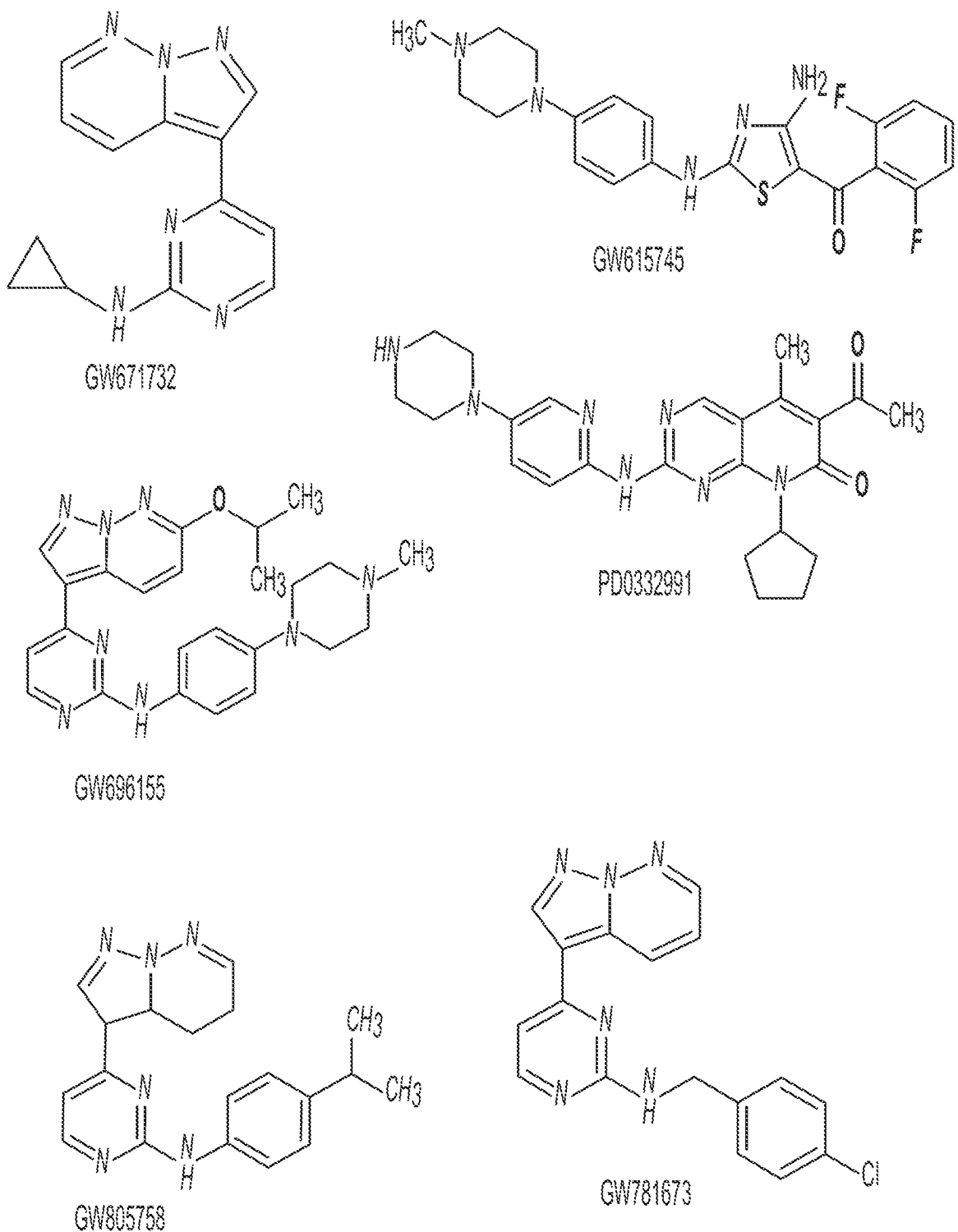

FIG. 9: Kinobead profiling of 11 compounds. Kinobeads profiling of a set of 11 compounds which represent a range of activities in the nuclear foci assay. Target profiles were generated by adding each compound to K562 cell extract at a concentration of 2 µM followed by incubation with kinobeads and quantification of bead-bound proteins. A: Values indicate target binding compared to a DMSO control where a value of 1 represents 100% binding and therefore no target inhibition and a value of 0 indicates 0% binding and 100% inhibition of the target kinase. B: Shows the structure of each compound tested.

Figure 10:
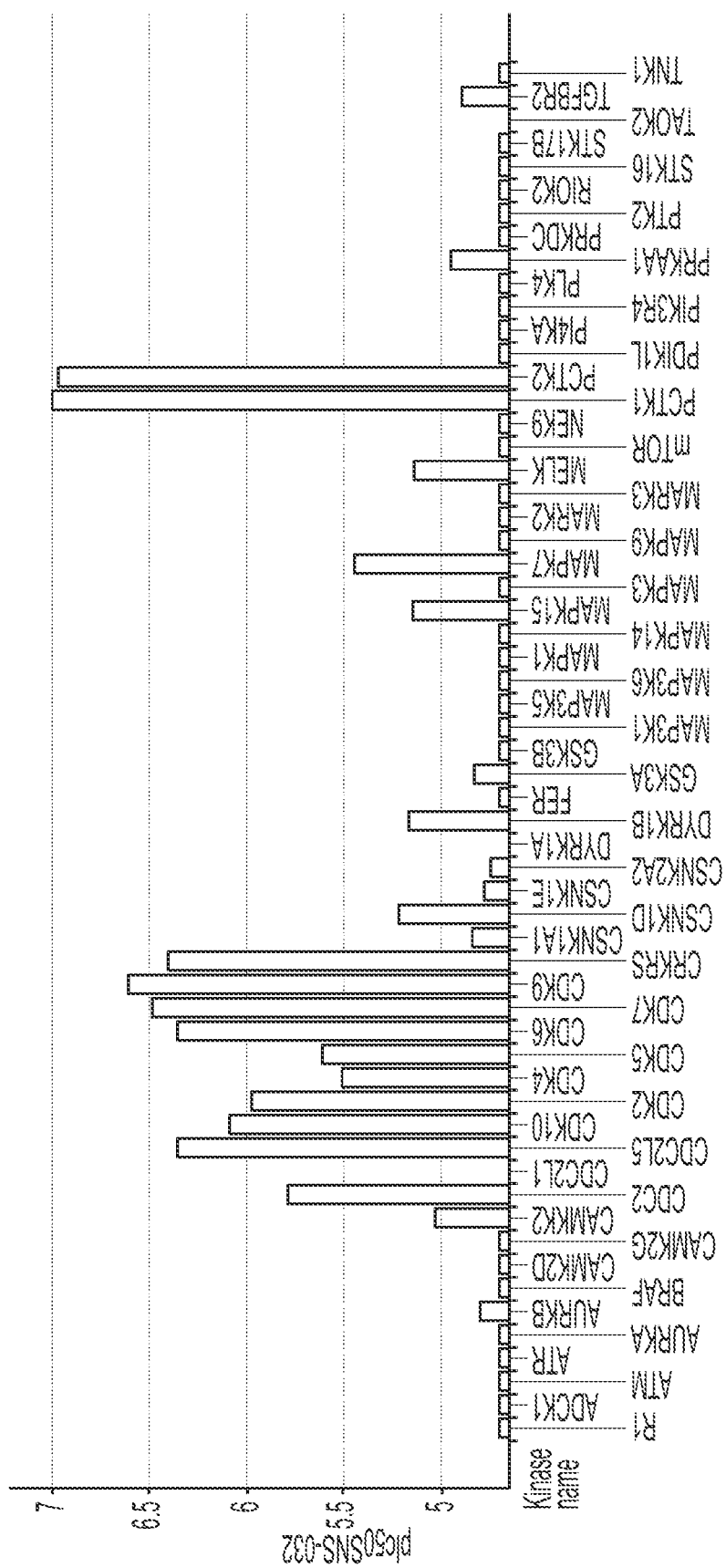
Figure 10:
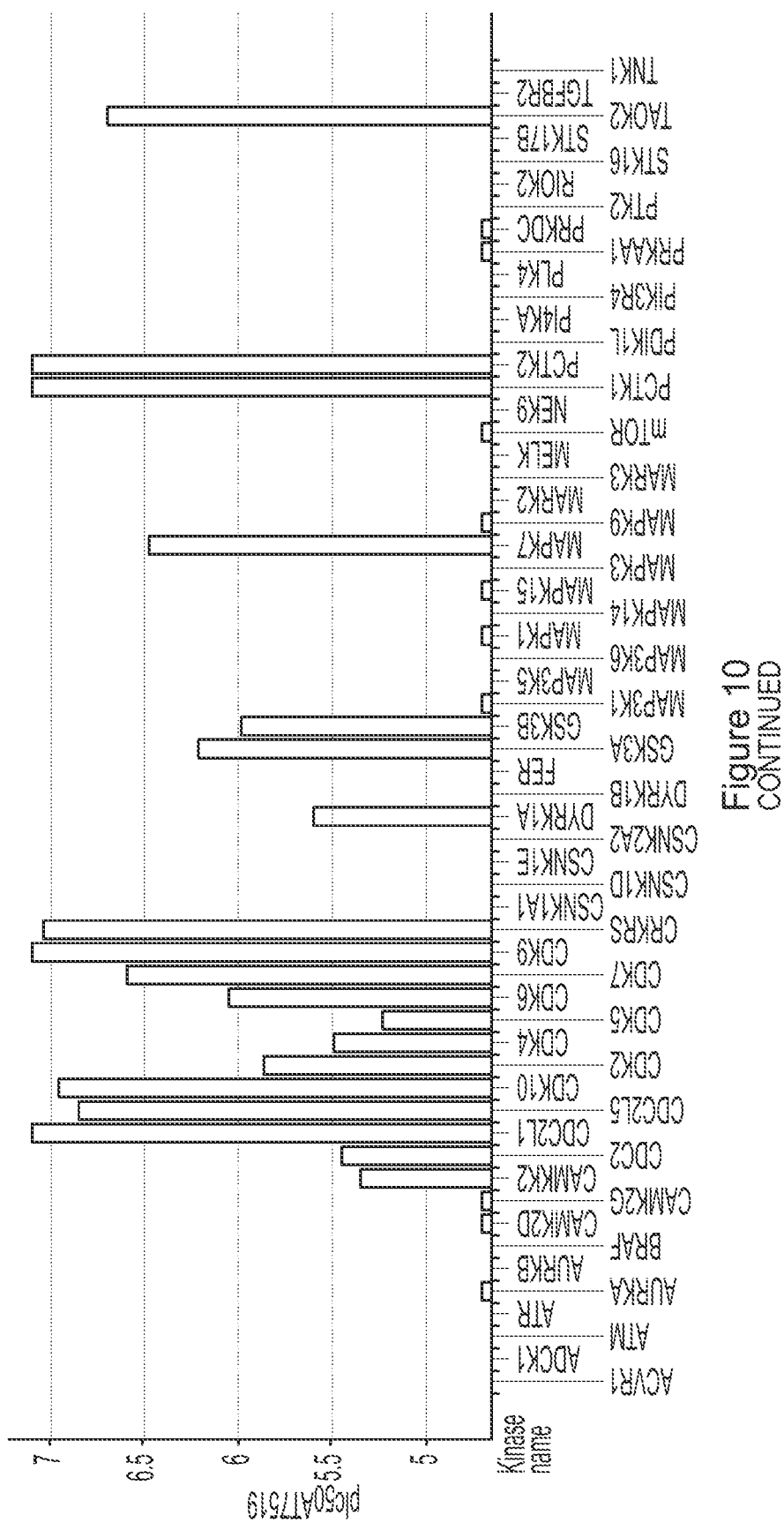

FIG. 10: Comparison of protein binding profiles for immobilised inhibitors SNS-032 and AT7519.

Figure 11:
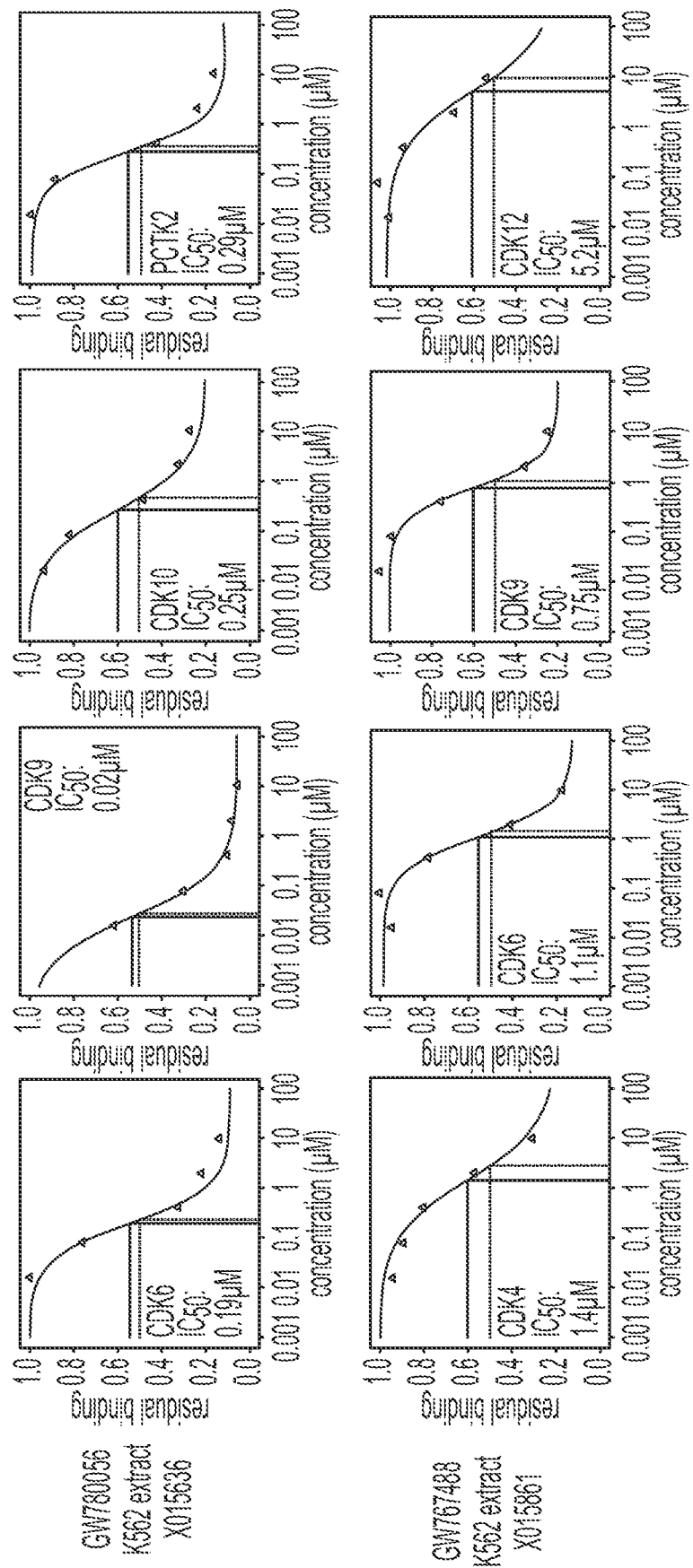
Figure 11:
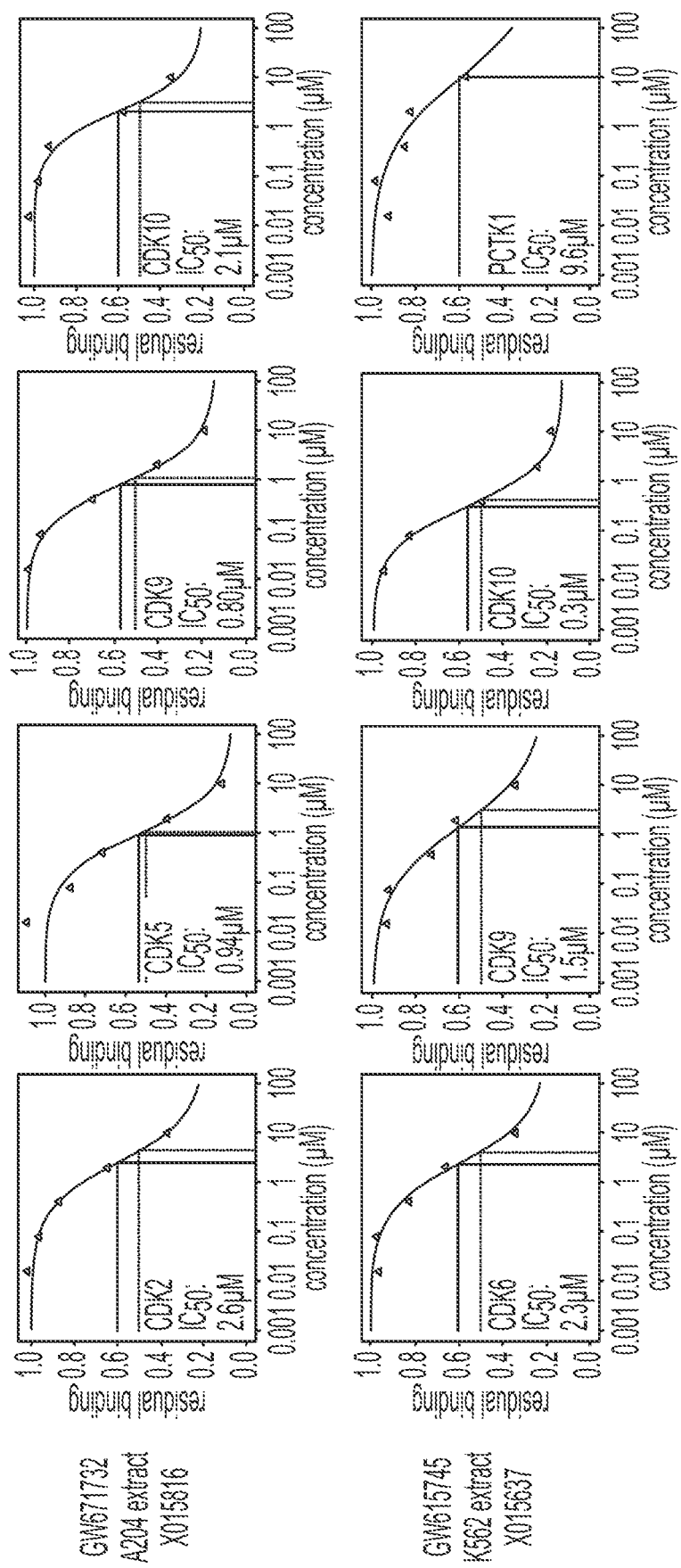

FIG. 11: Examples of dose-response competition binding curves for different compound/target combinations. An affinity matrix was generated by immobilisation of SNS-032 to sepharose beads and affinity capturing was performed from K562- or A204 cell extract in the presence of vehicle (DMSO) or different concentrations of inhibitor as indicated. IC50 concentrations and inflection points of the dose-response competition curves are indicated by dotted lines.

FIG. 12: CDK12 protein knockdown by siRNA and shRNA. (A) CDK12 immunohistochemistry following knockdown with scrambled and CDK12 shRNA (B) Quantification of CDK12 protein granules within the nucleus in CDK12 shRNA cells shows a 56% reduction in CDK12 granule number compared to scrambled shRNA (C) In situ hybridization analysis following knockdown with scrambled and CDK12 shRNA (D) Quantification of CUG repeat RNA foci within the nucleus in CDK12 shRNA cells shows a 69% reduction compared to scrambled shRNA (E) Histogram show percentage of cells in the population with 0, 1-2, 3-4 and 5+ foci per nucleus, in scrambled and CDK12 shRNA treated cells. (F) CDK12 immunohistochemistry following knockdown with scrambled and CDK12 siRNA (G) Quantification of CDK12 granules within the nucleus in CDK12 siRNA cells shows a 47% reduction in CDK12 granule number compared to scrambled siRNA (H) siRNA validation by western blot analysis for CDK12 and a-tubulin (I) Histogram of intensity scan of western blot analysis showed a 34% reduction in CDK12 protein compared to scrambled controls. Data normalized to a-tubulin. (J) In situ hybridization analysis following knockdown with scrambled and CDK12 siRNA (K) Quantification of CUG repeat RNA foci within the nucleus in CDK12 siRNA cells shows a 46% reduction compared to scrambled siRNA (L) Histograms show percentage of cells in the population with 0, 1-2, 3-4 and 5+ foci per nucleus, in scrambled and CDK12 siRNA treated cells.

FIG. 13: IC50 values of previously reported CDK inhibitors.

FIG. 14: pIC50 values generated by affinity capturing with the SNS-032 affinity matrix in K562 cell extract for the different CDK inhibitors added to the cell extracts.

INTRODUCTION

Myotonic dystrophy is caused by a CTG repeat expansion within the 3' untranslated region of the DMPK gene, leading to the formation of distinct nuclear foci. The involvement of kinases has been linked to the pathophysiology of the condition but to date a definitive kinase target for drug development has not been identified. It has been observed herein that CDK12 is elevated in DM cell lines and in DM patient muscle biopsies. Repeat expansion transcripts accumulate at the periphery of nuclear speckles and CDK12 co-localises with these nuclear speckles. It has been found that inhibition of CDK12 leads to the dispersal of DM-associated nuclear foci and degradation of repeat expansion transcripts.

Results and Discussion

Screening the PKIS Collection

Using a previously reported assay the PKIS collection was screened for compounds that reduce nuclear foci and the compounds were then analysed for their known selectivity profiles to identify the common kinase targets (Ketley, A. et al. (2014). *Hum Mol Genet*, 23: 1551-1562). DM1 fibroblasts were treated with compounds in an 11 point dilution series from 2011 M-19 nM for 24 hours. Following treatment, fluorescent in situ hybridisation was performed with a cy3 labelled CAG10 probe, to visualize nuclear foci and cells were analysed on a Molecular Devices plate reader with customised MetaExpress software (Ketley, A. et al. (2014). *Hum Mol Genet*, 23: 1551-1562). Compounds that reduced nuclear foci in a concentration dependent manner, compared to DMSO treated cells were identified and prioritized for further study. Six compounds that share a pyrazolo [1,5b]pyridazine core were found to reduce the number of nuclear foci following 24 hour treatment of DM cells (FIG. 1).

Target Deconvolution

The known selectivity profile of the six active compounds was examined to identify common kinase targets. The pIC50 values generated from the foci assays were compared to the compound inhibition profiles against 224 kinase targets (Drewry, D. H. et al. (2014). *Current topics in medicinal chemistry*, 14: 340-342). A partial least squares (PLS) model was used to cluster the data which suggested that the common target was likely to be a member of the CMGC (cyclin-dependent kinases (CDKs), mitogen-activated protein kinases (MAP kinases), glycogen synthase kinases (GSKs) and CDK-like kinases) family (FIG. 2A). Indeed, these compounds were originally designed to target CDK family members (Stevens, K. L. et al. (2008). *Bioorganic & medicinal chemistry letters*, 18: 5758-5762) and the inhibitors active in the nuclear foci assay all showed significant activity across many members of the CDK family. The kinase inhibition profiles for the six hit compounds were compared to their activity in the nuclear foci assay, which suggested that CDK1, CDK2, CDK3, CDKS and CDK6 are unlikely to be responsible for foci formation (FIG. 2B-G). Of the targets covered by the PKIS collection, CDK4 appeared more likely to play a role (FIG. 2E) but other CDK family members required consideration as they are absent from the PKIS annotations.

Focused Screening of Known CDK Family Inhibitor Molecules

Next, additional small molecule CDK inhibitors with well-annotated selectivity profiles were tested (FIG. 13) in the nuclear foci assay. This subset of inhibitors displayed differential activities in the nuclear foci assay and a diverse range of potencies across the CDK family members (FIG. 3). To confirm involvement of the CDK family the kinobeads methodology was employed, which is based on sepharose beads derivatized with a combination of promiscuous kinase inhibitors (Bantscheff, M. et al. (2007). *Nat Biotechnol*, 25: 1035-1044; Werner, T. et al. (2012). *Analytical chemistry*, 84: 7188-7194; and Kruse, U. et al. (2011). *Leukemia*, 25: 89-100) to profile 10 compounds, which represent a range of activities in the nuclear foci assay. Target profiles were generated by adding each compound to K562 erythroleukemia cell extract at a concentration of 2 followed by incubation with two variations of kinobeads and quantification of bead-bound proteins. The first type of bead was developed for the profiling of tyrosine and serine/threonine kinases of the eukaryotic protein kinase family (Bantscheff, M. et al. (2007). *Nat Biotechnol*, 25: 1035-1044), whereas the second type of bead captures additional kinases from the PI3K/lipid kinase family (Bergamini, G. et al. (2012). *Nature chemical biology*, 8: 576-582). The profiling results clearly indicated that the most active compounds in this subset exhibited shared activities only across the CDK family (FIG. 9A), consistent with the PKIS data.

To refine the possible target kinases, the IC50 values were compared for the nuclear foci active inhibitors and the nuclear foci inactive inhibitors. Small molecules SNS-032 (also known as BMS 387032) and AT-7519 demonstrate high activity in the nuclear foci assay and display the highest potency against CDK2 and CDK9 (FIGS. 3a and 3b and FIG. 13). However CDK2 cannot be responsible for nuclear foci reduction due to significant overlap in the IC50 values of active and inactive compounds against this target. Likewise CDK1, CDK4, CDK5, CDK6 and CDK7 can all be discounted for similar reasons (FIG. 13).

The analysis of this subset of known CDK inhibitor compounds confirms the results of the PKIS screen but raises the possibility that the target responsible for nuclear foci reduction is a less well described CDK family member. To investigate this possibility four additional CDK inhibitors, with a range of potencies, were tested to determine the potential involvement of CDK9 as a possible target (FIG. 3E-F and FIG. 13). Interestingly, dinaciclib and SNS-032 have the same IC50 value against CDK9, however, dinaciclib displays a significantly increased activity in the nuclear foci assay. Furthermore, CDK9 Inhibitor II (FIG. 3F), which is a specific but less potent CDK9 inhibitor, with an IC50 value of 350 nM, reduced nuclear foci at the highest concentration whereas two other compounds; PD0332991 and R-roscovitine, with comparable CDK9 IC50 values (400 nM and 500 nM, respectively) are inactive in the nuclear foci assay at the concentrations tested (FIGS. 3C and 3D). These data suggest an additional CDK family member as the target for nuclear foci reduction.

Chemoproteomics Target Resolution

To determine the specific CDKs responsible for the reduction of nuclear foci it was sought to expand the target coverage within the CDK family by the immobilization of two of the active compounds containing a suitable secondary amine; SNS-032 and AT7519 (FIG. 10). Beads derivatized with either compound showed good coverage of the CDK family, including family members which are not present in commercial kinase panels. For an in depth chemoproteomics study profiling inhibitor selectivity across the CDK family, dose-response competition-binding profiles were generated for all active and one of the inactive compounds (PD0332991) in K562 cells or in A204 rhabdomyosarcoma cells. To confirm that the K562, A204 and DM1 cell lines express the same kinases a whole proteome analysis was conducted. All CDK/PCTK proteins identified by profiling were also identified in the cells used for the phenotypic foci assay as follows:

CDK family member proteins identified by whole proteome analysis of DM fibroblasts (protein accession numbers for CDK family proteins).

CDK1: P06493
CDK2: CAA43807.1
CDK4: CAG47043
CDK5: CAG33322
CDK6: Q00534
CDK7: P50613
CDK9: AAF72183
CDK10: AAH25301
CDK12: Q9NYV4.2
CDK13: Q14004.2
PCTK1: Q00536
PCTK2: Q00537.2

The resulting dataset comprises IC50 curves for 12 CDK family kinases (FIG. 11, FIG. 14). The best correlation across the compound set of kinase IC50 values with the inhibitory activity on foci was observed for CDK12, followed by CDK9 (FIG. 4). The IC50 values for CDK9 and CDK12 are closely in line with their observed activity in the foci assay, whereas the IC50 values for CDK2 and CDK7 appear too low to implicate them as targets. Consistent with the previous analysis, presented in FIG. 3E, dinaciclib was the most active inhibitor against the CDK family, in particular for CDK12, suggesting it may be the most likely kinase target.

CDK12 in DM Pathogenesis

Thus far the experiments point to CDK12 as the most likely kinase to have an association with repeat expansion foci. To examine the potential involvement in DM pathogenesis, the endogenous levels of CDK12 were assessed, in addition to CDK9, in vastus lateralis muscle biopsy samples from four DM1 and four healthy volunteers using Western blots. No significant difference in CDK9 protein level compared to that in controls could be detected (FIGS. 5A and 5C). However, there was a clear increase in levels of CDK12 in DM biopsies versus those from healthy volunteers, with 48% more CDK12 protein detected in DM samples (p=0.0025) (FIGS. 5B and 5D).

To understand the relationship between nuclear foci and CDK12 in DM pathophysiology, the cellular location of the protein was established by immunohistochemistry in DM and non-DM fibroblasts. Consistent with previously published data in non-DM cells CDK12 was localised in the nucleus in granular structures in both DM and non-DM cells (Ko, T. K. et al. (2001). *Journal of cell science*, 114: 2591-2603) (FIG. 5E). Quantification of these structures in 400 cells showed that the number of granules was elevated in DM cells, with an average number of 18.74 (±3.88), compared to 12.07 (±2.27) in non-DM cells (p<0.0001) (FIG. 5f). The size of CDK12 granules was not significantly different in non-DM and DM cells. This increase in number is consistent with the increased overall levels of CDK12 protein detected by Western blot. Next immunohistochemistry of CDK12 was conducted followed by in situ hybridisation to detect the repeat expansion RNA foci. Co-localisation of the repeat expansion foci with CDK12 protein was found. Quantification using customised MetaXpress software revealed that 100% of repeat expansion foci co-localised with CDK12 protein (FIG. 5g). To understand the impact of increased CDK12 protein in DM and the relationship between CDK12 protein granules and repeat expansion foci shRNA and siRNA were used to reduce the number of CDK12 granules in DM cells. The effect on repeat expansion foci was then assessed. Following lentiviral infection expressing three shRNAs against CDK12 a 56% reduction in the number of CDK12 granules and a 69% reduction in repeat expansion foci compared to control cells was observed (FIG. 5H and FIG. 12A-E). This was verified by siRNA knockdown of CDK12 and quantification by Western blot analysis, which confirmed a 34% reduction in protein levels. This resulted in a 46% reduction in CDK12 protein granules and a 47% reduction in repeat expansion RNA foci indicating that specific inhibition of CDK12 and dissolution of CDK12 protein from nuclear granules leads to a dispersal of repeat expansion foci (FIG. 12F-L).

Inhibitor Treatment as a Therapeutic for DM

As an association between CDK12 and nuclear foci has been established, and nuclear foci comprise repeat expansion transcripts, it was sought to establish the effect of inhibitor treatment on the level of repeat expansion transcripts. For this an RT-PCR assay was employed that utilises a Bpml polymorphism to distinguish between wild-type and mutant DMPK transcripts (FIG. 6A) (Hamshere, M. G. et al. (1997). *Pro Natl Acad Sci USA*, 94: 7394-7399). Following treatment with dinaciclib, analysis of nuclear and cytoplasmic cell extracts showed that the repeat expansion transcripts were still retained within the nuclear fraction. However, quantification using Genescan analysis showed a 59% decrease in the relative proportion of repeat expansion transcripts compared to wild type transcripts in the nucleus (FIG. 6B). These data indicate that exposure to dinaciclib, leads to preferential loss of the repeat containing transcript, which in turn suggests that targeting CDK12 provides a viable option for DM treatment development.

Loss of the repeat transcript may result from incomplete transcription of the expanded transcript following inhibitor treatment or it may be due to CDK12 removal from the repeat expansion transcript with subsequent dissociation of the nuclear foci and degradation of the mutant transcript. If the latter is correct it would suggest that nuclear foci protect repeat expansion transcripts from degradation and once released, they may be vulnerable to cellular or targeted degradation. Thus, a possible two-hit therapy regime is proposed in which short treatment with a CDK12 inhibitor is used to disperse foci and expose repeat expansion transcripts to degradation via endogenous processes or by antisense oligonucleotides (Mulders, S. A. et al. (2009). *Proc Natl Acad Sci USA*, 106: 13915-13920).

As CDK12 is a transcription-regulating kinase associated with nuclear foci in DM cells, it was sought to establish the effect of inhibiting this target on the kinetics of nuclear foci formation and dispersal. To do this DM1 fibroblast cells were exposed to the two most potent foci reducing compounds, dinaciclib and SNS-032, for different lengths of time from 2 hours to 48 hours. Both compounds produced a significant reduction in foci but this was most rapid in the case of SNS-032, which was effective following just 2 hours of treatment. Continuous exposure to transcription-regulating inhibitors, would not be a viable therapy option for DM, thus the effect of short term treatment on nuclear foci was examined. DM1 fibroblasts were exposed to SNS-032 for 2 hours, after which time the cells were washed thoroughly and allowed to recover in complete growth media. Quantification of nuclear foci showed that 68% of untreated DM1 cells have more than 5 foci and only 5% have no detectable foci (FIG. 6C). When cells are treated with SNS-032 for 2 hours, with no recovery time, this distribution shifts to 28% of cells with more than 5 foci and 10% cells with no foci (FIG. 6D). However, following 48 and 72 hours of recovery following exposure to SNS-032, the proportion of cells without nuclear foci increases further to 14% and 36%, respectively (FIGS. 6E and 6F). Taken together this data suggests that a short (2 hr) treatment with inhibitor, followed by a prolonged (72 hr) recovery leads to a significant reduction in numbers of nuclear foci and a preferential reduction in mutant transcripts, and therefore that pulsatile treatment could be an efficacious approach to DM therapy.

To establish the in vivo effect of this inhibitor $HSA^{LR}$ mice were treated by intraperitoneal injection for a 28 day treatment period comprising 12 injections in total. Following inhibitor treatment the mice were analysed by EMG analysis to assess the functional effect on myotonia and demonstrated a significant improvement in the myotonia grade score across the four muscle types tested; quadriceps, gastrocnemius, tibialis anterior and the lumbar paraspinals (p=0.0021, n=6) (FIG. 7A-B). Molecular analysis demonstrated an improvement in the inclusion of exon 22 for the splice isoforms of ATP2A1 (FIG. 7C-D) and a reduction in the presence of centralised nuclei within muscle fibres following inhibitor treatment (FIG. 7E-F).

Materials and Methods

Cell Culture

Fibroblast cells were grown in Dulbecco's Modified Eagles Medium (DMEM) with penicillin and streptomycin, and 10% fetal calf serum (Sigma).

In Situ Hybridization Protocol

Cells were exposed to compounds for 24 hrs after which in situ hybridization was performed to identify foci using a Cy3 labelled $(CAG)_{10}$ probe. Plates were analysed on a Molecular Devices Micro High Content Imaging system, with nine fields imaged per well to give approximately 100 cells per well, per compound treatment. The nuclear area was identified by Hoechst stain and the number, size and intensity of foci was determined by scoring adjacent pixels that were 80 grayscales or more above background.

Preparation of Cell Extracts

K562 and A204 cells were obtained from ATCC and cultured in RPMI medium containing 10% FCS. Cells were expanded to 1.5×106 cells/ml. A204 cells were cultured in McCoy's 5A medium containing 15% FCS. Cells were expanded to 100% confluency. Cells were harvested and subjected to 3 washes with ice-cold PBS. Aliquots were snap frozen in liquid nitrogen and stored at −80° C. Cell extracts were prepared as described (Bantscheff, M. et al. (2011). *Nat Biotechnol*, 29: 255-265).

Chemoproteomics

Affinity profiling was performed as described previously (Bantscheff, M. et al. (2007). *Nat Biotechnol*, 25: 1035-1044 and Bantscheff, M. et al. (2011). *Nat Biotechnol*, 29: 255-265). Sepharose beads were derivatized with SNS-032 at a concentration of 1 mM to generate a bead matrix, or Kinobeads™ were used as a matrix for profiling. Beads (35 μl in case of Kinobeads™ or 5 μl in case of SNS-032) were washed and equilibrated in lysis buffer at 4° C. for 1 h with 1 ml (5 mg) K562 cell extract, which was pre-incubated with compound or buffer. Beads were transferred to disposable columns (MoBiTec), washed extensively with lysis buffer and eluted with SDS sample buffer. Proteins were alkylated, separated on 4-12% NuPAGE (Invitrogen), stained with colloidal Coomassie, and quantified by isobaric mass tagging and LC-MS/MS.

Peptide and Protein Identification and Quantification

Sample preparation and labeling with TMT isobaric mass tags was performed essentially as described (Bantscheff, M. et al. (2011). *Nat Biotechnol*, 29: 255-265). For mass spectrometric analyses samples were dried in vacuo and resuspended in 0.1% formic acid in water and aliquots of the sample were injected into a nano-LC system coupled to a mass spectrometer: Eksigent 1D+ coupled to LTQ-OrbitrapXL mass spectrometer, Waters nanoAcquity coupled to Orbitrap Elite mass spectrometer, or Ultimate 3000 RSLC nano coupled to Q Exactive mass spectrometer (Thermo Fisher Scientific). Peptides were separated on custom 50 cm×75 μM (internal diameter) reversed-phase columns (Reprosil) at 40° C. Gradient elution was performed from 3% acetonitrile to 40% acetonitrile in 0.1% formic acid over 120-270 min. LTQ-Orbitrap XL was operated with Xcalibur 2.0, Orbitrap Elite and Q Exactive instruments were operated with Xcalibur 2.2 software. Intact peptides were detected in the LTQ-OrbitrapXL/Orbitrap Elite at 30.000 resolution (measured at m/z=400), in the Q Exactive at 70.000 resolution (m/z=200). Internal calibration was performed with LTQ-OrbitrapXL using the ion signal from (Si(CH3)20)6H+ at m/z 445.120025. Data-dependent tandem mass spectra were generated for up to ten peptide precursors (LTQ-OrbitrapXL/Orbitrap Elite six precursor, Q Exactive ten) using a combined CID/HCD (LTQ-Orbitrap XL) approach or using HCD only (Orbitrap Elite/Q Exactive) at a resolution of 15.000/17.500. For CID up to 5,000 ions (LTQ-Orbitrap XL) were accumulated in the ion trap (maximum ion accumulation time=150 msec), for HCD up to 50.000 ions (LTQ-OrbitrapXL, maximum ion accumulation time=350 msec), up to 30.000 ions (Orbitrap Elite, maximum ion accumulation time=150 msec) and 1e6 ions (Q Exactive, maximum ion accumulation time=60 msec) were accumulated in the HCD cell. Mascot 2.3 and 2.4 (Matrix Science) was used for protein identification using 10 p.p.m. mass tolerance for peptide precursors and 0.6 Da (CID) or 20 mDa (HCD) tolerance for fragment ions. Carbamidomethylation of cysteine residues and TMT modification of lysine residues were set as fixed modifications and methionine oxidation, N-terminal acetylation of proteins and TMT modification of peptide N-termini were set as variable modifications. The search database consisted of a customized version of the International Protein Index database combined with a decoy version of this database created using a script supplied by Matrix Science. Criteria for protein quantification were: a minimum of 2 sequence assignments matching to unique peptides was required (FDR for quantified proteins <<0.1%), Mascot ion score >10, signal to background ratio of the precursor ion >4, signal to interference >0.5 (Savitski, M. M. et al. (2010). *Journal of the American Society for Mass Spectrometry*, 21: 1668-1679). Reporter ion intensities were multiplied with the ion accumulation time yielding an area value proportional to the number of reporter ions present in the mass analyser. Peptide fold changes were corrected for isotope purity as described and adjusted for interference caused by co-eluting nearly isobaric peaks as estimated by the signal-to-interference measure (Savitski. M. M. et al. (2013). *Journal of proteome research*, 12: 3586-3598). Protein quantification was achieved using a sum-based bootstrap algorithm (Savitski, M. M. (2011). *Analytical chemistry*, 83: 8959-8967).

Assay for Repeat Expansion Transcripts

Reverse transcription was performed using 1 µg total RNA from compound-treated and untreated cells. PCR was carried out using ½0 of the synthesized cDNA with primers N11, 5'-CACTGTCGGACATTCGGGAAGGTGC (SEQ ID NO: 3) and 133, 5'GCTTGCACGTGTGGCT-CAAGCAGCTG (SEQ ID NO: 4). For Genescan analysis primer N11 was labelled with FAM. Amplification was performed with a Tm of 58° C. The PCR product was subsequently heated to 95° C. for 2 minutes followed by cooling to 4° C. For BpmI restriction digestion analysis of DMPK PCR products, 8 µl of PCR mixture was digested overnight with restriction enzyme BpmI (NEB) in a total reaction volume of 20 µl at 37° C. The final products were analysed by electrophoresis at 90V with 3% agarose gels and the density of bands quantified using ImageJ software or by fragment analysis on an AB1377 sequencer followed by Genescan quantification.

Western Blots and Detection

Western blotting was performed using a commercial NuPage system (Invitrogen, UK) according to the manufacturer's instructions. The primary antibodies used in this study were human CDK9 (Abcam, 1:1000 dilution), human CDK12 (Abcam, 1:400 dilution), human a-tubulin and human Lamin B (both obtained from Santa Cruz and used at dilutions of 1:500). Anti-mouse IgG-horseradish peroxidise (HRP) was used as the secondary antibody. ImageJ software was used for the quantification of bands on western blots.

Colocalisation Studies

Cells were grown on coverslips for 24 hours before being fixed and permeabilised with 50:50 ice cold acetone:methanol. Cells were blocked in 5% BSA with 5% sheep serum. Anti-CDK12 antibody (Abcam) was used at 1:1000 dilution at 4° C. overnight followed by staining with Alexafluor-488 anti-mouse secondary antibody (1:500). Cells were incubated in 4% PFA for 5 minutes, followed by 15 minutes in pre-hybridisation solution (40% formamide, 10% 20×SSC, 50% DEPC water) and incubated with a cy3 labelled CAGio probe overnight at 37° C. Coverslips were mounted on slides using Vectorshield Mounting Media with DAPI. Images were acquired using a Zeiss 710 confocal microscope and analysed using LSM image browser.

siRNA Synthesis

The siRNA oligonucleotides were synthesized on an ABI 394 DNA/RNA synthesizer. Columns (SynBase™ CPG 1000 Å, RNA: 0.2 µmol), standard 2'-OTBDMS RNA-phosphoramidites and reagents for the synthesizer were purchased from Link Technologies Ltd., MeNH$_2$ solution (33 wt. % in ethanol) was obtained from Fluka, NEt$_3$.3HF, N-methylpyrrolidinone (NMP) were purchased from Aldrich, illustra Nap™-10 columns were obtained from GE Healthcare Europe GmbH. Dichloromethane and acetonitrile were freshly distilled from CaH$_2$ before use on the synthesizer.

The siRNA oligonucleotides were synthesized using a standard 0.2 µM scale protocol, but with a 10 min coupling time for each nucleotide addition step. The polymer-bound oligoribonucleotide was transferred from the synthesis column to a 1.5 mL microfuge tube and suspended in MeNH$_2$ solution (1 mL). The mixture was heated to 65° C. for 10 min, cooled to room temperature (water/icebath) and centrifuged for 1 min (10 000 g). The supernatant was separated from the CPG beads, the beads were washed with RNase free water (2×0.25 mL), all supernatants were combined and dried (2 h under nitrogen stream, then freeze dried). The oligoribonucleotide was resuspended in anhydrous NEt$_3$.3HF/NEt$_3$/NMP solution (250 µl of a solution of 1.5 mL NMP, 750 µl NEt$_3$ and 1.0 mL NEt$_3$.3HF), heated to 65° C. for 1.5 h, cooled to room temperature and quenched with 3M NaOAc solution (25 µL). n-BuOH (1 mL) was added to the mixture, which was then thoroughly mixed, cooled to −70° C. for 1-2 h (dry ice) to encourage further precipitation and centrifuged for 30 min (4° C., 13 000 g). The supernatant was removed, the pellet washed with 70% EtOH (2×500 µL) and then dried in vacuo (30 min). The dry precipitate was dissolved in RNase free water (1 mL) and desalted using a Nap™-10 column following the standard protocol. The resulting solution was freeze dried overnight leaving the oligoribonucleotide as a white foam/powder.

CDK12 siRNA Knockdown

Scrambled: 5' ACGUGACACGUUCGGAGAAUU (SEQ ID NO: 5) and CDK12: 5' CGAAAUAAUGAU-GUUGGCACCAGUU (SEQ ID NO: 6) siRNA sequences. Cells were electroporated on day 1 and day 4 with 800 nM of scrambled or CDK12 siRNA using the Amaxa Nucleofector system. Cells were collected on day 7 for immunohistochemistry, in situ hybridisation and western blot analysis.

CDK12 shRNA Knockdown

Cells were plated at 40% confluency the day before infection in 96 well format. Lentiviral titre (SantaCruz sc-44343-V) was added at an MOI of 10 in 5 µg/ml polybrene diluted in DMEM media. Cells were spin inoculated by centrifugation at 2500 rpm for 30 minutes. Following 24 hours incubation the virus was removed and replaced with fresh DMEM media. The infection was repeated on day 4 and cells were collected on day 7 for immunohistochemistry and in situ hybridisation analysis.

```
CDK12 sequence
         10         20         30         40         50
MPNSERHGGK KDGSGGASGT LQPSSGGGSS NSRERHRLVS KHKRHKSKHS 60         70         80         90        100
KDMGLVTPEA ASLGTVIKPL VEYDDISSDS DTFSDDMAFK LDRRENDERR 110        120        130        140        150
GSDRSDRLHK HRHHQHRRSR DLLKAKQTEK EKSQEVSSKS GSMKDRISGS 160        170        180        190        200
SKRSNEETDD YGKAQVAKSS SKESRSSKLH KEKTRKEREL KSGHKDRSKS 210        220        230        240        250
HRKRETPKSY KTVDSPKRRS RSPHRKWSDS SKQDDSPSGA SYGQDYDLSP 260        270        280        290        300
SRSHTSSNYD SYKKSPGSTS RRQSVSPPYK EPSAYQSSTR SPSPYSRRQR 310        320        330        340        350
SVSPYSRRRS SSYERSGSYS GRSPSPYGRR RSSSPFLSKR SLSRSPLPSR 360        370        380        390        400
KSMKSRSRSP AYSRHSSSHS KKKRSSSRSR HSSISPVRLP LNSSLGAELS 410        420        430        440        450
RKKKERAAAA AAAKMDGKES KGSPVFLPRK ENSSVEAKDS GLESKKLPRS 460        470        480        490        500
VKLEKSAPDT ELVNVTHLNT EVKNSSDTGK VKLDENSEKH LVKDLKAQGT 510        520        530        540        550
RDSKPIALKE EIVTPKETET SEKETPPPLP TIASPPPPLP TTTPPPQTPP 560        570        580        590        600
LPPLPPIPAL PQQPPLPPSQ PAFSQVPASS TSTLPPSTHS KTSAVSSQAN 610        620        630        640        650
SQPPVQVSVK TQVSVTAAIP HLKTSTLPPL PLPPLLPGDD DMDSPKETLP 660        670        680        690        700
SKPVKKEKEQ RTRHLLTDLP LPPELPGGDL SPPDSPEPKA ITPPQQPYKK 710        720        730        740        750
RPKICCPRYG ERRQTESDWG KRCVDKFDII GIIGEGTYGQ VYKAKDKDTG 760        770        780        790        800
ELVALKKVRL DNEKEGFPIT AIREIKILRQ LIHRSVVNMK EIVTDKQDAL 810        820        830        840        850
DFKKDKGAFY LVFEYMDHDL MGLLESGLVH FSEDHIKSFM KQLMEGLEYC 860        870        880        890        900
HKKNFLHRDI KCSNILLNNS GQIKLADFGL ARLYNSEESR PYTNKVITLW 910        920        930        940        950
YRPPELLLGE ERYTPAIDVW SCGCILGELF TKKPIFQANL ELAQLELISR 960        970        980        990       1000
LCGSPCPAVW PDVIKLPYFN TMKPKKQYRR RLREEFSFIP SAALDLLDHM 1010       1020       1030       1040       1050
LTLDPSKRCT AEQTLQSDFL KDVELSKMAP PDLPHWQDCH ELWSKKRRRQ 1060       1070       1080       1090       1100
RQSGVVVEEP PPSKTSRKET TSGTSTEPVK NSSPAPPQPA PGKVESGAGD 1110       1120       1130       1140       1150
AIGLADITQQ LNQSELAVLL NLLQSQTDLS IPQMAQLLNI HSNPEMQQQL 1160       1170       1180       1190       1200
EALNQSISAL TEATSQQQDS ETMAPEESLK EAPSAPVILP SAEQTTLEAS 1210       1220       1230       1240       1250
STPADMQNIL AVLLSQLMKT QEPAGSLEEN NSDKNSGPQG PRRTPTMPQE 1260       1270       1280       1290       1300
EAAACPPHIL PPEKRPPEPP GPPPPPPPPP LVEGDLSSAP QELNPAVTAA 1310       1320       1330       1340       1350
LLQLLSQPEA EPPGHLPHEH QALRPMEYST RPRPNRTYGN TDGPETGFSA
```

```
            1360       1370       1380       1390       1400
       IDTDERNSGP ALTESLVQTL VKNRTFSGSL SHLGESSSYQ GTGSVQFPGD 1410       1420       1430       1440       1450
       QDLRFARVPL ALHPVVGQPF LKAEGSSNSV VHAETKLQNY GELGPGTTGA 1460       1470       1480       1490
       SSSGAGLHWG GPTQSSAYGK LYRGPTRVPP RGGRGRGVPY
```

The kinase domain of CDK12 is from amino acid position, 727-1020 (underlined). CDK12 has an additional C terminal domain extension that extends around the N and C terminal lobes and contacts bound ATP (underlined and italics). This is unique to CDK12 and is not present in CDK9.

The contact residues with ATP are Thr737, Lys756, Glu814, Met816 and Asp819 (highlighted by bold type)

```
       CDK12 transcript sequence
                                                          (SEQ ID NO: 1)
          1 gtgtgactgg gtctgtgtga gggagagagt gtgtgtggtg tggaggtgaa acggaggcaa 61 gaaaggggggc tacctcagga gcgagggaca aaggggggcgt gaggcaccta ggccgcggca 121 ccccggcgac aggaagccgt cctgaaccgg gctaccgggt aggggaaggg cccgcgtagt 181 cctcgcaggg ccccagagct ggagtcggct ccacagcccc gggccgtcgg cttctcactt 241 cctggacctc cccggcgccc gggcctgagg actggctcgg cggagggaga agaggaaaca 301 gacttgagca gctccccgtt gtctcgcaac tccactgccg aggaactctc atttcttccc 361 tcgctccttc accccccacc tcatgtagaa gggtgctgag gcgtcgggag ggaggaggag 421 cctgggctac cgtccctgcc ctccccaccc ccttcccggg gcgctttggt gggcgtggag 481 ttggggttgg gggggtgggt gggggttgct ttttggagtg ctggggaact ttttttccctt 541 cttcaggtca ggggaaaggg aatgcccaat tcagagagac atgggggcaa gaaggacggg 601 agtggaggag cttctggaac tttgcagccg tcatcgggag gcggcagctc taacagcaga 661 gagcgtcacc gcttggtatc gaagcacaag cggcataagt ccaaacactc caaagacatg 721 gggttggtga cccccgaagc agcatccctg ggcacagtta tcaaacctttt ggtggagtat 781 gatgatatca gctctgattc cgacaccttc tccgatgaca tggccttcaa actagaccga 841 agggagaacg acgaacgtcg tggatcagat cggagcgacc gcctgcacaa acatcgtcac 901 caccagcaca ggcgttcccg ggacttacta aaagctaaac agaccgaaaa agaaaaaagc 961 caagaagtct ccagcaagtc gggatcgatg aaggaccgga tatcgggaag ttcaaagcgt 1021 tcgaatgagg agactgatga ctatgggaag gcgcaggtag ccaaaagcag cagcaaggaa 1081 tccaggtcat ccaagctcca caaggagaag accaggaaag aacgggagct gaagtctggg 1141 cacaaagacc ggagtaaaag tcatcgaaaa agggaaacac ccaaaagtta caaacagtg 1201 gacagcccaa aacggagatc caggagcccc cacaggaagt ggtctgacag ctccaaacaa 1261 gatgatagcc cctcgggagc ttcttatggc caagattatg accttagtcc ctcacgatct 1321 catacctcga gcaattatga ctcctacaag aaaagtcctg gaagtacctc gagaaggcag 1381 tcggtcagtc ccccttacaa ggagccttcg gcctaccagt ccagcacccg gtcaccgagc 1441 ccctacagta ggcgacagag atctgtcagt ccctatagca ggagacggtc gtccagctac 1501 gaaagaagtg gctcttacag cgggcgatcc cccagtccct atggtcgaag gcggtccagc 1561 agcccttttcc tgagcaagcg gtctctgagt cggagtccac tccccagtag gaaatccatg 1621 aagtccagaa gtagaagtcc tgcatattca agacattcat cttctcatag taaaaagaag 1681 agatccagtt cacgcagtcg tcattccagt atctcacctg tcaggcttcc acttaattcc
```

-continued

```
1741  agtctgggag ctgaactcag taggaaaaag aaggaaagag cagctgctgc tgctgcagca
1801  aagatggatg gaaaggagtc caagggttca cctgtatttt tgcctagaaa agagaacagt
1861  tcagtagagg ctaaggattc aggtttggag tctaaaaagt tacccagaag tgtaaaattg
1921  gaaaaatctg ccccagatac tgaactggtg aatgtaacac atctaaacac agaggtaaaa
1981  aattcttcag atacagggaa agtaaagttg gatgagaact ccgagaagca tcttgttaaa
2041  gatttgaaag cacagggaac aagagactct aaacccatag cactgaaaga ggagattgtt
2101  actccaaagg agacagaaac atcagaaaag gagacccctc cacctcttcc cacaattgct
2161  tctcccccac cccctctacc aactactacc cctccacctc agacaccccc tttgccacct
2221  ttgcctccaa taccagctct tccacagcaa ccacctctgc ctccttctca gccagcattt
2281  agtcaggttc ctgcttccag tacttcaact ttgccccctt ctactcactc aaagacatct
2341  gctgtgtcct ctcaggcaaa ttctcagccc cctgtacagg tttctgtgaa gactcaagta
2401  tctgtaacag ctgctattcc acacctgaaa acttcaacgt tgcctccttt gcccctccca
2461  cccttattac ctggagatga tgacatggat agtccaaaag aaactcttcc ttcaaaacct
2521  gtgaagaaag agaaggaaca gaggacacgt cacttactca cagaccttcc tctccctcca
2581  gagctccctg gtggagatct gtctccccca gactctccag aaccaaaggc aatcacacca
2641  cctcagcaac catataaaaa gagaccaaaa atttgttgtc ctcgttatgg agaaagaaga
2701  caaacagaaa gcgactgggg gaaacgctgt gtggacaagt ttgacattat tgggattatt
2761  ggagaaggaa cctatggcca agtatataaa gccaaggaca agacacagg agaactagtg
2821  gctctgaaga aggtgagact agacaatgag aaagagggct tcccaatcac agccattcgt
2881  gaaatcaaaa tccttcgtca gttaatccac cgaagtgttg ttaacatgaa ggaaattgtc
2941  acagataaac aagatgcact ggatttcaag aaggacaaag gtgcctttta ccttgtattt
3001  gagtatatgg accatgactt aatgggactg ctagaatctg gtttggtgca cttttctgag
3061  gaccatatca agtcgttcat gaaacagcta atggaaggat tggaatactg tcacaaaaag
3121  aatttcctgc atcgggatat taagtgttct aacatttttgc tgaataacag tgggcaaatc
3181  aaactagcag attttggact tgctcggctc tataactctg aagagagtcg cccttacaca
3241  aacaaagtca ttactttgtg gtaccgacct ccagaactac tgctaggaga ggaacgttac
3301  acaccagcca tagatgtttg gagctgtgga tgtattcttg gggaactatt cacaaagaag
3361  cctatttttc aagccaatct ggaactggct cagctagaac tgatcagccg actttgtggt
3421  agcccttgtc cagctgtgtg gcctgatgtt atcaaactgc cctacttcaa caccatgaaa
3481  ccgaagaagc aatatcgaag gcgtctacga aagaattct ctttcattcc ttctgcagca
3541  cttgattat tggaccacat gctgacacta gatcctagta gcggtgcac agctgaacag
3601  accctacaga gcgacttcct taaagatgtc gaactcagca aaatggctcc tccagacctc
3661  ccccactggc aggattgcca tgagttgtgg agtaagaaac ggcgacgtca cgacaaagt
3721  ggtgttgtag tcgaagagcc acctccatcc aaaacttctc gaaaagaaac tacctcaggg
3781  acaagtactg agcctgtgaa gaacagcagc ccagcaccac ctcagcctgc tcctggcaag
3841  gtggagtctg gggctgggga tgcaataggc cttgctgaca tcacacaaca gctgaatcaa
3901  agtgaattgg cagtgttatt aaacctgctg cagagccaaa ccgacctgag catccctcaa
3961  atggcacagc tgcttaacat ccactccaac ccagagatgc agcagcagct ggaagccctg
4021  aaccaatcca tcagtgccct gacggaagct acttcccagc agcaggactc agagaccatg
4081  gccccagagg agtctttgaa ggaagcaccc tctgcccag tgatcctgcc ttcagcagaa
4141  cagacgaccc ttgaagcttc aagcacacca gctgacatgc agaatatatt ggcagttctc
```

-continued

```
4201  ttgagtcagc tgatgaaaac ccaagagcca gcaggcagtc tggaggaaaa caacagtgac
4261  aagaacagtg ggccacaggg gccccgaaga actcccacaa tgccacagga ggaggcagca
4321  gcatgtcctc ctcacattct tccaccagag aagaggcccc ctgagccccc cggacctcca
4381  ccgccgccac ctccaccccc tctggttgaa ggcgatcttt ccagcgcccc ccaggagttg
4441  aacccagccg tgacagccgc cttgctgcaa cttttatccc agcctgaagc agagcctcct
4501  ggccacctgc cacatgagca ccaggccttg agaccaatgg agtactccac ccgaccccgt
4561  ccaaacagga cttatggaaa cactgatggg cctgaaacag ggttcagtgc cattgacact
4621  gatgaacgaa actctggtcc agccttgaca gaatcctggt ccagaccct ggtgaagaac
4681  aggaccttct caggctctct gagccacctt ggggagtcca gcagttacca gggcacaggg
4741  tcagtgcagt ttccagggga ccaggacctc cgttttgcca gggtccccct tagcgttacac
4801  ccggtggtcg ggcaaccatt cctgaaggct gagggaagca gcaattctgt ggtacatgca
4861  gagaccaaat tgcaaaacta ggggagctg gggccaggaa ccactgggc cagcagctca
4921  ggagcaggcc ttcactgggg gggcccaact cagtcttctg cttatggaaa actctatcgg
4981  gggcctacaa gagtcccacc aagaggggga agagggagag gagttcctta ctaacccaga
5041  gacttcagtg tcctgaaaga ttcctttcct atccatcctt ccatccagtt ctctgaatct
5101  ttaatgaaat catttgccag agcgaggtaa tcatctgcat ttggctactg caaagctgtc
5161  cgttgtattc cttgctcact tgctactagc aggcgactta cgaaataatg atgttggcac
5221  cagttccccc tggatgggct atagccagaa catttacttc aactctacct tagtagatac
5281  aagtagagaa tatgagagag atcattacat tgaaaagtaa atgttttatt agttcattgc
5341  ctgcacttac tgatcggaag agagaaagaa cagtttcagt attgagatgg ctcaggagag
5401  gctctttgat ttttaaagtt ttggggtggg ggattgtgtg tggtttcttt cttttgaatt
5461  ttaatttagg tgttttgggt ttttttcctt taaagagaat agtgttcaca aaatttgagc
5521  tgctctttgg cttttgctat aagggaaaca gagtggcctg gctgatttga ataaatgttt
5581  cttttcctctc caccatctca cattttgctt ttaagtgaac acttttccc cattgagcat
5641  cttgaacata ctttttttcc aaataaatta ctcatcctta agtttactc cactttgaca
5701  aaagatacgc ccttctccct gcacataaag caggttgtag aacgtggcat cttgggcaa
5761  gtaggtagac tttacccagt ctctttcctt ttttgctgat gtgtgctctc tctctctctt
5821  tctctctctc tctctctctc tctctctctc tctctctctc tgtctcgctt gctcgctctc
5881  gctgtttctc tctctttgag gcatttgttt ggaaaaaatc gttgagatgc ccaagaacct
5941  gggataattc tttactttt ttgaaataaa ggaaaggaaa ttcagactct tacattgttc
6001  tctgtaactc ttcaattcta aaatgttttg tttttttaaac catgttctga tggggaagtt
6061  gatttgtaag tgtggacagc ttggacattg ctgctgagct gtggttagag atgatgcctc
6121  cattcctaga gggctaataa cagcatttag catattgttt acacatatat ttttatgtca
6181  aaaaaaaaac aaaaaccttt caaacagagc attgtgatat tgtcaaagag aaaaacaaat
6241  cctgaagata catggaaatg taacctagtt tagggtgggt atttttctga agatacatca
6301  atacctgacc tttttaaaaa aataatttt aaaacagcat actgtgagga agaacagtat
6361  tgacataccc acatcccagc atgtgtaccc tgccagttct tttagggatt tttcctccaa
6421  agagatttgg atttggtttt ggtaaaaggg gttaaattgt gcttccaggc aagaactttg
6481  ccttatcata aacaggaaat gaaaagggga agggctgtca ggatgggata attttgggagg
6541  cttctcattc tggcttctat ttctatgtga gtaccagcat atagagtgtt ttaaaaacag
```

```
6601  atacatgtca tataatttat ctgcacagac ttagacccttc aggaaacata ggttaagccc
6661  cctttacaa agaaaaagta acatacttc agcatcttgg agggtagttt tcaaaactca
6721  agtttcatgt ttcaatgcca agttcttatt ttaaaaaata aaatctactt ataagagaaa
6781  ggtgcattac ttaaaaaaaa aaaactttaa agaaatgaaa gaagaaccct cttcagatac
6841  ttacttgaag actgttttcc cctgttaatg agatatagct agatatcggt gtgtgtattt
6901  ctttattatt ctctggtttt tgatctggcc ttgcctccag ggccaaacac tgatttagaa
6961  agagagcctt ctagctattt tggcattgat ggcttttat accagtgtgt ccagttagat
7021  ttactaggct tactgacatg ctattggtaa atcgcattaa agttcatctg aaccttctgt
7081  ctgttgactt cttagtcctc agacatgggc ctttgtgttt tagaatattt gaatttgagt
7141  tattgggccc cactccctgt ttttattaa agaacgtgag cctgggatac tttcagaagt
7201  atctgttcaa tgaaaaaaag ttggtttccc atcaaatatg aataaaattc tctatatatt
7261  tcattgtatt ttggttatca gcagtcatca ataatgtttt tccctcccct ctcccacctc
7321  ttatttttaa ttatgccaaa tatcctaaat aatatactta agcctccatt ccctcatccc
7381  tactaggaa ggggtgagt gtatgtgtga gtgtatgtgt atgtatgatc ccatctcacc
7441  cccacccca ttttgggagt cttttaaaat gaaaacaaag tttggtagtt ttgactattt
7501  ctaaaagcag aggagaaaaa aaaacttatt taaatatcct ggaatctgta tggaggaaga
7561  aaaggtattt gttaattttt cagttacgtt atctataaac atgatggaag taaaggtttg
7621  gcagaatttc accttgacta tttgaaaatt acagacccaa ttaattccat tcaaaagtgg
7681  ttttcgtttt gttttaatta ttgtacaatg agagatattg tctattaaat acattatttt
7741  gaacagatga gaaatctgat tctgttcatg agtgggaggc aaaactggtt tgaccgtgat
7801  catttttgtg gttttgaaaa caaatatact tgacccagtt tccttagttt tttcttcaac
7861  tgtccatagg aacgataagt atttgaaagc aacatcaaat ctatacgttt aaagcagggc
7921  agttagcaca aatttgcaag tagaacttct attagcttat gccatagaca tcacccaacc
7981  acttgtatgt gtgtgtgtat atataatatg catatatagt taccgtgcta aaatggttac
8041  cagcaggttt tgagagagaa tgctgcatca gaaaagtgtc agttgccacc tcattctccc
8101  tgatttaggt tcctgacact gattcctttc tctctcgttt tgaccccca ttgggtgtat
8161  cttgtctatg tacagatatt ttgtaatata ttaaattttt ttctttcagt ttataaaaat
8221  ggaaagtgga gattggaaaa ttaaatattt cctgttacta taccacttttt gctccattgc
8281  att
```

The invention claimed is:

1. A method of treatment of a disorder caused by the generation of repeat expansion transcripts in a subject, comprising administering an inhibitor of CDK12 to the subject, wherein the disorder is selected from the group consisting of Myotonic Dystrophy type 1, Myotonic Dystrophy type 2, and frontotemporal dementia (C9ORF72).

2. The method according to claim 1, wherein the method further comprises a subsequent administration of at least one other therapeutic agent.

3. The method of claim 1, wherein the inhibitor is specific for CDK12, wherein the inhibitor is not an inhibitor of CDK9 activity or availability, or wherein the inhibitor comprises an inhibitor of CDK12 expression.

4. The method of claim 1, wherein the inhibitor comprises an oligonucleotide capable of inhibiting CDK12 expression.

5. The method of claim 4, wherein the oligonucleotide comprises a sequence complementary to CDK12 mRNA transcript.

6. The method of claim 1, wherein the inhibitor comprises a molecule capable of binding to CDK12 and/or capable of blocking binding of CDK12 to its target molecule.

7. The method of claim 1, wherein the inhibitor comprises a molecule capable of preventing CDK12 binding to cyclin K.

8. The method of claim 1, wherein the inhibitor comprises a molecule capable of preventing CDK12 phosphorylating Ser2 on the c-terminal domain of RNA polymerase II.

9. The method of claim 5, wherein the binding of the inhibitor to CDK12 is at, or adjacent to, the CDK12 active site, such that the active site is blocked.

10. The method of claim 5, wherein the binding of the inhibitor to CDK12 is at amino acid position, 727-1020.

11. The method of claim 5, wherein the binding of the inhibitor to CDK12 is at a C terminal domain extension that extends around the N and C terminal lobes and contacts bound ATP.

12. The method of claim 5, wherein the binding of the inhibitor to CDK12 is at any one or more of the ATP contact residues selected from Thr737, Lys756, Glu814, Met816 and Asp819.

13. The method of claim 1, wherein the inhibitor comprises a small molecule, oligonucleotide, peptide or protein capable of binding to CDK12.

14. The method of claim 1, wherein the inhibitor comprises a pyrazolo[1,5b]pyridazine core structure, and is capable of inhibiting CDK12 activity.

15. The method of claim 1, wherein the inhibitor comprises a compound of Formula (I) or a pharmaceutically acceptable salt or solvate thereof:

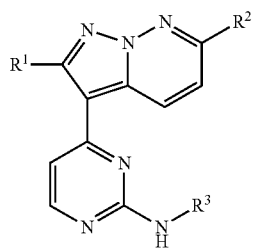

Formula I wherein:

$R^1$ is H, —OH, $C_{1-6}$alkyl, $C_{2-6}$alkenyl, $C_{2-6}$alkynl, $C_{1-6}$haloalkyl, halogen, —CN, —OC$_{1-6}$ alkyl;

$R^2$ is H, —OH, $C_{1-6}$alkyl, $C_{2-6}$alkenyl, $C_{2-6}$alkynl, $C_{1-6}$haloalkyl, halogen, —CN, —OC$_{1-6}$alkyl or a five or 6 membered cycloaryl, cycloalkyl or heterocycl having one, two or three heteroatoms selected from O, S and N;

$R^3$ is $C_{3-6}$cycloalkyl,

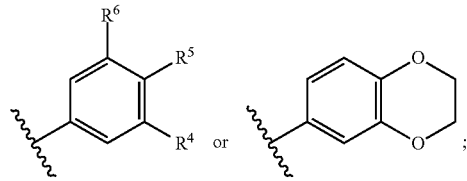

wherein:

$R^4$ is H, —OH, $C_{1-6}$alkyl, $C_{2-6}$alkenyl, $C_{2-6}$alkynl, $C_{1-6}$haloalkyl, halogen, —CN, —OC$_{1-6}$alkyl;

$R^5$ is H; —OH; $C_{1-6}$alkyl; $C_{2-6}$alkenyl; $C_{2-6}$alkynl; $C_{1-6}$haloalkyl; halogen; —CN; —OC$_{1-6}$alkyl; —; $C_{1-6}$alkyl-N—(X)(Y); a five or six membered cycloaryl, cycloalkyl or heterocycl having one, two or three heteroatoms selected from O, S and N and said cycloaryl, cycloalkyl or heterocycle being optionally substituted with a $C_{1-3}$alkyl or —OC$_{1-6}$alkyl-N(X)(Y);

wherein X is H or $C_{1-6}$alkyl, and Y is H or $C_{1-6}$alkyl;

and wherein the alkyl groups are optionally substituted by one or more —OH groups; and $R^6$ is H, —OH, $C_{1-6}$alkyl, $C_{2-6}$alkenyl, $C_{2-6}$alkynl, $C_{1-6}$haloalkyl, halogen, —CN, —OC$_{1-6}$alkyl.

16. The method of claim 15, wherein:
$R^1$ is H;
$R^2$ is H;
$R^3$ is $C_{3-6}$cycloalkyl,

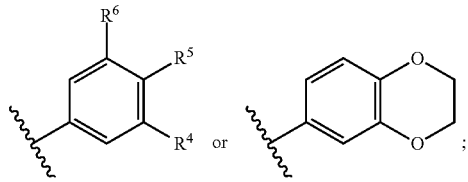

wherein:
$R^4$ is H, —CN, —OC$_{1-6}$alkyl, $C_{1-6}$haloalkyl;
$R^5$ is H, $C_{1-6}$alkyl-N—(X)(Y); a five or six membered cycloaryl, cycloalkyl or heterocycl having one, two or three heteroatoms selected from O, S and N and said cycloaryl, cycloalkyl or heterocycle being optionally substituted with a $C_{1-3}$alkyl or —OC$_{1-6}$alkyl-N(X)(Y);
wherein X is H or $C_{1-6}$alkyl, and Y is H or $C_{1-6}$alkyl;
and wherein the alkyl groups are optionally substituted by one or more —OH groups; and
$R^6$ is H or —OC$_{1-6}$alkyl.

17. The method of claim 15, wherein:
$R^1$ is H;
$R^2$ is H;
$R^3$ is cyclopropyl,

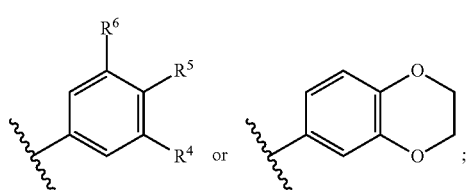

wherein:
$R^4$ is H, —CN, —OCH$_3$, CF$_3$;
$R^5$ is H, —CH$_2$N(CH$_3$)$_2$, N-methylpiperazinyl, —OCH$_2$CH(OH)CH$_2$N(CH$_3$)$_2$; and
$R^6$ is H or —OCH$_3$.

18. The method of claim 15, wherein:
$R^1$ is H,
$R^2$ is H,
$R^3$ is cyclopropyl,

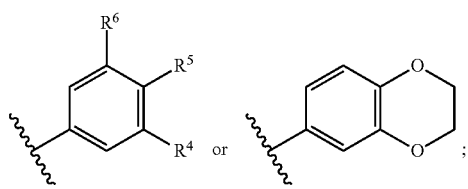

wherein:
$R^4$ is H; $R^5$ is —CH$_2$NEt$_2$, or —OCH$_2$CH(OH)CH$_2$N(CH$_3$)$_2$; and $R^6$ is H; or
$R^4$ is —CN, —OCH$_3$; $R^5$ is H; and $R^6$ is H; or
$R^4$ is —CF$_3$; $R^5$ is N-methylpiperazinyl; and $R^6$ is H; or
$R^4$ is —OCH$_3$; $R^5$ is H; and $R^6$ is —OCH$_3$.

19. The method of claim 15, wherein the inhibitor of Formula (I) is one of the following formula or a pharmaceutically acceptable salt or solvate thereof:

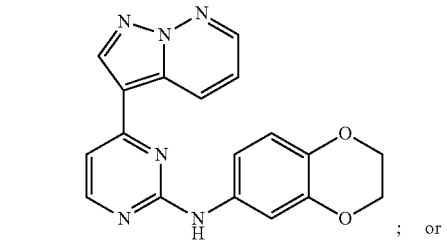
(II)

; or

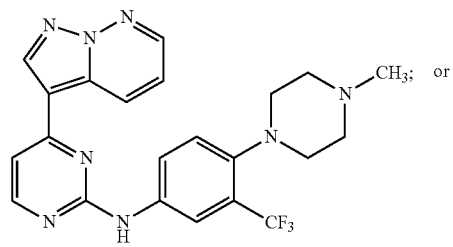
(III)

; or

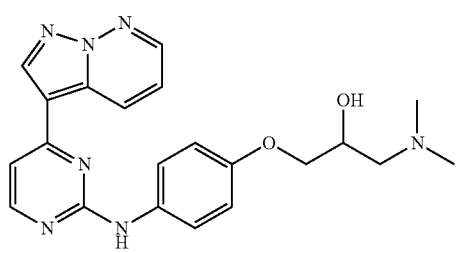
(IV)

; or

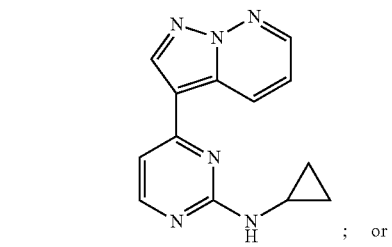
(V)

; or

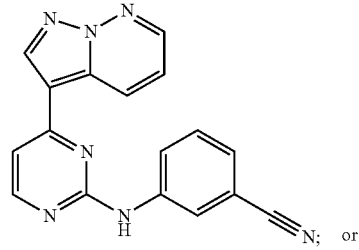
(VI)

; or

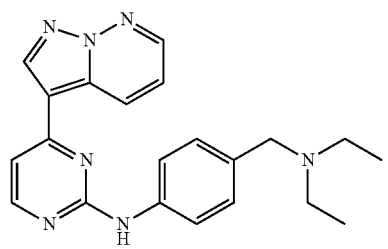
(VII)

; or

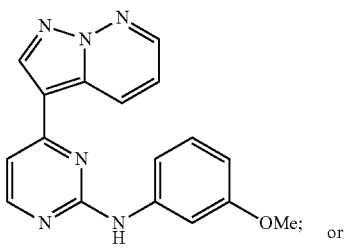
(VIII)

; or

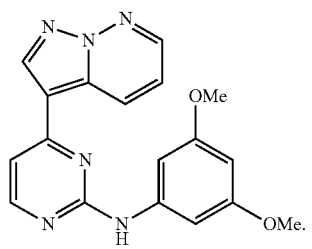
(IX)

.

20. The method of claim 1, wherein the inhibitor comprises a compound of one of the following Formula or a pharmaceutically acceptable salt or solvate thereof:

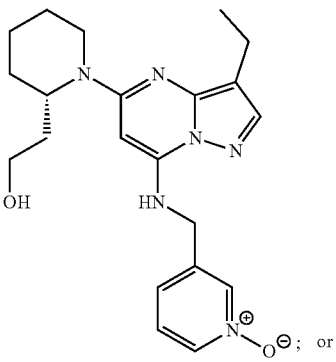
(X)

SCH 727965
(dinaciclib)

; or

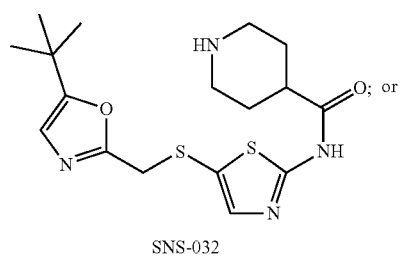
(XI)

SNS-032

-continued

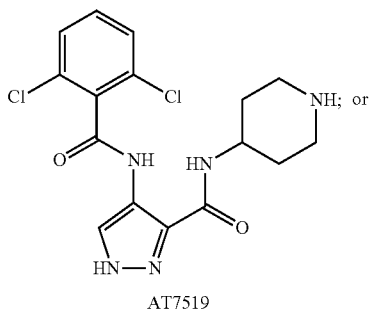

AT7519

(XII)

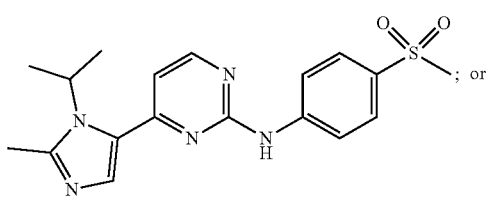

AZD 5438

(XIII)

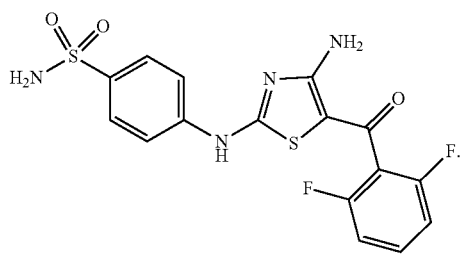

SB-498806

(XIV)

21. The method of claim 1, wherein the inhibitor is further administered, or arranged to be further administered in combination with at least one other therapeutic agent.

22. The method of claim 21, wherein the one other therapeutic agent comprises an oligonucleotide; or wherein the at least one other therapeutic agent may comprise a small molecule, drug, pro-drug, peptide, protein, antibody, nucleotide or vaccine; or wherein the at least one other therapeutic agent comprises a sodium channel blocker; a CNS stimulant drug; dehydroepiandrosterone (DHEA); creatine supplementation; mecasermin rinfabate (IPLEX, combination of recombinant insulin-like growth factor 1 and its binding protein, BP-3); pentamidine; a bisamidinium inhibitor; lomofugin; or dilomofungin; or combinations thereof.

23. The method of claim 1, wherein the use is further in combination with an oligonucleotide that targets the DMPK gene.

24. The method of claim 1, wherein the inhibitor is administered intermittently.

25. The method of claim 22, wherein the oligonucleotide comprises siRNA and miRNA.

26. The method of claim 15, wherein $R^2$ is benzene, morpholinyl, piperidine, or piperazine.

27. The method of claim 15 or claim 16, wherein $R^3$ is cyclopropyl.

28. The method of claim 15, wherein the alkyl groups of $R^5$ are optionally substituted by one or more —OH groups.

29. The method of claim 16, wherein $R^5$ is N-methylpiperazinyl, —$OC_{1-6}$alkyl-N(X)(Y).

* * * * *

SEQUENCE LISTING

<160> NUMBER OF SEQ ID NOS: 6

<210> SEQ ID NO 1
<211> LENGTH: 8283
<212> TYPE: DNA
<213> ORGANISM: Homo sapiens

<400> SEQUENCE: 1

```
gtgtgactgg gtctgtgtga gggagagagt gtgtgtggtg tggaggtgaa acggaggcaa      60
gaaaggggc tacctcagga gcgagggaca aaggggggcgt gaggcaccta ggccgcggca     120
ccccggcgac aggaagccgt cctgaaccgg gctaccgggt aggggaaggg cccgcgtagt     180
cctcgcaggg ccccagagct ggagtcggct ccacagcccc gggccgtcgg cttctcactt     240
```

```
cctggacctc cccggcgccc gggcctgagg actggctcgg cggagggaga agaggaaaca    300
gacttgagca gctccccgtt gtctcgcaac tccactgccg aggaactctc atttcttccc    360
tcgctccttc acccccacc tcatgtagaa gggtgctgag gcgtcgggag ggaggaggag    420
cctgggctac cgtccctgcc ctccccaccc ccttcccggg gcgctttggt gggcgtggag    480
ttggggttgg gggggtgggt ggggggttgct ttttggagtg ctggggaact ttttttcctt    540
cttcaggtca ggggaaaggg aatgcccaat tcagagagac atgggggcaa gaaggacggg    600
agtggaggag cttctggaac tttgcagccg tcatcgggag gcggcagctc taacagcaga    660
gagcgtcacc gcttggtatc gaagcacaag cggcataagt ccaaacactc caaagacatg    720
gggttggtga cccccgaagc agcatccctg ggcacagtta tcaaaccttt ggtggagtat    780
gatgatatca gctctgattc cgacaccttc tccgatgaca tggccttcaa actagaccga    840
agggagaacg acgaacgtcg tggatcagat cggagcgacc gcctgcacaa acatcgtcac    900
caccagcaca ggcgttcccg ggacttacta aaagctaaac agaccgaaaa agaaaaaagc    960
caagaagtct ccagcaagtc gggatcgatg aaggaccgga tatcgggaag ttcaaagcgt   1020
tcgaatgagg agactgatga ctatgggaag gcgcaggtag ccaaaagcag cagcaaggaa   1080
tccaggtcat ccaagctcca caaggagaag accaggaaaa aacgggagct gaagtctggg   1140
cacaaagacc ggagtaaaag tcatcgaaaa agggaaacac ccaaaagtta caaaacagtg   1200
gacagcccaa aacggagatc caggagcccc cacaggaagt ggtctgacag ctccaaacaa   1260
gatgatagcc cctcgggagc ttcttatggc caagattatg accttagtcc ctcacgatct   1320
catacctcga gcaattatga ctcctacaag aaaagtcctg gaagtacctc gagaaggcag   1380
tcggtcagtc ccccttacaa ggagccttcg gcctaccagt ccagcacccg gtcaccgagc   1440
ccctacagta ggcgacagag atctgtcagt ccctatagca ggagacggtc gtccagctac   1500
gaaagaagtg gctcttacag cgggcgatcg cccagtccct atggtcgaag gcggtccagc   1560 agcccttttcc tgagcaagcg gtctctgagt cggagtccac tccccagtag gaaatccatg   1620
aagtccagaa gtagaagtcc tgcatattca agacattcat cttctcatag taaaaagaag   1680
agatccagtt cacgcagtcg tcattccagt atctcacctg tcaggcttcc acttaattcc   1740
agtctgggag ctgaactcag taggaaaaag aaggaaagag cagctgctgc tgctgcagca   1800
aagatggatg gaaggagtc caagggttca cctgtatttt tgcctagaaa agagaacagt   1860
tcagtagagg ctaaggattc aggtttggag tctaaaaagt tacccagaag tgtaaaattg   1920
gaaaaatctg ccccagatac tgaactggtg aatgtaacac atctaaacac agaggtaaaa   1980
aattcttcag atacagggaa agtaaagttg gatgagaact ccgagaagca tcttgttaaa   2040
gatttgaaag cacagggaac aagagactct aaacccatag cactgaaaga ggagattgtt   2100
actccaaagg agacagaaac atcagaaaag gagacccctc cacctcttcc cacaattgct   2160
tctcccccac cccctctacc aactactacc cctccacctc agacaccccc tttgccacct   2220
ttgcctccaa taccagctct tccacagcaa ccacctctgc ctccttctca gccagcattt   2280
agtcaggttc ctgcttccag tacttcaact ttgcccccctt ctactcactc aaagacatct   2340
gctgtgtcct ctcaggcaaa ttctcagccc cctgtacagg tttctgtgaa gactcaagta   2400
tctgtaacag ctgctattcc acacctgaaa acttcaacgt tgcctccttt gcccctccca   2460
cccttattac ctggagatga tgacatggat agtccaaaag aaactcttcc ttcaaaacct   2520
gtgaagaaag agaaggaaca gaggacacgt cacttactca cagaccttcc tctccctcca   2580 gagctcccctg gtggagatct gtctccccca gactctccag aaccaaaggc aatcacacca   2640
```

```
cctcagcaac catataaaaa gagaccaaaa atttgttgtc ctcgttatgg agaaagaaga   2700
caaacagaaa gcgactgggg gaaacgctgt gtggacaagt ttgacattat tgggattatt   2760
ggagaaggaa cctatggcca agtatataaa gccaaggaca agacacagg agaactagtg    2820 gctctgaaga aggtgagact agacaatgag aaagagggct tcccaatcac agccattcgt   2880
gaaatcaaaa tccttcgtca gttaatccac cgaagtgttg ttaacatgaa ggaaattgtc   2940
acagataaac aagatgcact ggatttcaag aaggacaaag gtgcctttta ccttgtattt   3000
gagtatatgg accatgactt aatgggactg ctagaatctg gtttggtgca cttttctgag   3060
gaccatatca agtcgttcat gaaacagcta atggaaggat tggaatactg tcacaaaaag   3120
aatttcctgc atcgggatat taagtgttct aacattttgc tgaataacag tgggcaaatc   3180
aaactagcag attttggact tgctcggctc tataactctg aagagagtcg cccttacaca   3240
aacaaagtca ttactttgtg gtaccgacct ccagaactac tgctaggaga ggaacgttac   3300
acaccagcca tagatgtttg gagctgtgga tgtattcttg gggaactatt cacaaagaag   3360 cctattttc aagccaatct ggaactggct cagctagaac tgatcagccg actttgtggt   3420
agcccttgtc cagctgtgtg gcctgatgtt atcaaactgc cctacttcaa caccatgaaa   3480
ccgaagaagc aatatcgaag gcgtctacga gaagaattct ctttcattcc ttctgcagca   3540
cttgatttat tggaccacat gctgacacta gatcctagta agcggtgcac agctgaacag   3600
accctacaga gcgacttcct taaagatgtc gaactcagca aaatggctcc tccagacctc   3660
ccccactggc aggattgcca tgagttgtgg agtaagaaac ggcgacgtca gcgacaaagt   3720
ggtgttgtag tcgaagagcc acctccatcc aaaacttctc gaaaagaaac tacctcaggg   3780
acaagtactg agcctgtgaa gaacagcagc ccagcaccac ctcagcctgc tcctggcaag   3840
gtggagtctg gggctgggga tgcaataggc cttgctgaca tcacacaaca gctgaatcaa   3900
agtgaattgg cagtgttatt aaacctgctg cagagccaaa ccgacctgag catccctcaa   3960
atggcacagc tgcttaacat ccactccaac ccagagatgc agcagcagct ggaagccctg   4020
aaccaatcca tcagtgccct gacggaagct acttcccagc agcaggactc agagaccatg   4080
gccccagagg agtctttgaa ggaagcaccc tctgccccag tgatcctgcc ttcagcagaa   4140
cagacgaccc ttgaagcttc aagcacacca gctgacatgc agaatatatt ggcagttctc   4200
ttgagtcagc tgatgaaaac ccaagagcca gcaggcagtc tggaggaaaa caacagtgac   4260
aagaacagtg ggcccagggg gccccgaaga actcccacaa tgccacagga ggaggcagca   4320
gcatgtcctc ctcacattct tccaccagag aagaggcccc ctgagccccc ggacctcca    4380 ccgccgccac ctccaccccc tctggttgaa ggcgatcttt ccagcgcccc ccaggagttg   4440
aacccagccg tgacagccgc cttgctgcaa cttttatccc agcctgaagc agagcctcct   4500
ggccacctgc cacatgagca ccaggccttg agaccaatgg agtactccac ccgaccccgt   4560
ccaaacagga cttatggaaa cactgatggg cctgaaacag ggtcagtgc cattgacact    4620 gatgaacgaa actctggtcc agccttgaca gaatccttgg tccagaccct ggtgaagaac   4680
aggaccttct caggctctct gagccacctt ggggagtcca gcagttacca gggcacaggg   4740
tcagtgcagt ttcaggggga ccaggacctc cgttttgcca gggtcccctt agcgttacac   4800
ccggtggtcg ggcaaccatt cctgaaggct gagggaagca gcaattctgt ggtacatgca   4860
gagaccaaat tgcaaaacta tgggagctg gggccaggaa ccactgggc cagcagctca    4920 ggagcaggcc ttcactgggg gggcccaact cagtcttctg cttatggaaa actctatcgg   4980
```

```
gggcctacaa gagtcccacc aagagggga agagggagag gagttcctta ctaacccaga    5040
gacttcagtg tcctgaaaga ttcctttcct atccatcctt ccatccagtt ctctgaatct    5100
ttaatgaaat catttgccag agcgaggtaa tcatctgcat ttggctactg caaagctgtc    5160
cgttgtattc cttgctcact tgctactagc aggcgactta cgaaataatg atgttggcac    5220
cagttccccc tggatgggct atagccagaa catttacttc aactctacct tagtagatac    5280
aagtagagaa tatggagagg atcattacat tgaaaagtaa atgttttatt agttcattgc    5340
ctgcacttac tgatcggaag agagaaagaa cagtttcagt attgagatgg ctcaggagag    5400
gctctttgat ttttaaagtt ttggggtggg ggattgtgtg tggttctttt cttttgaatt    5460
ttaatttagg tgttttgggt ttttttcctt taaagagaat agtgttcaca aaatttgagc    5520
tgctctttgg cttttgctat aagggaaaca gagtggcctg gctgatttga ataaatgttt    5580
cttcctctc caccatctca catttgctt ttaagtgaac acttttcccc cattgagcat    5640
cttgaacata ctttttttcc aaataaatta ctcatcctta aagttactc cactttgaca    5700
aaagatacgc ccttctccct gcacataaag caggttgtag aacgtggcat tcttgggcaa    5760
gtaggtagac tttacccagt ctctttcctt ttttgctgat gtgtgctctc tctctctctt    5820
tctctctctc tctctctctc tctctctctc tctctctctc tgtctcgctt gctcgctctc    5880
gctgtttctc tctctttgag gcatttgttt ggaaaaaatc gttgagatgc ccaagaacct    5940
gggataattc tttactttt tgaaataaa ggaaggaa ttcagactct acattgttc    6000
tctgtaactc ttcaattcta aaatgttttg ttttttaaac catgttctga tggggaagtt    6060
gatttgtaag tgtggacagc ttggacattg ctgctgagct gtggttagag atgatgcctc    6120
cattcctaga gggctaataa cagcatttag catattgttt acacatatat ttttatgtca    6180
aaaaaaaac aaaacctt caaacagagc attgtgtatat tgtcaaagag aaaaacaaat    6240
cctgaagata catggaaatg taacctagtt tagggtgggt atttttctga agatacatca    6300
atacctgacc tttttaaaa aaataatttt aaaacagcat actgtgagga agaacagtat    6360
tgacataccc acatcccagc atgtgtaccc tgccagttct tttagggatt tttcctccaa    6420
agagatttgg atttggtttt ggtaaaaggg gttaaattgt gcttccaggc aagaactttg    6480
ccttatcata aacaggaaat gaaaaaggga agggctgtca ggatgggata atttgggagg    6540
cttctcattc tggcttctat ttctatgtga gtaccagcat atagagtgtt ttaaaaacag    6600
atacatgtca tataatttat ctgcacagac ttagaccttc aggaaacata ggttaagccc    6660
cctttacaa agaaaagta aacatacttc agcatcttgg agggtagttt tcaaaactca    6720
agtttcatgt ttcaatgcca agttcttatt ttaaaaata aaatctactt ataagagaaa    6780
ggtgcattac ttaaaaaaa aaaacttaa agaaatgaaa gaagaaccct ttcagatac    6840
ttacttgaag actgttttcc cctgttaatg agatatagct agatatcggt gtgtgtattt    6900
ctttattatt ctctggtttt tgatctggcc ttgcctccag ggccaaacac tgatttagaa    6960
agagagcctt ctagctattt tggcattgat ggcttttat accagtgtgt ccagttagat    7020
ttactaggct tactgacatg ctattggtaa atcgcattaa agttcatctg aaccttctgt    7080
ctgttgactt cttagtcctc agacatgggc cttttgtgttt tagaatatt gaatttgagt    7140
tattgggccc cactccctgt tttttattaa agaacgtgag cctgggatac tttcagaagt    7200
atctgttcaa tgaaaaaag ttggtttccc atcaaatatg aataaaattc tctatatatt    7260
tcattgtatt ttggttatca gcagtcatca ataatgtttt tccctccct ctcccacctc    7320
ttattttaa ttatgccaaa tatcctaaat aatatactta agcctccatt ccctcatccc    7380
```

-continued

```
tactagggaa gggggtgagt gtatgtgtga gtgtatgtgt atgtatgatc ccatctcacc    7440
cccaccccca ttttgggagt cttttaaaat gaaaacaaag tttggtagtt ttgactattt    7500
ctaaaagcag aggagaaaaa aaaacttatt taaatatcct ggaatctgta tggaggaaga    7560
aaaggtattt gttaattttt cagttacgtt atctataaac atgatggaag taaaggtttg    7620
gcagaatttc accttgacta tttgaaaatt acagacccaa ttaattccat tcaaaagtgg    7680
ttttcgtttt gttttaatta ttgtacaatg agagatattg tctattaaat acattatttt    7740
gaacagatga gaaatctgat tctgttcatg agtgggaggc aaaactggtt tgaccgtgat    7800 cattttgtg gttttgaaaa caaatatact tgacccagtt tccttagttt tttcttcaac    7860
tgtccatagg aacgataagt atttgaaagc aacatcaaat ctatacgttt aaagcagggc    7920
agttagcaca aatttgcaag tagaacttct attagcttat gccatagaca tcacccaacc    7980
acttgtatgt gtgtgtgtat atataatatg catatatagt taccgtgcta aaatggttac    8040
cagcaggttt tgagagagaa tgctgcatca gaaaagtgtc agttgccacc tcattctccc    8100
tgatttaggt tcctgacact gattcctttc tctctcgttt ttgaccccca ttgggtgtat    8160
cttgtctatg tacagatatt ttgtaatata ttaaatttt ttctttcagt ttataaaaat    8220
ggaaagtgga gattggaaaa ttaaatattt cctgttacta taccactttt gctccattgc    8280
att                                                                 8283
```

<210> SEQ ID NO 2
<211> LENGTH: 1490
<212> TYPE: PRT
<213> ORGANISM: Homo sapiens

<400> SEQUENCE: 2

```
Met Pro Asn Ser Glu Arg His Gly Gly Lys Lys Asp Gly Ser Gly Gly
1               5                   10                  15

Ala Ser Gly Thr Leu Gln Pro Ser Gly Gly Gly Ser Ser Asn Ser
            20                  25                  30

Arg Glu Arg His Arg Leu Val Ser Lys His Lys Arg His Lys Ser Lys
        35                  40                  45

His Ser Lys Asp Met Gly Leu Val Thr Pro Glu Ala Ala Ser Leu Gly
    50                  55                  60

Thr Val Ile Lys Pro Leu Val Glu Tyr Asp Asp Ile Ser Ser Asp Ser
65                  70                  75                  80

Asp Thr Phe Ser Asp Asp Met Ala Phe Lys Leu Asp Arg Arg Glu Asn
                85                  90                  95

Asp Glu Arg Arg Gly Ser Asp Arg Ser Asp Arg Leu His Lys His Arg
            100                 105                 110

His His Gln His Arg Arg Ser Arg Asp Leu Leu Lys Ala Lys Gln Thr
        115                 120                 125

Glu Lys Glu Lys Ser Gln Glu Val Ser Ser Lys Ser Gly Ser Met Lys
    130                 135                 140

Asp Arg Ile Ser Gly Ser Ser Lys Arg Ser Asn Glu Glu Thr Asp Asp
145                 150                 155                 160

Tyr Gly Lys Ala Gln Val Ala Leu Ser Ser Lys Glu Ser Arg Ser
                165                 170                 175

Ser Lys Leu His Lys Glu Lys Thr Arg Lys Glu Arg Glu Leu Lys Ser
            180                 185                 190

Gly His Lys Asp Arg Ser Lys Ser His Arg Lys Arg Glu Thr Pro Lys
        195                 200                 205
```

```
Ser Tyr Lys Thr Val Asp Ser Pro Lys Arg Arg Ser Arg Ser Pro His
    210                 215                 220
Arg Lys Trp Ser Asp Ser Ser Lys Gln Asp Ser Pro Ser Gly Ala
225                 230                 235                 240
Ser Tyr Gly Gln Asp Tyr Asp Leu Ser Pro Ser Arg Ser His Thr Ser
                245                 250                 255
Ser Asn Tyr Asp Ser Tyr Lys Lys Ser Pro Gly Ser Thr Ser Arg Arg
            260                 265                 270
Gln Ser Val Ser Pro Pro Tyr Lys Glu Pro Ser Ala Tyr Gln Ser Ser
        275                 280                 285
Thr Arg Ser Pro Ser Pro Tyr Ser Arg Arg Gln Arg Ser Val Ser Pro
    290                 295                 300
Tyr Ser Arg Arg Ser Ser Ser Tyr Glu Arg Ser Gly Ser Tyr Ser
305                 310                 315                 320
Gly Arg Ser Pro Ser Pro Tyr Gly Arg Arg Ser Ser Ser Pro Phe
                325                 330                 335
Leu Ser Lys Arg Ser Leu Ser Arg Ser Pro Leu Pro Ser Arg Lys Ser
            340                 345                 350
Met Lys Ser Arg Ser Arg Ser Pro Ala Tyr Ser Arg His Ser Ser Ser
        355                 360                 365
His Ser Lys Lys Lys Arg Ser Ser Arg Ser Arg His Ser Ser Ile
    370                 375                 380
Ser Pro Val Arg Leu Pro Leu Asn Ser Ser Leu Gly Ala Glu Leu Ser
385                 390                 395                 400
Arg Lys Lys Lys Glu Arg Ala Ala Ala Ala Ala Ala Lys Met Asp
                405                 410                 415
Gly Lys Glu Ser Lys Gly Ser Pro Val Phe Leu Pro Arg Lys Glu Asn
            420                 425                 430
Ser Ser Val Glu Ala Lys Asp Ser Gly Leu Glu Ser Lys Lys Leu Pro
        435                 440                 445
Arg Ser Val Lys Leu Glu Lys Ser Ala Pro Asp Thr Glu Leu Val Asn
    450                 455                 460
Val Thr His Leu Asn Thr Glu Val Lys Asn Ser Ser Asp Thr Gly Lys
465                 470                 475                 480
Val Lys Leu Asp Glu Asn Ser Glu Lys His Leu Val Lys Asp Leu Lys
                485                 490                 495
Ala Gln Gly Thr Arg Asp Ser Lys Pro Ile Ala Leu Lys Glu Glu Ile
            500                 505                 510
Val Thr Pro Lys Glu Thr Glu Thr Ser Glu Lys Glu Thr Pro Pro
        515                 520                 525
Leu Pro Thr Ile Ala Ser Pro Pro Leu Pro Thr Thr Thr Pro
    530                 535                 540
Pro Pro Gln Thr Pro Pro Leu Pro Pro Leu Pro Ile Pro Ala Leu
545                 550                 555                 560
Pro Gln Gln Pro Pro Leu Pro Pro Ser Gln Pro Ala Phe Ser Gln Val
                565                 570                 575
Pro Ala Ser Ser Thr Ser Thr Leu Pro Pro Ser Thr His Ser Lys Thr
            580                 585                 590
Ser Ala Val Ser Ser Gln Ala Asn Ser Gln Pro Pro Val Gln Val Ser
        595                 600                 605
Val Lys Thr Gln Val Ser Val Thr Ala Ala Ile Pro His Leu Lys Thr
    610                 615                 620
```

```
Ser Thr Leu Pro Pro Leu Pro Leu Pro Pro Leu Leu Pro Gly Asp Asp
625                 630                 635                 640

Asp Met Asp Ser Pro Lys Glu Thr Leu Pro Ser Lys Pro Val Lys Lys
            645                 650                 655

Glu Lys Glu Gln Arg Thr Arg His Leu Leu Thr Asp Leu Pro Leu Pro
                660                 665                 670

Pro Glu Leu Pro Gly Gly Asp Leu Ser Pro Pro Asp Ser Pro Glu Pro
            675                 680                 685

Lys Ala Ile Thr Pro Pro Gln Pro Tyr Lys Lys Arg Pro Lys Ile
    690                 695                 700

Cys Cys Pro Arg Tyr Gly Glu Arg Arg Gln Thr Glu Ser Asp Trp Gly
705                 710                 715                 720

Lys Arg Cys Val Asp Lys Phe Asp Ile Gly Ile Ile Gly Glu Gly
                725                 730                 735

Thr Tyr Gly Gln Val Tyr Lys Ala Lys Asp Lys Asp Thr Gly Glu Leu
            740                 745                 750

Val Ala Leu Lys Lys Val Arg Leu Asp Asn Glu Lys Glu Gly Phe Pro
                755                 760                 765

Ile Thr Ala Ile Arg Glu Ile Lys Ile Leu Arg Gln Leu Ile His Arg
    770                 775                 780

Ser Val Val Asn Met Lys Glu Ile Val Thr Asp Lys Gln Asp Ala Leu
785                 790                 795                 800

Asp Phe Lys Lys Asp Lys Gly Ala Phe Tyr Leu Val Phe Glu Tyr Met
                805                 810                 815

Asp His Asp Leu Met Gly Leu Leu Glu Ser Gly Leu Val His Phe Ser
            820                 825                 830

Glu Asp His Ile Lys Ser Phe Met Lys Gln Leu Met Glu Gly Leu Glu
            835                 840                 845

Tyr Cys His Lys Lys Asn Phe Leu His Arg Asp Ile Lys Cys Ser Asn
            850                 855                 860

Ile Leu Leu Asn Asn Ser Gly Gln Ile Lys Leu Ala Asp Phe Gly Leu
865                 870                 875                 880

Ala Arg Leu Tyr Asn Ser Glu Glu Ser Arg Pro Tyr Thr Asn Lys Val
                885                 890                 895

Ile Thr Leu Trp Tyr Arg Pro Pro Glu Leu Leu Gly Glu Glu Arg
            900                 905                 910

Tyr Thr Pro Ala Ile Asp Val Trp Ser Cys Gly Cys Ile Leu Gly Glu
            915                 920                 925

Leu Phe Thr Lys Pro Ile Phe Gln Ala Asn Leu Glu Leu Ala Gln
930                 935                 940

Leu Glu Leu Ile Ser Arg Leu Cys Gly Ser Pro Cys Pro Ala Val Trp
945                 950                 955                 960

Pro Asp Val Ile Lys Leu Pro Tyr Phe Asn Thr Met Lys Pro Lys Lys
                965                 970                 975

Gln Tyr Arg Arg Arg Leu Arg Glu Phe Ser Phe Ile Pro Ser Ala
            980                 985                 990

Ala Leu Asp Leu Leu Asp His Met Leu Thr Leu Asp Pro Ser Lys Arg
            995                 1000                1005

Cys Thr Ala Glu Gln Thr Leu Gln Ser Asp Phe Leu Lys Asp Val
    1010                1015                1020

Glu Leu Ser Lys Met Ala Pro Pro Asp Leu Pro His Trp Gln Asp
    1025                1030                1035

Cys His Glu Leu Trp Ser Lys Lys Arg Arg Arg Gln Arg Gln Ser
```

-continued

```
            1040                1045                1050
Gly Val Val Val Glu Glu Pro Pro Ser Lys Thr Ser Arg Lys
        1055                1060                1065
Glu Thr Thr Ser Gly Thr Ser Thr Glu Pro Val Lys Asn Ser Ser
        1070                1075                1080
Pro Ala Pro Pro Gln Pro Ala Pro Gly Lys Val Glu Ser Gly Ala
        1085                1090                1095
Gly Asp Ala Ile Gly Leu Ala Asp Ile Thr Gln Gln Leu Asn Gln
        1100                1105                1110
Ser Glu Leu Ala Val Leu Leu Asn Leu Leu Gln Ser Gln Thr Asp
        1115                1120                1125
Leu Ser Ile Pro Gln Met Ala Gln Leu Leu Asn Ile His Ser Asn
        1130                1135                1140
Pro Glu Met Gln Gln Gln Leu Glu Ala Leu Asn Gln Ser Ile Ser
        1145                1150                1155
Ala Leu Thr Glu Ala Thr Ser Gln Gln Gln Asp Ser Glu Thr Met
        1160                1165                1170
Ala Pro Glu Glu Ser Leu Lys Glu Ala Pro Ser Ala Pro Val Ile
        1175                1180                1185
Leu Pro Ser Ala Glu Gln Thr Thr Leu Glu Ala Ser Ser Thr Pro
        1190                1195                1200
Ala Asp Met Gln Asn Ile Leu Ala Val Leu Leu Ser Gln Leu Met
        1205                1210                1215
Lys Thr Gln Glu Pro Ala Gly Ser Leu Glu Glu Asn Asn Ser Asp
        1220                1225                1230
Lys Asn Ser Gly Pro Gln Gly Pro Arg Arg Thr Pro Thr Met Pro
        1235                1240                1245
Gln Glu Glu Ala Ala Ala Cys Pro Pro His Ile Leu Pro Pro Glu
        1250                1255                1260
Lys Arg Pro Pro Glu Pro Pro Gly Pro Pro Pro Pro Pro Pro Pro
        1265                1270                1275
Pro Pro Leu Val Glu Gly Asp Leu Ser Ser Ala Pro Gln Glu Leu
        1280                1285                1290
Asn Pro Ala Val Thr Ala Ala Leu Leu Gln Leu Leu Ser Gln Pro
        1295                1300                1305
Glu Ala Glu Pro Pro Gly His Leu Pro His Glu His Gln Ala Leu
        1310                1315                1320
Arg Pro Met Glu Tyr Ser Thr Arg Pro Arg Pro Asn Arg Thr Tyr
        1325                1330                1335
Gly Asn Thr Asp Gly Pro Glu Thr Gly Phe Ser Ala Ile Asp Thr
        1340                1345                1350
Asp Glu Arg Asn Ser Gly Pro Ala Leu Thr Glu Ser Leu Val Gln
        1355                1360                1365
Thr Leu Val Lys Asn Arg Thr Phe Ser Gly Ser Leu Ser His Leu
        1370                1375                1380
Gly Glu Ser Ser Ser Tyr Gln Gly Thr Gly Ser Val Gln Phe Pro
        1385                1390                1395
Gly Asp Gln Asp Leu Arg Phe Ala Arg Val Pro Leu Ala Leu His
        1400                1405                1410
Pro Val Val Gly Gln Pro Phe Leu Lys Ala Glu Gly Ser Ser Asn
        1415                1420                1425
Ser Val Val His Ala Glu Thr Lys Leu Gln Asn Tyr Gly Glu Leu
        1430                1435                1440
```

```
Gly Pro Gly Thr Thr Gly Ala  Ser Ser Ser Gly Ala  Gly Leu His
    1445            1450                 1455

Trp Gly Gly Pro Thr Gln Ser  Ser Ala Tyr Gly Lys  Leu Tyr Arg
    1460            1465                 1470

Gly Pro Thr Arg Val Pro Pro  Arg Gly Gly Arg Gly  Arg Gly Val
    1475            1480                 1485

Pro Tyr
    1490

<210> SEQ ID NO 3
<211> LENGTH: 25
<212> TYPE: DNA
<213> ORGANISM: Homo sapiens

<400> SEQUENCE: 3
cactgtcgga cattcgggaa ggtgc                                         25

<210> SEQ ID NO 4
<211> LENGTH: 26
<212> TYPE: DNA
<213> ORGANISM: Homo sapiens

<400> SEQUENCE: 4
gcttgcacgt gtggctcaag cagctg                                        26

<210> SEQ ID NO 5
<211> LENGTH: 21
<212> TYPE: RNA
<213> ORGANISM: Homo sapiens

<400> SEQUENCE: 5
acgugacacg uucggagaau u                                             21

<210> SEQ ID NO 6
<211> LENGTH: 25
<212> TYPE: RNA
<213> ORGANISM: Homo sapiens

<400> SEQUENCE: 6
cgaaauaaug auguuggcac caguu                                         25
```